United States Patent
Wu et al.

(10) Patent No.: US 10,844,429 B2
(45) Date of Patent: Nov. 24, 2020

(54) METHODS AND SYSTEMS FOR GENERATION AND ERROR-CORRECTION OF UNIQUE MOLECULAR INDEX SETS WITH HETEROGENEOUS MOLECULAR LENGTHS

(71) Applicant: Illumina, Inc., San Diego, CA (US)

(72) Inventors: Kevin Wu, San Diego, CA (US); Chen Zhao, San Diego, CA (US); Han-Yu Chuang, San Diego, CA (US); Alex So, San Diego, CA (US); Stephen Tanner, San Diego, CA (US); Stephen M. Gross, San Diego, CA (US)

(73) Assignee: Illumina, Inc., San Diego, CA (US)

(*) Notice: Subject to any disclaimer, the term of this patent is extended or adjusted under 35 U.S.C. 154(b) by 198 days.

(21) Appl. No.: 15/863,737

(22) Filed: Jan. 5, 2018

(65) Prior Publication Data
US 2018/0201992 A1 Jul. 19, 2018

Related U.S. Application Data

(60) Provisional application No. 62/447,851, filed on Jan. 18, 2017.

(51) Int. Cl.
*G01N 33/48* (2006.01)
*G01N 33/50* (2006.01)
*C12Q 1/6869* (2018.01)
*C12Q 1/6855* (2018.01)
*G16B 25/00* (2019.01)
*G16B 30/00* (2019.01)

(52) U.S. Cl.
CPC ......... *C12Q 1/6869* (2013.01); *C12Q 1/6855* (2013.01); *G16B 25/00* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 6,159,736 A | 12/2000 | Reznikoff et al. | |
| 7,057,026 B2 | 6/2006 | Barnes et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 8,822,150 B2 | 9/2014 | Bignell et al. | |
| 9,260,745 B2 | 2/2016 | Rava et al. | |
| 9,845,552 B2 | 12/2017 | Blume et al. | |
| 2004/0018520 A1* | 1/2004 | Thompson | C07H 21/04 435/6.14 |
| 2008/0108082 A1 | 5/2008 | Rank et al. | |
| 2009/0026082 A1 | 1/2009 | Rothberg et al. | |
| 2011/0245085 A1 | 10/2011 | Rava et al. | |
| 2012/0245037 A1 | 9/2012 | Hogers et al. | |
| 2014/0024541 A1 | 1/2014 | Richards | |
| 2014/0329698 A1 | 11/2014 | Bignell et al. | |
| 2015/0044687 A1 | 2/2015 | Schmitt et al. | |
| 2015/0094961 A1* | 4/2015 | Kermani | G16B 30/00 702/19 |
| 2015/0275289 A1 | 10/2015 | Otwinowski | |
| 2016/0319345 A1 | 11/2016 | Gnerre et al. | |
| 2019/0085384 A1 | 3/2019 | Zhao et al. | |

FOREIGN PATENT DOCUMENTS

| | | |
|---|---|---|
| WO | WO 91/06678 | 5/1991 |
| WO | WO 95/23875 A1 | 9/1995 |
| WO | WO 98/044151 | 10/1998 |
| WO | WO 00/018957 | 4/2000 |
| WO | WO 2004/018497 A2 | 3/2004 |
| WO | WO 2005/065814 A1 | 7/2005 |
| WO | WO 2006/064199 | 6/2006 |
| WO | WO 2007/010251 A2 | 1/2007 |

(Continued)

OTHER PUBLICATIONS

Craig et al. Ordering of cosmid clones covering the Herpes simplex virus type I (HSV-I) genome: a test case for fingerprinting by hybridisation. Nucleic Acids Research, vol. 18, pp. 2653-2660. (Year: 1990).* http://bio-bwa.sourceforge.net/, Burrows-Wheeler Aligner 2018.
http://hannonlab.cshl.edu/nxCode/nxCode/main.htm, 2018.
https://www.niehs.nih.gov/research/resources/software/biostatistics/art/, 2018.
"Human Genome Browser—hg18 assembly", http://genome.ucsc.edu/cgi-bin/hgGateway?org=Human&db=hg18&hgsid=166260105, 2018.
"Human Genome Browser—hg19 assembly", https://genome.ucsc.edu/cgi-bin/hgGateway?db=hg19, 2018.
"Illumina.com/documents/products/technotes/technote_nextera_matepair_data_processing.pdf", 2012.

(Continued)

*Primary Examiner* — Russell S Negin
(74) *Attorney, Agent, or Firm* — Weaver Austin Villeneuve & Sampson LLP

(57) ABSTRACT

The disclosed embodiments concern methods, apparatus, systems and computer program products for determining sequences of interest using unique molecular index sequences that are uniquely associable with individual polynucleotide fragments, including sequences with low allele frequencies and long sequence length. In some implementations, the unique molecular index sequences include variable-length nonrandom sequences. In some implementations, the unique molecular index sequences are associated with the individual polynucleotide fragments based on alignment scores indicating similarity between the unique molecular index sequences and subsequences of sequence reads obtained from the individual polynucleotide fragments. System, apparatus, and computer program products are also provided for determining a sequence of interest implementing the methods disclosed.

10 Claims, 19 Drawing Sheets
Specification includes a Sequence Listing.

(56) References Cited

FOREIGN PATENT DOCUMENTS

| WO | WO 2007/123744 A2 | 11/2007 | |
|---|---|---|---|
| WO | WO 2012/142213 A2 | 10/2012 | |
| WO | WO 2013/009175 A1 | 1/2013 | |
| WO | WO 2013/138510 A9 | 9/2013 | |
| WO | WO 2013/142389 A1 | 9/2013 | |
| WO | WO 2013/173394 A2 | 11/2013 | |
| WO | WO 2014/142850 A1 | 9/2014 | |
| WO | WO 2014/151117 A1 | 9/2014 | |
| WO | WO-2014145820 A2 * | 9/2014 | ....... C12Q 2535/122 |
| WO | WO 2015/100427 A1 | 7/2015 | |
| WO | WO 2015/106941 A1 | 7/2015 | |
| WO | WO 2016/040901 A1 | 3/2016 | |
| WO | WO 2016/168351 A1 | 10/2016 | |
| WO | WO 2016/176091 A1 | 11/2016 | |
| WO | WO 2017/100441 A1 | 6/2017 | |
| WO | 2017214557 A1 | 12/2017 | |

OTHER PUBLICATIONS

Alnemri, E. et al., "Activation of internucleosomal DNA cleavage in human CEM lymphocytes by glucocorticoid and novobiocin. Evidence for a non-Ca2(+)-requiring mechanism(s).", J Biol. Chem 265( 28), 1990, 17323-17333.

Altschul, et al., "Basic Local Alignment Search Tool", J. Mol. Biol. 1990. pp. 403-410, vol. 215., 1990, 403-410.

Bentley, et al., "Accurate whole human genome sequencing using reversible terminator chemistry", Nature, vol. 456, Nov. 6, 2008, 53-59.

Botezatu, et al., "Genetic Analysis of DNA excreted in urine: a new approach for detecting specific genomic DNA sequences from cells dying in an organism", Clin Chem. 46(8 Pt1), Aug. 2000, 1078-84.

Chen, et al., "Microsatellite alterations in plasma DNA of small cell lung cancer patients", Nat Med. 2(9), 1996, 1033-5.

Fan, et al., "Analysis of the size distributions of fetal and maternal cell-free DNA by paired-end sequencing", Clin. Chem 56(8), Aug. 1, 2010, 1279-1286.

Fan, et al., "Noninvasive diagnosis of fetal aneuploidy by shotgun sequencing DNA from maternal blood", Proceedings of the National Academy of Sciences, vol. 105, No. 42, also available at: http://www.pnas.org/cgi/doi/10.1073/pnas.0808319105, Oct. 21, 2008, 16266-71.

Kivioja, et al., "Counting absolute numbers of molecules using unique molecular identifiers", Nature Methods, Nature Publishing Group, GB, vol. 9, No. 1, XP002729237; ISSN: 1548-7105, DOI: 10.1038/NMETH.1778, Jan. 1, 2012, 72-74.

Koide, et al., "Fragmentation of cell-free fetal DNA in plasma and urine of pregnant women", Prenat Diagn. Jul. 2005;25(7), www.interscience.wiley.com, Mar. 14, 2005, 604-7.

Kozarewa, et al., "Amplification-free Illumina sequencing-library preparation facilitates improved mapping and assembly of GC-biased genomes", Nat. Methods, 6(4), Apr. 2009, 291-295.

Langmead, et al., "Ultrafast and memory-efficient alignment of short DNA sequences to the human genome", Genome Biology, vol. 10, 2009, R25.1-R25.10.

Lo, et al., "Presence of fetal DNA in maternal plasma and serum", Lancet. 350(9076), Aug. 16, 1997, 485-487.

Metzker,"Sequencing technologies—the next generation", Nat Rev Genet. 1(1) doi: 10.1038/mg2626. Epub Dec. 8, 2009, Jan. 2010, p. 31-46.

Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.

Volkerding, et al., Clin Chem 55, 2009, 641-658.

U.S. Office Action dated Sep. 5, 2017 issued in U.S. Appl. No. 15/130,668.

U.S. Final Office Action dated May 11, 2018 issued in U.S. Appl. No. 15/130,668.

U.S. Office Action dated Apr. 9, 2019 issued in U.S. Appl. No. 15/130,668.

Final Office Action dated Nov. 22, 2019 issued in U.S. Appl. No. 15/130,668.

International Search Report and Written Opinion dated Jun. 23, 2016 issued in Application No. PCT/US2016/028430.

International Preliminary Report on Patentabiltiy dated Nov. 9, 2017 issued in Application No. PCT/US2016/028430.

International Search Report and Written Opinion dated Nov. 7, 2018 issued in Application No. PCT/US2018/050968.

International Search Report and Written Opinion dated Apr. 5, 2018 issued in Application No. PCT/US2018/012669.

International Preliminary Report on Patentability dated Aug. 1, 2019 issued in Application No. PCT/US2018/012669.

European Examination Report dated Oct. 24, 2018 in EP Application No. 16720269.6.

New Zealand First Examination Report dated Jun. 25, 2018 in NZ Application No. 736609 [211888].

International Preliminary Report on Patentability dated Nov. 18, 2019 in Application No. PCT/US2018/050968.

Indian Office Action dated Mar. 3, 2020 issued in Application No. 201717040437.

Brazilian Office Action and Search Report dated Jan. 7, 2020 issued in Application No. BR 11 2017 024118.8.

Alcaide et al., "Targeted error-suppressed quantification of circulating tumor DNA using semi-degenerate barcoded adapters and biotinylated baits," Scientific Reports, vol. 7, No. 1, Sep. 2017, pp. 1-19.

Casbon, et al. "A method for counting PCR template molecules with application to next-generation sequencing," Nucleic Acids Research, vol. 39, No. 12, Apr. 13, 2011, pp. 1-8.

Forshew et al. (2012) "Noninvasive identification and monitoring of cancer mutations by targeted deep sequencing of plasma DNA," Science Translational Medicine, vol. 4 Issue 136, 136ra68.

Genomeweb [webpage] "Stanford team develops two-step error correction method for liquid biopsy assay", Mar. 28, 2016, pp. 1-3. [retrieved on Apr. 13, 2016] <URL:https://www.genomeweb.com/sequencing-technology/stanford-team-develops-two-step-error-correction-method-liquid-biopsy-assay>.

Gregory et al., "Targeted single molecule mutation detection with massively parallel sequencing," Nucleic Acids Research, vol. 44, No. 3, Sep. 17, 2015, pp. 1-11.

Jabara et al., "Accurate sampling and deep sequencing of the HIV-1 protease gene using a Primer ID," PNAS, vol. 108, No. 50, Dec. 13, 2011, pp. 20166-20171.

Kennedy et al., (2013) "Ultra-sensitive sequencing reveals an age-related increase in somatic mitochondrial mutations that are inconsistent with oxidative damage," PLOS Genetics, vol. 9 Issue 9, e1003794.

Kennedy et al., (2014) "Detecting ultralow-frequency mutations by duplex sequencing," Nature Protocols, Nature America, Inc., vol. 9 No. 11, 2586.

Kinde et al., "Detection and qualification of rare mutations with massively parallel sequencing," PNAS, vol. 108, No. 23, Jun. 7, 2011, pp. 9530-9535.

Schmitt et al. (2015) "Sequencing small genomic targets with high efficiency and extreme accuracy," Nature Methods, 12(5): 423-425.

Smith et al., "UMI-tools: Modeling sequencing errors in Unique Molecular Identifiers to improve quantification accuracy," Genome Research, vol. 27, No. 3, Jan. 2017, pp. 491-499.

Varscan, "http://varscan.sourceforge.net/", Version 2.2.5, Version 2.2.5, Apr. 2011, 13, 77.

Notice of Allowance dated Jul. 20, 2020 issued in U.S. Appl. No. 15/130,668.

\* cited by examiner

150

|    | Q  | G  | T  | C  | T  | T  | C  | G  |
|----|----|----|----|----|----|----|----|----|
| S1 | 0  | -1 | -2 | -3 | -4 | -5 | -6 | -7 |
| A  | -1 | -1 | -2 | -3 | -4 | -5 | -6 | -7 |
| A  | -2 | -2 | -2 | -3 | -4 | -5 | -6 | -7 |
| C  | -3 | -3 | -3 | -1 | -2 | -3 | -4 | -5 |
| T  | -4 | -4 | -2 | -2 | 0  | -1 | -2 | -3 |
| T  | -5 | -5 | -3 | -3 | -1 | 1  | 0  | -1 |
| C  | -6 | -6 | -4 | -2 | -2 | 0  | 2  | 1  |

151

Q:  GTCTTC  
S1: AACTTC  } Levenshtein Distance (# addition + # deletion + # substitution) = 2

Q:  GTCTTC  
S1: AACTTC  } Glocal alignment score (# match – Levenshtein Distance) = 2

Levenshtein Distance = 2

152

|    | Q  | G  | T  | C  | T  | T  | C  | G  |
|----|----|----|----|----|----|----|----|----|
| S2 | 0  | -1 | -2 | -3 | -4 | -5 | -6 | -7 |
| C  | -1 | -1 | -2 | -3 | -4 | -5 | -6 | -7 |
| G  | -2 | 0  | -1 | -2 | -2 | -3 | -4 | -3 |
| C  | -3 | -1 | -1 | 0  | -1 | -2 | -2 | -3 |
| T  | -4 | -2 | 0  | -1 | 1  | 0  | -1 | -2 |
| T  | -5 | -3 | -1 | -1 | 0  | 2  | 1  | 0  |
| C  | -6 | -4 | -2 | 0  | -1 | 1  | 3  | 2  |
| G  | -7 | -5 | -3 | -1 | -1 | 0  | 2  | 4  |

153

Q:  GTCTTCG  
S2: CGCTTCG  } Levenshtein distance = 2

Q:  GTCTTCG  
S2: CGCTTCG  } Glocal alignment score = 4

|    | Q  | T  | T  | G  | G  | C  | A  | T  |
|----|----|----|----|----|----|----|----|----|
| S₁ | 0  | -1 | -2 | -3 | -4 | -5 | -6 | -7 |
| T  | -1 | 1  | 0  | -1 | -2 | -3 | -4 | -5 |
| T  | -2 | 0  | 2  | 1  | 0  | -1 | -2 | -3 |
| G  | -3 | -1 | 1  | 3  | 2  | 1  | 0  | -1 |
| T  | -4 | -2 | 0  | 2  | 2  | 1  | 0  | 1  |
| G  | -5 | -3 | -1 | 1  | 3  | 2  | 1  | 0  |
| A  | -6 | -4 | -2 | 0  | 2  | 2  | 3  | 2  |
| C  | -7 | -5 | -3 | -1 | 1  | 3  | 2  | 2  |

Q:  TTGGCAT       Global alignment score = 2
S1: TTGTGAC       Glocal alignment score = 3

162    161

163

|    | Q  | T  | T  | G  | G  | C  | A  | T  |
|----|----|----|----|----|----|----|----|----|
| S₂ | 0  | -1 | -2 | -3 | -4 | -5 | -6 | -7 |
| G  | -1 | -1 | -2 | -1 | -2 | -3 | -4 | -5 |
| G  | -2 | -2 | -2 | -1 | 0  | -1 | -2 | -3 |
| C  | -3 | -3 | -3 | -2 | -1 | 1  | 0  | -1 |
| C  | -4 | -4 | -4 | -3 | -2 | 0  | 0  | -1 |
| A  | -5 | -5 | -5 | -4 | -3 | -1 | 1  | 0  |
| T  | -6 | -4 | -4 | -5 | -4 | -2 | 0  | 2  |

164

Q:  TTGGCAT       Global alignment score = 2
S2: GGCCAT        Glocal alignment score = 2

Figure 1F

(i) Standard dual index TruSeq adapter (ii) UMI replacing sample index 1 position (iii) UMIs in both P5 and P7 arms, prior to sample index reading (iv) UMIs in both P5 and P7 arms, behind sample index reading (v) Dual index adapter with a UMI in the double-stranded region (vi) Short adapter with a UMI in the double-stranded region

SEQUENCE LISTING

```
<160> NUMBER OF SEQ ID NOS: 2

<210> SEQ ID NO 1
<211> LENGTH: 13
<212> TYPE: DNA
<213> ORGANISM: Description of Artificial Sequence: Synthetic
      Polynucleotide
<220> FEATURE:
<221> NAME/KEY: misc_feature
<222> LOCATION: (9)..(13)
<223> OTHER INFORMATION: n is a, c, g, or t

<400> SEQUENCE: 1
ttgtgactnn nnn                                                    13

<210> SEQ ID NO 2
<211> LENGTH: 16
<212> TYPE: DNA
<213> ORGANISM: Description of Artificial Sequence: Synthetic
      Polynucleotide
<220> FEATURE:
<221> NAME/KEY: misc_feature
<222> LOCATION: (12)..(16)
<223> OTHER INFORMATION: n is a, c, g, or t

<400> SEQUENCE: 2
ttggcatgac tnnnnn                                                 16
```

METHODS AND SYSTEMS FOR GENERATION AND ERROR-CORRECTION OF UNIQUE MOLECULAR INDEX SETS WITH HETEROGENEOUS MOLECULAR LENGTHS

CROSS REFERENCE TO RELATED APPLICATIONS

This application claims benefits under 35 U.S.C. § 119(e) to U.S. Provisional Patent Application No. 62/447,851, entitled: METHODS AND SYSTEMS FOR GENERATION AND ERROR-CORRECTION OF UNIQUE MOLECULAR INDEX SETS WITH HETEROGENEOUS MOLECULAR LENGTHS, filed Jan. 18, 2017, which is herein incorporated by reference in its entirety for all purposes.

BACKGROUND

Next generation sequencing technology is providing increasingly high speed of sequencing, allowing larger sequencing depth. However, because sequencing accuracy and sensitivity are affected by errors and noise from various sources, e.g., sample defects, PCR during library preparation, enrichment, clustering, and sequencing, increasing depth of sequencing alone cannot ensure detection of sequences of very low allele frequency, such as in fetal cell-free DNA (cfDNA) in maternal plasma, circulating tumor DNA (ctDNA), and sub-clonal mutations in pathogens. Therefore, it is desirable to develop methods for determining sequences of DNA molecules in small quantity and/or low allele frequency while suppressing sequencing inaccuracy due to various sources of errors.

SUMMARY

The disclosed implementations concern methods, apparatus, systems, and computer program products for determining nucleic acid fragment sequences using unique molecular indices (UMIs). In some implementations, the UMIs includes nonrandom UMIs (NRUMIs) or variable-length, nonrandom unique molecular indices (vNRUMIs).

One aspect of the disclosure provides methods for sequencing nucleic acid molecules from a sample. The method includes: (a) applying adapters to DNA fragments in the sample to obtain DNA-adapter products, wherein each adapter includes a nonrandom unique molecular index, and wherein nonrandom unique molecular indices of the adapters have at least two different molecular lengths and form a set of variable-length, nonrandom unique molecular indices (vNRUMIs); (b) amplifying the DNA-adapter products to obtain a plurality of amplified polynucleotides; (c) sequencing the plurality of amplified polynucleotides, thereby obtaining a plurality of reads associated with the set of vNRUMIs; (d) identifying, among the plurality of reads, reads associated with a same variable-length, nonrandom unique molecular index (vNRUMI); and (e) determining a sequence of a DNA fragment in the sample using the reads associated with the same vNRUMI.

In some implementations, identifying the reads associated with the same vNRUMI includes obtaining, for each read of the plurality of reads, alignment scores with respect to the set of vNRUMIs, each alignment score indicating similarity between a subsequence of a read and a vNRUMI, wherein the subsequence is in a region of the read in which nucleotides derived from the vNRUMI are likely located.

In some implementations, the alignment scores are based on matches of nucleotides and edits of nucleotides between the subsequence of the read and the vNRUMI. In some implementations, the edits of nucleotides include substitutions, additions, and deletions of nucleotides. In some implementations, each alignment score penalizes mismatches at the beginning of a sequence but does not penalize mismatches at the end of the sequence.

In some implementations, obtaining an alignment score between a read and a vNRUMI includes: (a) calculating an alignment score between the vNRUMI and each one of all possible prefix sequences of the subsequence of the read; (b) calculating an alignment score between the subsequence of the read and each one of all possible prefix sequences of the vNRUMI; and (c) obtaining a largest alignment score among the alignment scores calculated in (a) and (b) as the alignment score between the read and the vNRUMI.

In some implementations, the subsequence has a length that equals to a length of the longest vNRUMI in the set of vNRUMIs. In some implementations, identifying the reads associated with the same vNRUMI in (d) further includes: selecting, for each read of the plurality of reads, at least one vNRUMI from the set of vNRUMIs based on the alignment scores; and associating each read of the plurality of reads with the at least one vNRUMI selected for the read.

In some implementations, selecting the at least one vNRUMI from the set of vNRUMIs includes selecting a vNRUMI having a highest alignment score among the set of vNRUMIs. In some implementations, the at least one vNRUMI includes two or more vNRUMIs.

In some implementations, the method further includes selecting one of the two or more vNRUMI as the same vNRUMI of (d) and (e).

In some implementations, the adapters applied in (a) are obtained by: (i) providing a set of oligonucleotide sequences having at least two different molecular lengths; (ii) selecting a subset of oligonucleotide sequences from the set of oligonucleotide sequences, all edit distances between oligonucleotide sequences of the subset of oligonucleotide sequences meeting a threshold value, the subset of oligonucleotide sequences forming the set of vNRUMIs; and (iii) synthesizing the adapters each including a double-stranded hybridized region, a single-stranded 5' arm, a single-stranded 3' arm, and at least one vNRUMI of the set of vNRUMIs. In some implementations, the threshold value is 3. In some implementations, the set of vNRUMIs include vNRUMIs of 6 nucleotides and vNRUMIs of 7 nucleotides.

In some implementations, the determining of (e) includes collapsing reads associated with the same vNRUMI into a group to obtain a consensus nucleotide sequence for the sequence of the DNA fragment in the sample. In some implementations, the consensus nucleotide sequence is obtained based partly on quality scores of the reads.

In some implementations, the determining of (e) includes: identifying, among the reads associated with the same vNRUMI, reads having a same read position or similar read positions in a reference sequence, and determining the sequence of the DNA fragment using reads that (i) are associated with the same vNRUMI and (ii) have the same read position or similar read positions in the reference sequence.

In some implementations, the set of vNRUMIs includes no more than about 10,000 different vNRUMIs. In some implementations, the set of vNRUMIs includes no more than about 1,000 different vNRUMIs. In some implementations, the set of vNRUMIs includes no more than about 200 different vNRUMIs.

In some implementations, applying adapters to the DNA fragments in the sample includes applying adapters to both ends of the DNA fragments in the sample.

Another aspect of the disclosure relates to methods for preparing sequencing adapters, the methods including: (a) providing a set of oligonucleotide sequences having at least two different molecular lengths; (b) selecting a subset of oligonucleotide sequences from the set of oligonucleotide sequences, all edit distances between oligonucleotide sequences of the subset of oligonucleotide sequences meeting a threshold value, the subset of oligonucleotide sequences forming a set of variable-length, nonrandom unique molecular indexes (vNRUMIs); and (c) synthesizing a plurality of sequencing adapters, wherein each sequencing adapter includes a double-stranded hybridized region, a single-stranded 5' arm, a single-stranded 3' arm, and at least one vNRUMI of the set of vNRUMIs.

In some implementations, (b) includes: (i) selecting an oligonucleotide sequence from the set of oligonucleotide sequences; (ii) adding the selected oligonucleotide to an expanding set of oligonucleotide sequences and removing the selected oligonucleotide from the set of oligonucleotide sequences to obtain a reduced set of oligonucleotide sequences; (iii) selecting an instant oligonucleotide sequence from the reduced set that maximizes a distance function, wherein the distance function is a minimal edit distance between the instant oligonucleotide sequence and any oligonucleotide sequences in the expanding set, and wherein the distance function meeting the threshold value; (iv) adding the instant oligonucleotide to the expanding set and removing the instant oligonucleotide from the reduced set; (v) repeating (iii) and (iv) one or more times; and (vi) providing the expanding set as the subset of oligonucleotide sequences forming the set of vNRUMIs.

In some implementations, (v) includes repeating (iii) and (iv) until the distance function no longer meets the threshold value.

In some implementations, (v) includes repeating (iii) and (iv) until the expanding set reaches a defined size.

In some implementations, the instant oligonucleotide sequence or an oligonucleotide sequence in the expanding set is shorter than a longest oligonucleotide sequence in the set of oligonucleotide sequences, the method further including, before (iii), (1) appending a thymine base or a thymine base plus any of four bases to the instant oligonucleotide sequence or the oligonucleotide sequence in the expanding set, thereby generating a padded sequence having the same length as the longest oligonucleotide sequence in the set of oligonucleotide sequences, and (2) using the padded sequence to calculate the minimal edit distance. In some implementations, the edit distances are Levenshtein distances. In some implementations, the threshold value is 3.

In some implementations, the method further including, before (b), removing certain oligonucleotide sequences from the set of oligonucleotide sequences to obtain a filtered set of oligonucleotide sequences; and providing the filtered set of oligonucleotide sequences as the set of oligonucleotide sequences from which the subset is selected.

In some implementations, the certain oligonucleotide sequences include oligonucleotide sequences having three or more consecutive identical bases. In some implementations, the certain oligonucleotide sequences include oligonucleotide sequences having a combined number of guanine and cytosine bases smaller than 2 and oligonucleotide sequences having a combined number of guanine and cytosine bases larger than 4.

In some implementations, the certain oligonucleotide sequences include oligonucleotide sequences having a same base at the last two positions. In some implementations, the certain oligonucleotide sequences include oligonucleotide sequences having a subsequence matching the 3' end of one or more sequencing primers.

In some implementations, the certain oligonucleotide sequences include oligonucleotide sequences having a thymine base at the last position of the oligonucleotide sequences.

In some implementations, the set of vNRUMIs includes vNRUMIs of 6 nucleotides and vNRUMIs of 7 nucleotides.

A further aspect of the disclosure relates to a method for sequencing nucleic acid molecules from a sample, including (a) applying adapters to DNA fragments in the sample to obtain DNA-adapter products, wherein each adapter includes a nonrandom unique molecular index, and wherein nonrandom unique molecular indices of the adapters have at least two different molecular lengths and form a set of variable-length, nonrandom unique molecular indices (vNRUMIs); (b) amplifying the DNA-adapter products to obtain a plurality of amplified polynucleotides; (c) sequencing the plurality of amplified polynucleotides, thereby obtaining a plurality of reads associated with the set of vNRUMIs; and (d) identifying, among the plurality of reads, reads associated with a same variable-length, nonrandom unique molecular index (vNRUMI).

In some implementations, the method further includes obtaining a count of the reads associated with the same vNRUMI.

Another aspect of the disclosure relates to a method for sequencing nucleic acid molecules from a sample, including (a) applying adapters to DNA fragments in the sample to obtain DNA-adapter products, wherein each adapter includes a unique molecular index (UMI), and wherein unique molecular indices (UMIs) of the adapters have at least two different molecular lengths and form a set of variable-length unique molecular indices (vUMIs); (b) amplifying the DNA-adapter products to obtain a plurality of amplified polynucleotides; (c) sequencing the plurality of amplified polynucleotides, thereby obtaining a plurality of reads associated with the set of vUMIs; and (d) identifying, among the plurality of reads, reads associated with a same variable-length unique molecular index (vUMI).

In some implementations, the method further includes determining a sequence of a DNA fragment in the sample using the reads associated with the same vUMI.

In some implementations, the method further includes obtaining a count of the reads associated with the same vUMIs.

Yet another aspect of the disclosure relates to method for sequencing nucleic acid molecules from a sample, including (a) applying adapters to DNA fragments in the sample to obtain DNA-adapter products, wherein each adapter includes a unique molecular index (UMI) in a set of unique molecular indices (UMIs); (b) amplifying the DNA-adapter products to obtain a plurality of amplified polynucleotides; (c) sequencing the plurality of amplified polynucleotides, thereby obtaining a plurality of reads associated with the set of UMIs; (d) obtaining, for each read of the plurality of reads, alignment scores with respect to the set of UMIs, each alignment score indicating similarity between a subsequence of a read and a UMI; (e) identifying, among the plurality of reads, reads associated with a same UMI using the alignment scores; and (e) determining a sequence of a DNA fragment in the sample using the reads associated with the same UMI.

In some implementations, the alignment scores are based on matches of nucleotides and edits of nucleotides between the subsequence of the read and the UMI. In some implementations, each alignment score penalizes mismatches at the beginning of a sequence but does not penalize mismatches at the end of the sequence. In some implementations, the set of UMIs includes UMIs of at least two different molecular lengths.

System, apparatus, and computer program products are also provided for determining DNA fragment sequences implementing the methods disclosed.

One aspect of the disclosure provides a computer program product including a non-transitory machine readable medium storing program code that, when executed by one or more processors of a computer system, causes the computer system to implement a method for determining sequence information of a sequence of interest in a sample using unique molecular indices (UMIs). The program code includes instructions to perform the methods above.

Although the examples herein concern humans and the language is primarily directed to human concerns, the concepts described herein are applicable to nucleic acids from any virus, plant, animal, or other organism, and to populations of the same (metagenomes, viral populations, etc.) These and other features of the present disclosure will become more fully apparent from the following description, with reference to the figures, and the appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 1E shows examples of how a subsequence of a read or a query sequence (Q) can be compared to two reference sequences (S1 and S2) in the vNRUMI set.

FIG. 1F illustrates examples of how glocal alignment scores can provide better error suppression than global alignment scores.

DETAILED DESCRIPTION

Figure 1A:
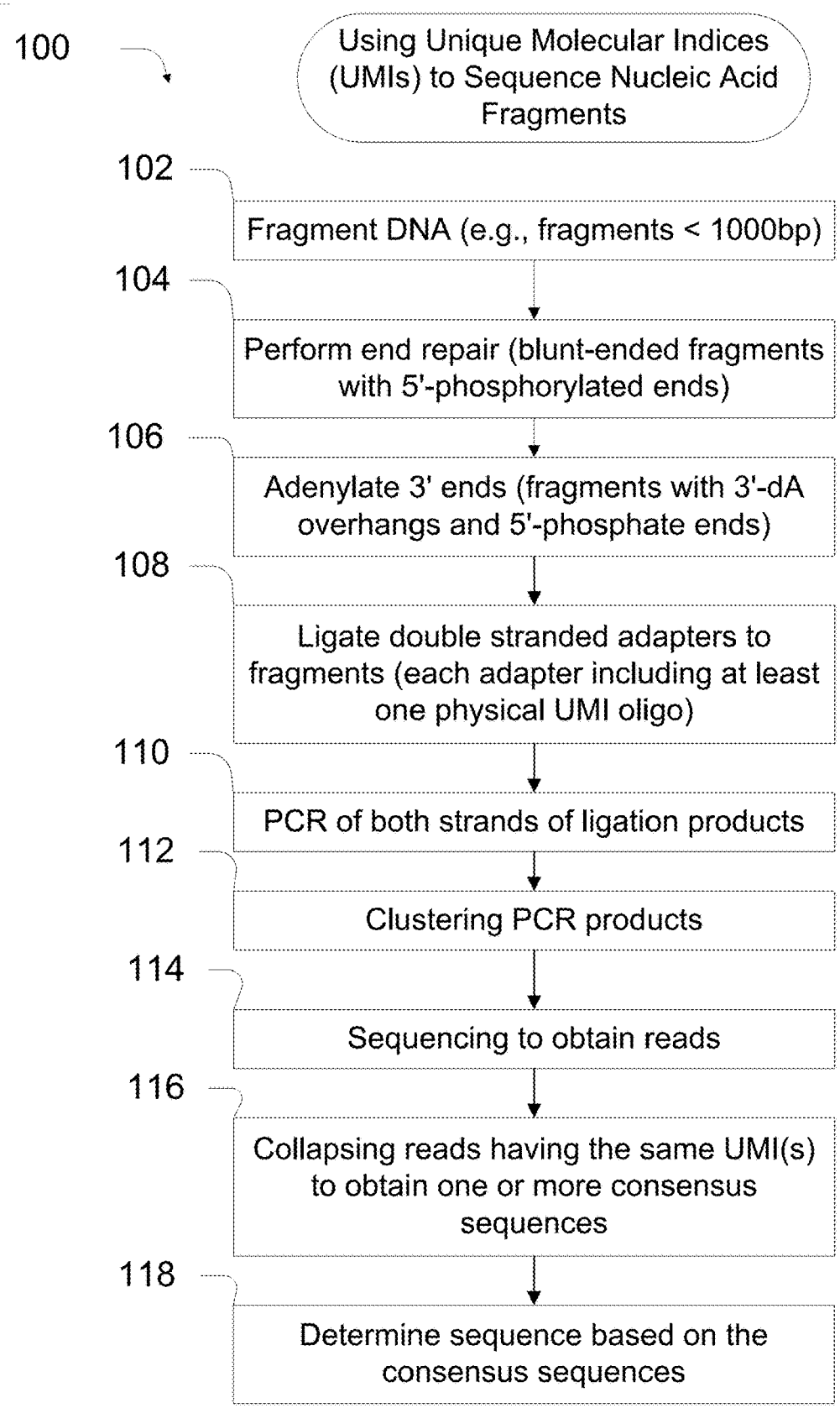
FIG. 1A is a flow chart illustrating an example workflow using UMIs to sequence nucleic acid fragments.

The disclosure concerns methods, apparatus, systems, and computer program products for sequencing nucleic acids, especially nucleic acids with limited quantity or low concentration, such as fetal cfDNA in maternal plasma or circulating tumor DNA (ctDNA) in a cancer patient's blood.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

Unique molecular indices (UMIs) are sequences of nucleotides applied to or identified in DNA molecules that may be used to distinguish individual DNA molecules from one another. Since UMIs are used to identify DNA molecules, they are also referred to as unique molecular identifiers. See, e.g., Kivioja, Nature Methods 9, 72-74 (2012). UMIs may be sequenced along with the DNA molecules with which they are associated to determine whether the read sequences are those of one source DNA molecule or another. The term "UMI" is used herein to refer to both the sequence information of a polynucleotide and the physical polynucleotide per se.

Commonly, multiple instances of a single source molecule are sequenced. In the case of sequencing by synthesis using Illumina's sequencing technology, the source molecule may be PCR amplified before delivery to a flow cell. Whether or not PCR amplified, the individual DNA molecules applied to flow cell are bridge amplified or ExAmp amplified to produce a cluster. Each molecule in a cluster derives from the same source DNA molecule but is separately sequenced. For error correction and other purposes, it can be important to determine that all reads from a single cluster are identified as deriving from the same source molecule. UMIs allow this grouping. A DNA molecule that is copied by amplification or otherwise to produce multiple instances of the DNA molecule is referred to as a source DNA molecule.

In addition to errors associated with the source DNA molecules, errors can also occur in a region associated with the UMIs. In some implementations, the latter type of error may be corrected by mapping a read sequence to a most likely UMI among a pool of UMIs.

UMIs are similar to bar codes, which are commonly used to distinguish reads of one sample from reads of other samples, but UMIs are instead used to distinguish one source DNA molecule from another when many DNA molecules are sequenced together. Because there may be many more DNA molecules in a sample than samples in a sequencing run, there are typically many more distinct UMIs than distinct barcodes in a sequencing run.

As mentioned, UMIs may be applied to or identified in individual DNA molecules. In some implementations, the UMIs may be applied to the DNA molecules by methods that physically link or bond the UMIs to the DNA molecules, e.g., by ligation or transposition through polymerase, endonuclease, transposases, etc. These "applied" UMIs are therefore also referred to as physical UMIs. In some contexts, they may also be referred to as exogenous UMIs. The UMIs identified within source DNA molecules are referred to as virtual UMIs. In some context, virtual UMIs may also be referred to as endogenous UMI.

Physical UMIs may be defined in many ways. For example, they may be random, pseudo-random or partially random, or nonrandom nucleotide sequences that are inserted in adapters or otherwise incorporated in source DNA molecules to be sequenced. In some implementations, the physical UMIs may be so unique that each of them is expected to uniquely identify any given source DNA molecule present in a sample. The collection of adapters is generated, each having a physical UMI, and those adapters are attached to fragments or other source DNA molecules to be sequenced, and the individual sequenced molecules each has a UMI that helps distinguish it from all other fragments. In such implementations, a very large number of different physical UMIs (e.g., many thousands to millions) may be used to uniquely identify DNA fragments in a sample.

Of course, the physical UMI must have a sufficient length to ensure this uniqueness for each and every source DNA molecule. In some implementations, a less unique molecular identifier can be used in conjunction with other identification techniques to ensure that each source DNA molecule is uniquely identified during the sequencing process. In such implementations, multiple fragments or adapters may have the same physical UMI. Other information such as alignment location or virtual UMIs may be combined with the physical UMI to uniquely identify reads as being derived from a single source DNA molecule/fragment. In some implementations, adaptors include physical UMIs limited to a relatively small number of nonrandom sequences, e.g., 120 nonrandom sequences. Such physical UMIs are also referred to as nonrandom UMIs. In some implementations, the nonrandom UMIs may be combined with sequence position information, sequence position, and/or virtual UMIs to identify reads attributable to a same source DNA molecule. The identified reads may be combined to obtain a consensus sequence that reflects the sequence of the source DNA molecule as described herein. Using physical UMIs, virtual UMIs, and/or alignment locations, one can identify reads having the same or related UMIs or locations, which identified reads can then be combined to obtain one or more consensus sequences. The process for combining reads to obtain a consensus sequence is also referred to as "collapsing" reads, which is further described hereinafter.

A "virtual unique molecular index" or "virtual UMI" is a unique sub-sequence in a source DNA molecule. In some implementations, virtual UMIs are located at or near the ends of the source DNA molecule. One or more such unique end positions may alone or in conjunction with other information uniquely identify a source DNA molecule. Depending on the number of distinct source DNA molecules and the number of nucleotides in the virtual UMI, one or more virtual UMIs can uniquely identify source DNA molecules in a sample. In some cases, a combination of two virtual unique molecular identifiers is required to identify a source DNA molecule. Such combinations may be extremely rare, possibly found only once in a sample. In some cases, one or more virtual UMIs in combination with one or more physical UMIs may together uniquely identify a source DNA molecule.

A "random UMI" may be considered a physical UMI selected as a random sample, with or without replacement, from a set of UMIs consisting of all possible different oligonucleotide sequences given one or more sequence lengths. For instance, if each UMI in the set of UMIs has n nucleotides, then the set includes $4^n$ UMIs having sequences that are different from each other. A random sample selected from the $4^n$ UMIs constitutes a random UMI.

Conversely, a "nonrandom UMI" (NRUMI) as used herein refers to a physical UMI that is not a random UMI. In some embodiments, nonrandom UMIs are predefined for a particular experiment or application. In certain embodiments, rules are used to generate sequences for a set or select a sample from the set to obtain a nonrandom UMI. For instance, the sequences of a set may be generated such that the sequences have a particular pattern or patterns. In some implementations, each sequence differs from every other sequence in the set by a particular number of (e.g., 2, 3, or 4) nucleotides. That is, no nonrandom UMI sequence can be converted to any other available nonrandom UMI sequence by replacing fewer than the particular number of nucleotides. In some implementations, a set of NRUMIs used in a sequencing process includes fewer than all possible UMIs given a particular sequence length. For instance, a set of NRUMIs having 6 nucleotides may include a total of 96 different sequences, instead of a total of $4^6=4096$ possible different sequences.

In some implementations where nonrandom UMIs are selected from a set with fewer than all possible different sequences, the number of nonrandom UMIs is fewer, sometimes significantly so, than the number of source DNA molecules. In such implementations, nonrandom UMI information may be combined with other information, such as virtual UMIs, read locations on a reference sequence, and/or sequence information of reads, to identify sequence reads deriving from a same source DNA molecule.

The term "variable-length, nonrandom molecular index" (vNRUMI) refers to an UMI in a set of vNRUMIs selected from a pool of UMIs of variable molecular lengths (or heterogeneous length) using a nonrandom selection process. The term vNRUMI is used to refer to both the molecule of the UMI as well as the sequence of the UMI. In some implementations, certain UMIs may be removed from the pool of UMIs to provide a filtered pool of UMIs, which pool is then used to generate the set of vNRUMIs.

In some implementations, each vNRUMI differs from every other vNRUMI in the set used in a process by at least a defined edit distance. In some implementations, a set of vNRUMIs used in a sequencing process includes fewer than all possible UMIs given the relevant molecular lengths. For instance, a set of vNRUMIs having 6 and 7 nucleotides may include a total of 120 different sequences (instead of a total of $4^6+4^7=20480$ possible different sequences). In other implementations, sequences are not randomly selected from a set. Instead, some sequences are selected with higher probability than other sequences.

The term "molecular length" is also referred to as sequence length, and can be measured in nucleotides. The term molecular length is also used interchangeably with the terms molecular size, DNA size, and sequence length.

Edit distance is a metric quantifying how dissimilar two strings (e.g., words) are to one another by counting the minimum number of operations required to transform one string into the other. In bioinformatics, it can be used to quantify the similarity of DNA sequences, which can be viewed as strings of the letters A, C, G and T.

Different forms of edit distance use different sets of string operations. The Levenshtein distance is a common type of edit distance. The string operations of Levenshtein distance account for numbers of deletions, insertions, and substitutions of characters in the string. In some implementations, other variants of edit distances may be used. For instance, other variants of edit distance can be obtained by restricting the set of operations. Longest common subsequence (LCS) distance is edit distance with insertion and deletion as the only two edit operations, both at unit cost. Similarly, by only allowing substitutions, Hamming distance is obtained, which is restricted to equal-length strings. Jaro-Winkler distance can be obtained from an edit distance where only transpositions are allowed.

In some implementations, different string operations can be weighted differently for an edit distance. For instance, a substitution operation may be weighted by a value of 3, while an indel may be weighted by a value of 2. In some implementations, matches of different kinds may be weighted differently. For example an A-A match might be weighted twice as much as a G-G match.

An alignment score is a score indicating a similarity of two sequences determined using an alignment method. In some implementations, an alignment score accounts for number of edits (e.g., deletions, insertions, and substitutions of characters in the string). In some implementations, an alignment score accounts for a number of matches. In some implementations, an alignment score accounts for both the number of matches and a number of edits. In some implementations, the number of matches and edits are equally weighted for the alignment score. For example, an alignment score can be calculated as: # of matches−# of insertions−# of deletions−# of substitutions. In other implementations, the numbers of matches and edits can be weighted differently. For example, an alignment score can be calculated as: # of matches×5−# of insertions×4−# of deletions×4−# of substitutions×6.

The term "paired end reads" refers to reads obtained from paired end sequencing that obtains one read from each end of a nucleic fragment. Paired end sequencing involves fragmenting DNA into sequences called inserts. In some protocols such as some used by Illumina, the reads from shorter inserts (e.g., on the order of tens to hundreds of bp) are referred to as short-insert paired end reads or simply paired end reads. In contrast, the reads from longer inserts (e.g., on the order of several thousands of bp) are referred to as mate pair reads. In this disclosure, short-insert paired end reads and long-insert mate pair reads may both be used and are not differentiated with regard to the process for determining sequences of DNA fragments. Therefore, the term "paired end reads" may refer to both short-insert paired end reads and long-insert mate pair reads, which are further described herein after. In some embodiments, paired end reads include reads of about 20 bp to 1000 bp. In some embodiments, paired end reads include reads of about 50 bp to 500 bp, about 80 bp to 150 bp, or about 100 bp.

As used herein, the terms "alignment" and "aligning" refer to the process of comparing a read to a reference sequence and thereby determining whether the reference sequence contains the read sequence. An alignment process, as used herein, attempts to determine if a read can be mapped to a reference sequence, but does not always result in a read aligned to the reference sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13.

Of course, alignment tools have many additional aspects and many other applications in bioinformatics that are not described in this application. For instance, alignments can also be used to determine how similar two DNA sequences from two different species are, thus providing a measure of how closely related they are on an evolutionary tree.

In some implementations herein, alignment is performed between a subsequence of a read and a vNRUMI as reference sequence to determine an alignment score as further described herein after. Alignment scores between a read and multiple vNRUMIs can then be used to determine which one of the vNRUMIs the read should be associated with or mapped to.

In some cases, an alignment additionally indicates a location in the reference sequence where the read maps to. For example, if the reference sequence is the whole human genome sequence, an alignment may indicate that a read is present on chromosome 13, and may further indicate that the read is on a particular strand and/or site of chromosome 13. In some scenarios, alignment tools are imperfect, in that a) not all valid alignments are found, and b) some obtained alignments are invalid. This happens due to various reasons, e.g., reads may contain errors, and sequenced reads may be different from the reference genome due to haplotype differences. In some applications, the alignment tools include built-in mismatch tolerance, which tolerates certain degrees of mismatch of base pairs and still allow alignment of reads to a reference sequence. This can help to identify valid alignment of reads that would otherwise be missed.

Aligned reads are one or more sequences that are identified as a match in terms of the order of their nucleic acid molecules to a known reference sequence such as a reference genome. An aligned read and its determined location on the reference sequence constitute a sequence tag. Alignment can be done manually, although it is typically implemented by a computer algorithm, as it would be impossible to align reads in a reasonable time period for implementing the methods disclosed herein. One example of an algorithm from aligning sequences is the global-local (glocal) hybrid alignment method for comparing a prefix sequence of a read to a vNRUMI as further described hereinafter. Another example of an alignment method is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. patent application Ser. No. 14/354,528, filed Apr. 25, 2014, which is incorporated herein by reference in its entirety. The matching of a sequence read in aligning can be a 100% sequence match or less than 100% (i.e., a non-perfect match). Additional alignment methods are disclosed in U.S. patent application Ser. No. 15/130,668 filed no Apr. 15, 2016, which is incorporated by reference in its entirety.

The term "mapping" used herein refers to assigning a read sequence to a larger sequence, e.g., a reference genome, by alignment.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

The term "test sample" herein refers to a sample, typically derived from a biological fluid, cell, tissue, organ, or organism, that includes a nucleic acid or a mixture of nucleic acids having at least one nucleic acid sequence that is to be screened for copy number variation and other genetic alterations, such as, but not limited to, single nucleotide polymorphism, insertions, deletions, and structural variations. In certain embodiments the sample has at least one nucleic acid sequence whose copy number is suspected of having undergone variation. Such samples include, but are not limited to sputum/oral fluid, amniotic fluid, blood, a blood fraction, or fine needle biopsy samples, urine, peritoneal fluid, pleural fluid, and the like. Although the sample is often taken from a human subject (e.g., a patient), the assays can be used for samples from any mammal, including, but not limited to dogs, cats, horses, goats, sheep, cattle, pigs, etc., as well as mixed populations, as microbial populations from the wild, or viral populations from patients. The sample may be used directly as obtained from the biological source or following a pretreatment to modify the character of the sample. For example, such pretreatment may include preparing plasma from blood, diluting viscous fluids, and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "read" refers to a sequence read from a portion of a nucleic acid sample. Typically, though not necessarily, a read represents a short sequence of contiguous base pairs in the sample. The read may be represented symbolically by the base pair sequence in A, T, C, and G of the sample portion, together with a probabilistic estimate of the correctness of the base (quality score). It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 20 bp) that can be used to identify a larger sequence or region, e.g., that can be aligned and mapped to a chromosome or genomic region or gene.

The terms "site" and "alignment location" are used interchangeably to refer to a unique position (i.e. chromosome ID, chromosome position and orientation) on a reference genome. In some embodiments, a site may be a residue's, a sequence tag's, or a segment's position on a reference sequence.

As used herein, the term "reference genome" or "reference sequence" refers to any particular known genetic sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. However, it is understood that "complete" is a relative concept, because even the gold-standard reference genome is expected to include gaps and errors.

In some implementations, a vNRUMI sequence may be used as a reference sequence to which a prefix sequence of a read is aligned to. The alignment provides an alignment score between the prefix sequence of the read and the vNRUMI, which can be used to determine whether the read and the vNRUMI should be associated in a process for collapsing reads associated with the same vNRUMI.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In some embodiments, a reference sequence for alignment may have a sequence length from about 1 to about 100 times the length of a read. In such embodiments, the alignment and sequencing are considered a targeted alignment or sequencing, instead of a whole genome alignment or sequencing. In these embodiments, the reference sequence typically includes a gene sequence and/or other constrained sequence of interest. In this sense, the alignment of a subsequence of a read to a vNRUMI is a form of targeted alignment.

In various embodiments, the reference sequence is a consensus sequence or other combination derived from multiple individuals. However, in certain applications, the reference sequence may be taken from a particular individual.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, necessary ions and molecules, and a suitable temperature and pH). The primer may be preferably single stranded for maximum efficiency in amplification, but alternatively may be double stranded. If double stranded, the primer is first treated to separate its strands before being used to prepare extension products. The primer may be an oligodeoxyribonucleotide. The primer is sufficiently long to prime the synthesis of extension products in the presence of the inducing agent. The exact lengths of the primers will depend on many factors, including temperature, source of primer, use of the method, and the parameters used for primer design.

Introduction and Context

Next generation sequencing (NGS) technology has developed rapidly, providing new tools to advance research and science, as well as healthcare and services relying on genetic and related biological information. NGS methods are performed in a massively parallel fashion, affording increasingly high speed for determining biomolecules sequence information. However, many of the NGS methods and associated sample manipulation techniques introduce errors such that the resulting sequences have relatively high error rate, ranging from one error in a few hundred base pairs to one error in a few thousand base pairs. Such error rates are sometimes acceptable for determining inheritable genetic information such as germline mutations because such information is consistent across most somatic cells, which provide many copies of the same genome in a test sample. An error originating from reading one copy of a sequence has a minor or removable impact when many copies of the same sequence are read without error. For instance, if an erroneous read from one copy of a sequence cannot be properly aligned to a reference sequence, it may simply be discarded from analysis. Error-free reads from other copies of the same sequence may still provide sufficient information for valid analyses. Alternatively, instead of discarding the read having a base pair different from other reads from the same sequence, one can disregard the different base pair as resulting from a known or unknown source of error.

However, such error correction approaches do not work well for detecting sequences with low allele frequencies, such as sub-clonal, somatic mutations found in nucleic acids from tumor tissue, circulating tumor DNA, low-concentration fetal cfDNA in maternal plasma, drug-resistant mutations of pathogens, etc. In these examples, one DNA fragment may harbor a somatic mutation of interest at a sequence site, while many other fragments at the same sequence site do not have the mutation of interest. In such a scenario, the sequence reads or base pairs from the mutated DNA fragment might be unused or misinterpreted in conventional sequencing, thereby losing information for detecting the mutation of interest.

Due to these various sources of errors, increasing depth of sequencing alone cannot ensure detection of somatic variations with very low allele frequency (e.g., <1%). Some implementations disclosed herein provide duplex sequencing methods that effectively suppress errors in situations when signals of valid sequences of interest are low, such as samples with low allele frequencies.

Unique molecular indices (UMIs) enable the usage of information from multiple reads to suppress sequencing noise. UMIs, along with contextual information such as alignment positions, allow us to trace the origin of each read to a specific original DNA molecule. Given multiple reads that were produced by the same DNA molecule, computational approaches can be used to separate actual variants (i.e. variants biologically present in the original DNA molecules) from variants artificially introduced via sequencing error. Variants can include, but are not limited to, insertions, deletions, multi-nucleotide variants, single-nucleotide variants, and structural variants. Using this information, we can infer the true sequence of the DNA molecules. We refer to this computational methodology as read collapsing. This error-reduction technology has several important applications. In the context of cell-free DNA analysis, important variants often occur at extremely low frequencies (i.e. <1%); thus their signal can be drowned out by sequencing errors. UMI-based noise reduction allows us to much more accurately call these low-frequency variants. UMIs and read collapsing can also help identify PCR duplicates in high-coverage data, enabling more accurate variant frequency measurements.

In some implementations, random UMIs are used, in which a random sequence was attached to DNA molecules, and those random sequences were used as UMI barcodes. However, using a set of purposefully designed nonrandom UMIs allowed for simpler manufacturing in some implementations. As this approach is non-random, the UMIs are referred to as non-random UMIs (NRUMIs). In some implemenations, a set of NRUMIs consists of uniform-length sequences (e.g., n=6 nucleotides long). Due to the A-tailing process by which these NRUMI molecules are ligated to DNA molecules, the $7^{th}$ (n+1) read is invariably a thymine (T). This uniformity may cause a degradation in read quality that propagates throughout read cycles downstream of this base. This effect is illustrated in FIG. 2C.

Although this issue may be less prominent in non-patterned flow cells sequenced using 4 dyes, its severity is likely to magnify on patterned flows cells sequenced using 2 dyes, as base calling inherently becomes more challenging. In some implementations, a novel process is used to generate NRUMI sets of mixed lengths, uniquely identifying such variable length NRUMIs (vNRUMIs), and correcting errors within these vNRUMIs. It offers diversity in generating and distinguishing DNA barcodes of heterogeneous length. Experimental results show that the vNRUMI method is more robust (i.e. more capable of correcting sequencing errors) than conventional solutions.

In some implementations, a greedy algorithm is used for iteratively constructing vNRUMI sets. At each iteration, it picks a sequence from a pool of vNRUMI candidates such that the chosen sequence maximizes the minimum Levenshtein distance between itself and any vNRUMI that has already been chosen. If multiple sequences share the maximal value of this metric, the algorithm chooses one such sequence randomly, preferring sequences of shorter length. This distance metric is required to be at least 3 to enforce good error correction within the resultant vNRUMI set; if this condition cannot be satisfied, the process stops adding new vNRUMIs to the set, and return the set as is. This entire process can be repeated to generate different sets of vNRUMIs with similar characteristics.

Adapters can include physical UMIs that allow one to determine which strand of the DNA fragment the reads are derived from. Some embodiments take advantage of this to determine a first consensus sequence for reads derived from one strand of the DNA fragment, and a second consensus sequence for the complementary strand. In many embodiments, a consensus sequence includes the nucleotides detected in all or a majority of reads while excluding nucleotides appearing in few of the reads. Different criteria of consensus may be implemented. The process of combining reads based on UMIs or alignment locations to obtain a consensus sequence is also referred to as "collapsing" the reads. Using physical UMIs, virtual UMIs, and/or alignment locations, one can determine that reads for the first and second consensus sequences are derived from the same double stranded fragment. Therefore, in some embodiments, a third consensus sequence is determined using the first and second consensus sequences obtained for the same DNA molecule/fragment, with the third consensus sequence including nucleotides common for the first and second consensus sequences while excluding those inconsistent between the two. In alternative implementations, only one consensus sequence is directly obtained by collapsing all reads derived from both strands of the same fragment, instead of by comparing the two consensus sequences obtained from the two strands. Finally, the sequence of the fragment may be determined from the third or the only one consensus sequence, which includes base pairs that are consistent across reads derived from both strands of the fragment.

In some embodiments, the method combines different types of indices to determine the source polynucleotide on which reads are derived. For example, the method may use both physical and virtual UMIs to identify reads deriving from a single DNA molecule. By using a second form of UMI, in addition to the physical UMI, the physical UMIs may be shorter than when only physical UMIs are used to determine the source polynucleotide. This approach has minimal impact on library prep performance, and does not require extra sequencing read length.

Applications of the disclosed methods include:
Error suppression for somatic mutation detection. For example, detection of mutation with less than 0.1% allele frequency is highly critical in liquid biopsy of circulating tumor DNA.
Correct prephasing, phasing and other sequencing errors to achieve high quality long reads (e.g., 1×1000 bp)
Decrease cycle time for fixed read length, and correct increased phasing and prephasing by this method.
Use UMIs on both sides of fragment to create virtual long paired end reads. For example, stitch a 2×500 read by doing 500+50 on duplicates.
Quantifying or counting nucleic acid fragments relating to a sequence of interest.

Workflow for Sequencing Nucleic Acid Fragments Using UMIs

FIG. 1A is a flow chart illustrating an example workflow 100 for using UMIs to sequence nucleic acid fragments. Workflow 100 is illustrative of only some implementations. It is understood that some implementations employ workflows with additional operations not illustrated here, while other implementations may skip some of the operations illustrated here. For instance, some implementations do not require operation 102 and/or operation 104. Also, workflow 100 is employed for whole genome sequencing. In some implementations involving targeted sequencing, operational steps to hybridize and enrich certain regions may be applied between operation 110 and 112.

Operation 102 provides fragments of double-stranded DNA. The DNA fragments may be obtained by fragmenting genomic DNA, collecting naturally fragmented DNA (e.g., cfDNA or ctDNA), or synthesizing DNA fragments from RNA, for example. In some implementations, to synthesize DNA fragments from RNA, messenger RNA or noncoding RNA is first purified using polyA selection or depletion of ribosomal RNA, then the selected mRNA is chemically fragmented and converted into single-stranded cDNA using random hexamer priming. A complementary strand of the cDNA is generated to create a double-stranded cDNA that is ready for library construction. To obtain double stranded DNA fragments from genomic DNA (gDNA), input gDNA is fragmented, e.g., by hydrodynamic shearing, nebulization, enzymatic fragmentation, etc., to generate fragments of appropriate lengths, e.g., about 1000 bp, 800 bp, 500, or 200 bp. For instance, nebulization can break up DNA into pieces less than 800 bp in short periods of time. This process generates double-stranded DNA fragments.

In some implementations, fragmented or damaged DNA may be processed without requiring additional fragmentation. For instance, formalin-fixed, paraffin embedded (FFPE) DNA or certain cfDNA are sometimes fragmented enough that no additional fragmentation step is required.

Figure 1B:
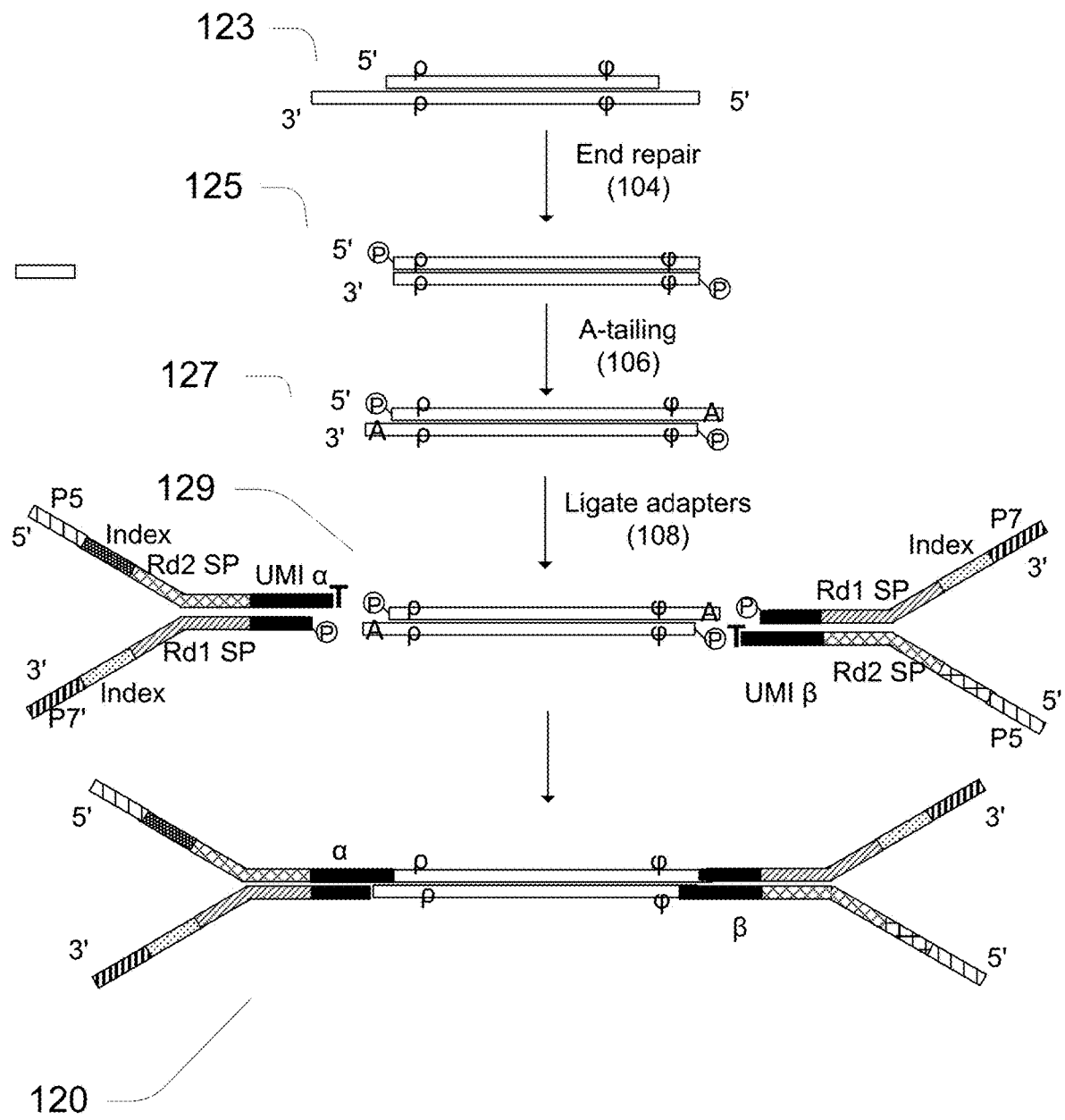
FIG. 1B shows a DNA fragment/molecule and the adapters employed in initial steps of workflow shown in FIG. 1A.

FIG. 1B shows a DNA fragment/molecule and the adapters employed in initial steps of workflow 100 in FIG. 1A.

Although only one double-stranded fragment is illustrated in FIG. 1B, thousands to millions of fragments of a sample can be prepared simultaneously in the workflow. DNA fragmentation by physical methods produces heterogeneous ends, comprising a mixture of 3' overhangs, 5' overhangs, and blunt ends. The overhangs will be of varying lengths and ends may or may not be phosphorylated. An example of the double-stranded DNA fragments obtained from fragmenting genomic DNA of operation 102 is shown as fragment 123 in FIG. 1B.

Fragment 123 has both a 3' overhang on the left end and a 5' overhang shown on the right end, and is marked with ρ and φ, indicating two sequences in the fragment that may be used as virtual UMIs in some implementations, which, when used alone or combined with physical UMIs of an adapter to be ligated to the fragment, may uniquely identify the fragment. UMIs are uniquely associated with a single DNA fragment in a sample including a source polynucleotide and its complementary strand. A physical UMI is a sequence of an oligonucleotide linked to the source polynucleotide, its complementary strand, or a polynucleotide derived from the source polynucleotide. A virtual UMI is a sequence of an oligonucleotide within the source polynucleotide, its complementary strand, or a polynucleotide derived from the source polynucleotide. Within this scheme, one may also refer to the physical UMI as an extrinsic or exogenous UMI, and the virtual UMI as an intrinsic or endogenous UMI.

The two sequences ρ and φ actually each refer to two complementary sequences at the same genomic site, but for simplicity sake, they are indicated on only one strand in some of the double-stranded fragments shown herein. Virtual UMIs such as ρ and φ can be used at a later step of the workflow to help identify reads originating from one or both strands of the single DNA source fragment. With the reads so identified, they can be collapsed to obtain a consensus sequence.

If DNA fragments are produced by physical methods, workflow 100 proceeds to perform end repair operation 104, which produces blunt-end fragments having 5'-phosphorylated ends. In some implementations, this step converts the overhangs resulting from fragmentation into blunt ends using T4 DNA polymerase and Klenow enzyme. The 3' to 5' exonuclease activity of these enzymes removes 3' overhangs and the 5' to 3' polymerase activity fills in the 5' overhangs. In addition, T4 polynucleotide kinase in this reaction phosphorylates the 5' ends of the DNA fragments. The fragment 125 in FIG. 1B is an example of an end-repaired, blunt-end product.

After end repairing, workflow 100 proceeds to operation 106 to adenylate 3' ends of the fragments, which is also referred to as A-tailing or dA-tailing, because a single dATP is added to the 3' ends of the blunt fragments to prevent them from ligating to one another during the adapter ligation reaction. Double stranded molecule 127 of FIG. 1B shows an A-tailed fragment having blunt ends with 3'-dA overhangs and 5'-phosphate ends. A single 'T' nucleotide on the 3' end of each of the two sequencing adapters as seen in item 129 of FIG. 1B provides an overhang complementary to the 3'-dA overhang on each end of the insert for ligating the two adapters to the insert.

After adenylating 3' ends, workflow 100 proceeds to operation 108 to ligate partially double stranded adapters to both ends of the fragments. In some implementations, the adapters used in a reaction include different physical UMIs to associate sequence reads to a single source polynucleotide, which may be a single- or double-stranded DNA fragment. In some implementations, a set of physical UMIs used in a reaction are random UMIs. In some implementations, the set of physical UMIs used in the reaction are nonrandom UMIs (NRUMIs). In some implementations, the set of physical UMIs used in the reaction are variable-length, nonrandom UMIs (vNRUMIs).

Item 129 of FIG. 1B illustrates two adapters to be ligated to the double-stranded fragment that includes two virtual UMIs ρ and φ near the ends of the fragment. These adapters are illustrated based on the sequencing adapters of the Illumina platform, as various implementations may use Illumina's NGS platform to obtain reads and detect sequence of interest. The adapter shown on the left includes the physical UMI α in its double-stranded region, while the adapter on the right includes physical UMI β in its double-stranded region. On the strand having the 5' denatured end, from 5' to 3' direction, adapters have a P5 sequence, an index sequence, a read 2 primer sequence, and a physical UMI (α or β). On the strand having the 3' denatured end, from 3' to 5' direction, the adapters have a P7' sequence, an index sequence, a read 1 primer sequence, and the physical UMI (α or β).

The P5 and P7' oligonucleotides are complementary to the amplification primers bound to the surface of flow cells of Illumina sequencing platform. In some implementations, the index sequence provides a means to keep track of the source of a sample, thereby allowing multiplexing of multiple samples on the sequencing platform. Other designs of adapters and sequencing platforms may be used in various implementations. Adapters and sequencing technology are further described in sections that follow.

The reaction depicted in FIG. 1B adds distinct sequences to the genomic fragment. A ligation product 120 from the same fragment described above is illustrated in FIG. 1B. This ligation product 120 has the physical UMI α, the virtual UMI ρ, the virtual UMI φ, and physical UMI β on its top strand, in the 5'-3' direction. The ligation product also has the physical UMI β, the virtual UMI φ, the virtual UMI ρ, and the physical UMI α on its bottom strand, in the 5'-3' direction. This disclosure embodies methods using sequencing technologies and adapters other than those provided by Illumina.

Figure 2A:
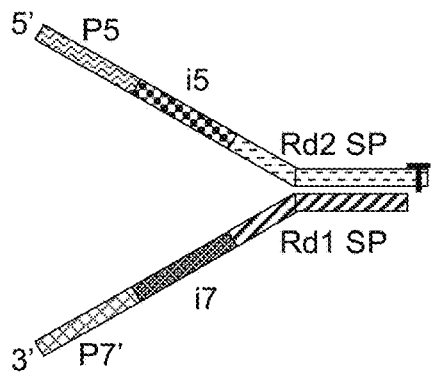
FIG. 2A schematically illustrates five different adapter designs that may be adopted in the various implementations.
Figure 2A:
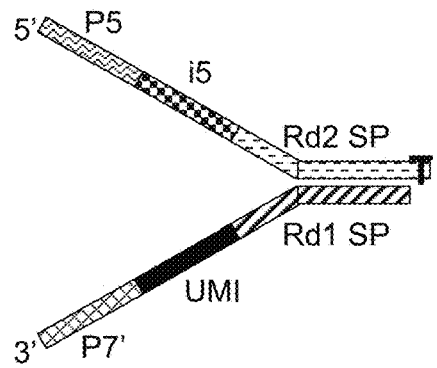
Figure 2A:
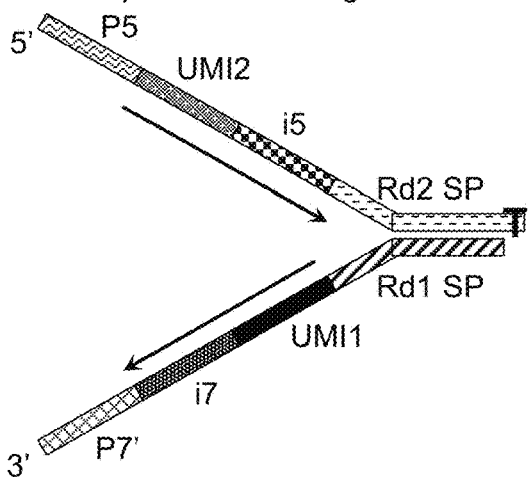
Figure 2A:
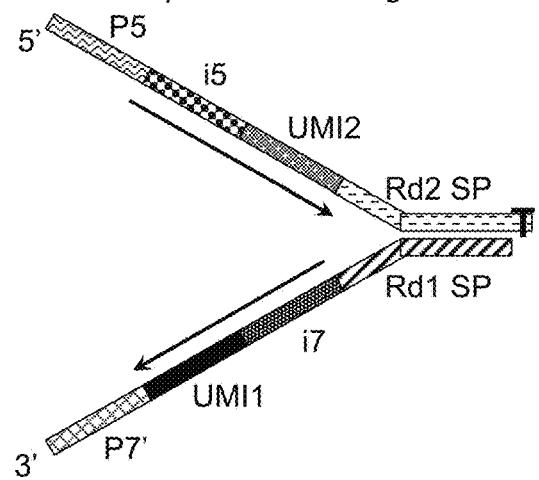
Figure 2A:
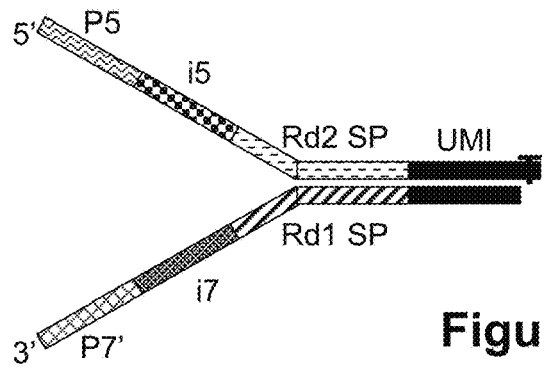
Figure 2A:
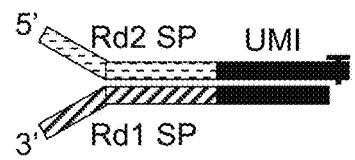

Although the example adapters here have the physical UMIs on the double-stranded regions of the adapters, some implementations use adapters having physical UMIs on the single stranded regions, such as adapters (i) and (iv) in FIG. 2A.

In some implementations, the products of this ligation reaction are purified and/or size-selected by agarose gel electrophoresis or magnetic beads. Size-selected DNA is then PCR amplified to enrich for fragments that have adapters on both ends. See block 110. As mentioned above, in some implementations, operations to hybridize and enrich certain regions of the DNA fragments may be applied to target the regions for sequencing.

Workflow 100 then proceeds to cluster amplify PCR products, e.g., on an Illumina platform. See operation 112. By clustering of the PCR products, libraries can be pooled for multiplexing, e.g., with up to 12 samples per lane, using different index sequences on the adapters to keep track of different samples.

After cluster amplification, sequencing reads can be obtained through sequencing by synthesis on the Illumina platform. See operation 114. Although the adapters and the sequencing process described here are based on the Illumina platform, others sequencing technologies, especially NGS methods may be used instead of or in addition to the Illumina platform.

The workflow 100 can collapse reads having the same physical UMI(s) and/or the same virtual UMI(s) into one or more groups, thereby obtaining one or more consensus sequences. See operation 116. In some implementations, the physical UMIs are random UMIs. In some implementations, the physical UMIs are non-random UMIs. In some implementations, the physical UMIs are variable length, random UMIs. In some implementations, the physical UMIs are variable-length, nonrandom UMIs (vNRUMIs). A consensus sequence includes nucleotide bases that are consistent or meet a consensus criterion across reads in a collapsed group. In some implementations, physical UMIs alone may provide sufficient information to tag DNA fragments to collapse reads. Such implementations would require a large enough number of physical UMIs to uniquely tag the DNA fragments. In other implementations, physical UMIs, virtual UMIs, and position information may be combined in various ways to collapse reads to obtain consensus sequences for determining the sequence of a fragment or at least a portion thereof. In some implementations, physical UMIs are combined with virtual UMIs to collapse reads. In other implementations, physical UMIs and read positions are combined to collapse reads. Read position information may be obtained by various techniques using different position measurements, e.g., genomic coordinates of the reads, positions on a reference sequence, or chromosomal positions. In further implementations, physical UMIs, virtual UMIs, and read positions are combined to collapse reads.

Finally, workflow 100 uses the one or more consensus sequences to determine the sequence of the nucleic acid fragment from the sample. See operation 118. This may involve determining the nucleic acid fragment's sequence as the third consensus sequence or the single consensus sequence described above.

In a particular implementation that includes operations similar to operations 108-119, a method for sequencing nucleic acid molecules from a sample using nonrandom UMIs involves the following: (a) applying adapters to DNA fragments in the sample to obtain DNA-adapter products, where each adapter comprises a NRUMI, and where NRUMIs of the adapters have at least two different molecular lengths, forming a set of vNRUMIs; (b) amplifying the DNA-adapter products to obtain a plurality of amplified polynucleotides; (c) sequencing the plurality of amplified polynucleotides, thereby obtaining a plurality of reads associated with the set of vNRUMIs; (d) identifying, among the plurality of reads, reads associated with a same vNRUMI; and (e) determining a sequence of a DNA fragment in the sample using the reads associated with the same vNRUMI.

In another implementation, variable-length, random UMIs are used for sequencing nucleic acid molecules. The method includes: (a) applying adapters to DNA fragments in the sample to obtain DNA-adapter products, wherein each adapter comprises a unique molecular index (UMI), and wherein unique molecular indices (UMIs) of the adapters have at least two different molecular lengths and form a set of variable-length unique molecular indices (vUMIs); (b) amplifying the DNA-adapter products to obtain a plurality of amplified polynucleotides; (c) sequencing the plurality of amplified polynucleotides, thereby obtaining a plurality of reads associated with the set of vUMIs; and (d) identifying, among the plurality of reads, reads associated with a same variable-length, nonrandom unique molecular index (vUMI). Some implementations further includes determining a sequence of a DNA fragment in the sample using the reads associated with the same vUMI.

In some implementations, the UMIs used for sequencing nucleic acid fragments may be fixed-length random UMIs, fixed-length nonrandom UMIs, variable-length random UMIs, variable-length nonrandom UMIs, or any combination thereof. In these implementations, the method for sequencing nucleic acid fragments includes: (a) applying adapters to DNA fragments in the sample to obtain DNA-adapter products, wherein each adapter comprises a unique molecular index (UMI) in a set of unique molecular indices (UMIs); (b) amplifying the DNA-adapter products to obtain a plurality of amplified polynucleotides; (c) sequencing the plurality of amplified polynucleotides, thereby obtaining a plurality of reads associated with the set of UMIs; (d) obtaining, for each read of the plurality of reads, alignment scores with respect to the set of UMIs, each alignment score indicating similarity between a subsequence of a read and a UMI; (e) identifying, among the plurality of reads, reads associated with a same UMI using the alignment scores; and (e) determining a sequence of a DNA fragment in the sample using the reads associated with the same UMI. In some implementations, the alignment scores are based on matches of nucleotides and edits of nucleotides between the subsequence of the read and the UMI. In some implementations, each alignment score penalizes mismatches at the beginning of a sequence but does not penalize mismatches at the end of the sequence.

In some implementations, the sequence reads are paired-end reads. Each read either includes a nonrandom UMI or is associated with a nonrandom UMI through a paired-end read. In some implementations, the read lengths are shorter than the DNA fragments or shorter than one half of the fragments' length. In such cases, the complete sequence of the whole fragment is sometimes not determined. Rather, the two ends of the fragment are determined. For example, a DNA fragment may be 500 bp long, from which two 100 bp paired-end reads can be derived. In this example, the 100 bases at each end of the fragment can be determined, and the 300 bp in the middle of the fragment may not be determined without using information of other reads. In some implementations, if the two pair-end reads are long enough to overlap, the complete sequence of the whole fragment may be determined from the two reads. For instance, see the example described in association with FIG. 5.

In some implementations, an adaptor has a duplex nonrandom UMI in the double stranded region of the adaptor, and each read includes a first nonrandom UMI on one end and a second nonrandom UMI on the other end.

Method for Sequencing Nucleic Acid Fragments Using vNRUMIs

In some implementations vNRUMIs are incorporated into adaptors for sequencing DNA fragments. The vNRUMIs provide a mechanism for suppressing different types of errors occur in a workflow such as the one described above. Some of the errors may occur in the sample processing phase such as deletions, additions, and substitutions in sample processing. Other errors may occur in the sequencing phase. Some errors may be located in bases derived from the DNA fragments, other errors may be located in bases corresponding to the UMIs in the adapters.

Some implementations provide a novel process for detecting and correcting errors in vNRUMIs and in sequence reads. On a high level, given a read containing a (potentially misread) vNRUMI and its downstream bases, the process uses a global-local (glocal) hybrid alignment strategy to match the first few bases of the read to a known vNRUMI, thereby obtaining alignment scores between prefix sequences of the read and the known vNRUMI. A vNRUMI having a highest glocal alignment score is determined to be the vNRUMI associated with the read, which provides a mechanism to collapse the read with other reads associated with the same vNRUMI, thereby correcting errors. Pseudocode for obtaining glocal alignment scores and matching vNRUMIs using the glocal alignment scores in some implementations is provided as follows.

```
algorithm glocal:
    input: DNA sequences x and y
           Integral scores for (match, mismatch, gap), default
           (1, -1, -1)
    output: z, an integral value which increases with sequence similarity
    scores = numeric matrix of length(x)+1 rows and length(y)+1
    columns
    for i from 0 to length(x), inclusive:
        scores[i][0] = i
    for j from 0 to length(y), inclusive:
        scores[0][j] = j
    for i from 1 to length(x), inclusive:
        for j from 1 to length(y), inclusive:
            cost = match if x[i-1]==y[j-1], otherwise cost =
            mismatch
            set scores[i][j] to maximum of:
                scores[i-1][j-1] + cost
                scores[i-1][j] + gap
                scores[i][j-1] + gap
    z = maximum across last row and last column of scores matrix
    return z
algorithm match_vNRUMI:
    input: set X containing all valid/non-mutated vNRUMIs
           sequence Q, a possibly mutated vNRUMI and
           downstream bases
    output: m₁ the set of most likely vNRUMI matches
            m₂ the set of second most like vNRUMI matches
    potentialLengths = unique lengths of all sequences in X
    matchScores = list containing potential matches for Q and their
    corresponding
        scores
    n = maximum length of any sequence in set X
    subseq = first n bases in Q
    for every sequence S in X:
        record glocal(S, subseq) score in matchScores, along with
        the sequence S itself
    m₁ = sequences in X with highest observed glocal scores
    m₂ = sequences in X with second highest observed glocal scores
    return m₁ and m₂
```

It is worth noting that the usage of an unconventional distance metric. Across other comparable methodologies for DNA barcodes, most adopt heuristics quantifying edit distance, namely Levenshtein distance, Hamming distance, or derivatives thereof. Conceptually, an alignment score provides a similar metric of sequence similarity, but with one key difference: it counts matches in addition to changes. A match-aware heuristic underlies some of the advantages in some implementation of variable length NRUMIs.

In some implementations, neither a traditional Needleman-Wunsch global alignment nor a traditional Smith-Waterman local alignment method is used, but a novel hybrid approach is used. Namely, the alignment uses a Needleman-Wunsch approach in the beginning of the alignment, penalizing edits there, but leverages concepts from Smith Waterman local alignment at the end of the alignment by not penalizing end edits. In this sense, the current alignment approach encompass both a global and a local component, and is therefore referred to as a glocal alignment approach. In the event of an insertion or deletion mistake in sequencing, the alignment would shift considerably. This global approach would not penalize that single event any more than one would penalize a single point mutation. Allowing for trailing gaps allows us to accomplish this.

The glocal alignment approach has the ability to work with barcode pools of heterogeneous length, a distinguishing feature from conventional methodologies.

Figure 1C:
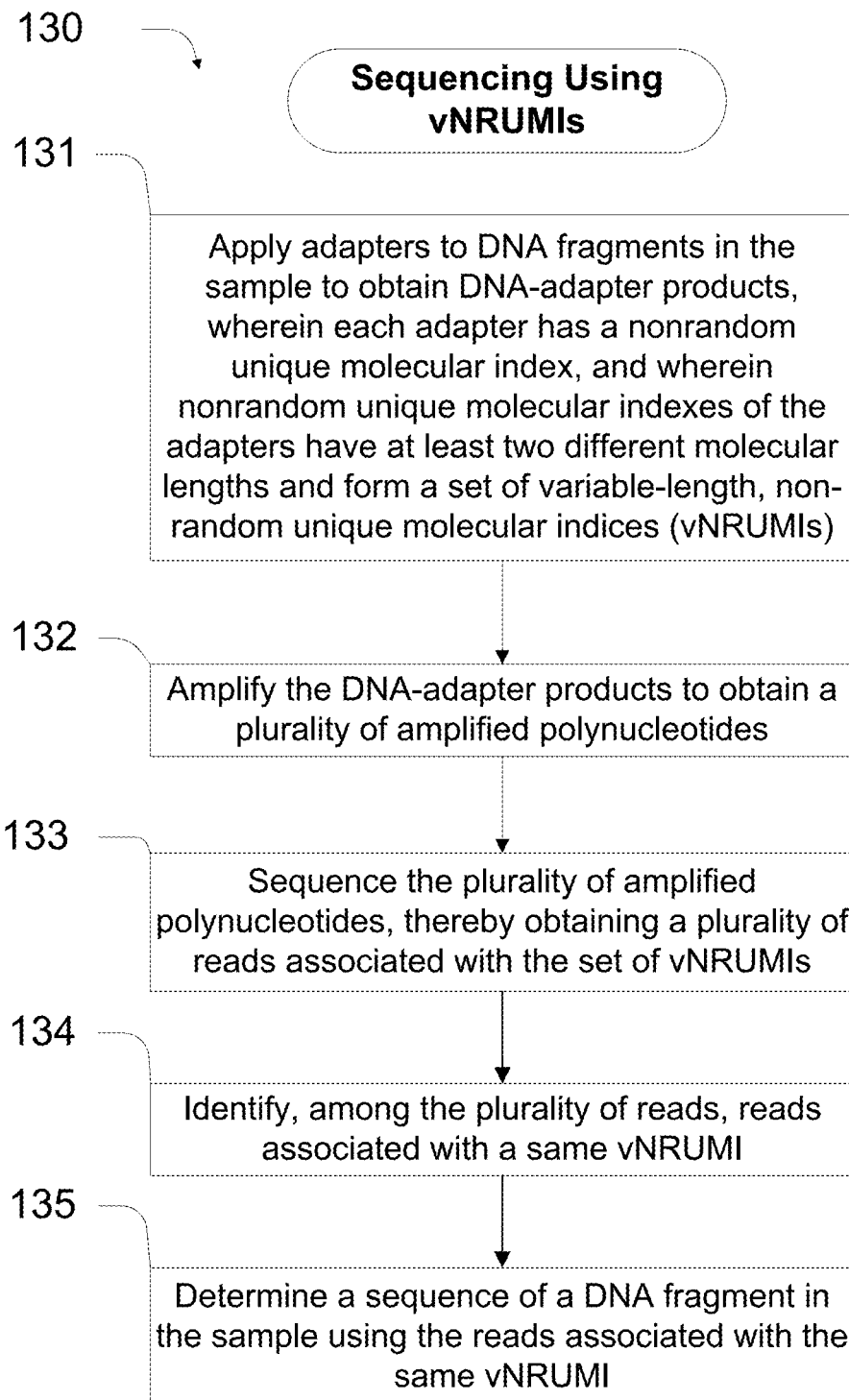
FIG. 1C is a block diagram showing a process for sequencing DNA fragments using vNRUMIs to suppress errors.

In identifying matches, some implementations can return multiple vNRUMI matches as the "best" when there are ties. Although the pseudocode above only reflects best and second best returned sets, some implementations has the ability to return more than just two sets of vNRUMIs, such as a second best set, a third best set, a fourth best set, etc. By providing more information of good matches, the process may better correct for errors by collapsing reads associated with one or more candidate matches of vNRUMIs. FIG. 1C is a block diagram showing a process for sequencing DNA fragments using vNRUMIs to suppress errors occurring in the DNA fragments and errors in the UMIs that are used to label the source molecules of the DNA fragments. Process 130 starts by applying adapters to DNA fragments in a sample to obtain DNA-adapter products. See block 131. Each adapter on the adapters has a nonrandom unique molecular index. The nonrandom unique molecular indices of the adapters have at least two different molecular lengths and form a set of variable-length, nonrandom molecular indices (vNRUMIs).

In some implementations, an adapter is attached, ligated, inserted, incorporated, or otherwise linked to each end of the DNA fragments. In some implementations, the sample containing the DNA fragments is a blood sample. In some implementations the DNA fragments contain cell-free DNA fragments. In some implementations, the DNA fragments include cell-free DNA originating from a tumor, and the sequence of the DNA fragments in the sample is indicative of the tumor.

Process 130 proceeds by amplifying the DNA-adapter products to obtain a plurality of amplified polynucleotides. See block 132. Process 130 further involves sequencing the plurality of amplified polynucleotides, thereby obtaining a plurality of reads associated with the set of vNRUMIs. See block 133. Moreover, process 130 involves identifying reads associated with a same vNRUMI from among the plurality of reads. See block 134. Finally, process 130 includes determining a sequence of DNA fragment in the sample using the reads associated with the same vNRUMI.

As mentioned above, process 130 illustrated in FIG. 1C provides a method for sequencing DNA fragments using vNRUMIs. Process 130 starts by applying adapters to DNA fragments of the sample to obtain DNA-adapter products (block 131). Process 130 also involves amplifying the DNA-adapter products to obtain a plurality of amplified polynucleotides (block 132); sequencing the quality of amplified polynucleotides, thereby obtaining a plurality of reads associated with the set of vNRUMIs (block 133); identifying reads associated with the same vNRUMI (block 134); and determining a sequence of DNA fragments in the sample using the reads associated with the same vNRUMI (block 135). The sample may be a blood sample, a plasma sample, a tissue sample, or one of the samples as described elsewhere herein. In some implementations, the adapters applied in step 131 can be obtained from a process such as process 140 illustrated in FIG. 1D.

In some implementations, the vNRUMIs of the adapters have at least two different molecular lengths. In some implementations, the set of vNRUMIs have two different molecular lengths. In some implementations, the vNRUMIs have six or seven nucleotides. In some implementations, the vNRUMIs have more than two different molecular lengths, such as having three, four, five, six, seven, eight, nine, ten, twenty, or more different molecular lengths. In some implementations, the molecular lengths are chosen from the range 4-100. In some implementations, the molecular lengths are chosen from the range 4-20. In some implementations, the molecular lengths are chosen from the range 5-15.

In some implementations, the set of vNRUMIs includes no more than about 10,000 different vNRUMIs. In some implementations, the set of vNRUMIs includes no more than about 1000 different vNRUMIs. In some implementations, the set of vNRUMIs includes no more than about 200 different vNRUMIs.

In some implementations, step 134 of identifying reads associated with the same vNRUMI involves obtaining, for each read of the plurality of reads, alignment scores with respect to the vNRUMIs. Each alignment score indicates similarity between a subsequence of the read and a vNRUMI. The subsequence is in a region of the read in which nucleotides derived from the vNRUMI are likely located. In other words, in some implementations, the subsequence includes the first nucleotides in a region where the vNRUMI is expected to be located. In some implementations, the subsequence's size equals to the size of the largest vNRUMI in the set of vNRUMIs.

In some implementations, the alignment scores are based on matches and mismatches/edits of nucleotides between the subsequence of the read and the vNRUMI. In some implementations, the edits of nucleotides include substitutions, additions, and deletions of nucleotides. In some implementations, the alignment score penalizes edits at the beginning of a sequence (e.g., a subsequence of a read or a reference sequence of a vNRUMI) but does not penalize edits at the end of the sequence. The alignment score reflects the similarity between the subsequence of the read and the vNRUMI reference sequence.

In some implementations, obtaining an alignment score between the read and the vNRUMI involves: (a) calculating an alignment score between the vNRUMI and each one of all possible prefix sequences of the subsequence of the read; (b) calculating an alignment score between the subsequence of the read and each one of all possible prefix sequences of the vNRUMI; and (c) obtaining a largest alignment score among the alignment scores calculated in (a) and (b) as the alignment score between the read and the vNRUMI.

In some implementations, the subsequence of the read has a length that is equal to the length of the longest vNRUMI in the set of vNRUMIs.

In some implementations, identifying the reads associated with the same vNRUMI includes selecting, for each read of the plurality of reads, at least one vNRUMI from the set of vNRUMIs based on the alignment scores; and associating each read of the plurality of reads with the at least one vNRUMI selected for the read. In some implementations, selecting the at least one vNRUMI from the set of vNRUMIs includes selecting a vNRUMI having the highest alignment score among the set of vNRUMI.

In some implementations, one vNRUMI is identified for a highest alignment score. In some implementations, two or more vNRUMIs are identified for the highest alignment score. In such case, contextual information about the reads may be used to select one of the two or more vNRUMIs that should be associated with the reads to determine the sequence in the DNA fragments. For instance, the total number of reads identified for one vNRUMI can be compared to the total number of reads identified for another vNRUMI, and a higher total number determines the one vNRUMI that should be used to indicate the source of the DNA fragment. In another example, sequence information of reads or locations of reads on a reference sequence may be used to select one of the identified vNRUMI associated with the reads, the selected vNRUMI being used to determine the source of the sequence reads.

In some implementations, two or more of the highest alignment scores may be used to identify two or more vNRUMIs to indicate potential source of any fragment. Contextual information may be used as mentioned above to determine which one of the vNRUMIs indicates the actual source of the DNA fragment.

FIG. 1E shows examples of how a subsequence of a read or a query sequence (Q) can be compared to two reference sequences in the vNRUMI set γ={S1,S2}={AACTTC, CGCTTTCG}. The query sequence Q includes the first seven nucleotides from the read sequence where reads are expected to be derived from the vNRUMIs.

The query sequence Q includes seven nucleotides GTCT-TCG. Q has the same length as the longest vNRUMI in the vNRUMI set γ. Alignment score table 150 shows the alignment scores for prefix sequences of Q and S1. For instance, cell 151 shows the alignment score for the prefix sequence of Q (GTCTTC) and the complete sequence of S1 (AACTTC). The alignment score takes into account the number of matches between the two sequences, as well as the number of edits between the two sequences. For each matching nucleotide, the score goes up by 1; for each deletion, addition, or substitution, the score goes down by 1. In contrast, a Levenshtein distance is an edit distance, which does not account for the number of matches between two sequences, but only accounting for the number of additions, deletions, and substitutions.

Comparing prefix sequence of Q (GTCTTC) and S1 (AACTTC) nucleotide by nucleotide, there is a mismatch between G and A, a mismatch between T and A, a match between C and C, a match between T and T, a match between T and T, and a match between C and C. Therefore, the alignment score for the two prefix sequences is 2 as shown in cell 151. The alignment score does not penalize the end of sequence Q having a nucleotide G.

In alignment score table 150 the rightmost column with the bolded alignment scores show the alignment scores between all possible subsequences of the query sequence Q and all possible prefix sequences of reference vNRUMI sequence S1. The bottom row of the alignment score table 150 shows the alignment scores between the complete sequence S1 and all possible prefix sequences of Q. In various implementations, the highest alignment score in the rightmost column and the bottom row is selected as the glocal alignment score between Q and S1. In this example, cell 151 has the highest value, which is determined as the glocal alignment score between Q and S1, or g(Q,S1).

The highest alignment score across the bottom row and rightmost column is used as a glocal alignment score between two sequences. Different string operations are weighted equally in the alignment scores illustrated here. An alignment score is calculated as: # of matches−# of insertions−# of deletions−# of substitutions=# match−Levenshtein distance. However, as mentioned above, in some implementations, different string operations may be weighted differently in calculating an alignment score. For example, in some implementations (not shown in FIG. 1E), an alignment score may be calculated as: # of matches×5−# of insertions×4−# of deletions×4−# of substitutions×6, or using other weight values.

In the implementations described above, the alignment scores combine the effects of matches and edits in a linearly fashion, namely by addition and/or subtraction. In other implementations, the alignment scores can combine the effects of matches and edits in non-linear manner such as by multiplication or logarithmic operations.

The alignment scores in the rightmost column and the bottom row indicate similarity between prefix sequences on the one hand and a complete sequence on the other. When the beginning of a prefix sequence does not match the beginning of the complete sequence, the alignment score is penalized. In this sense, the alignment score has a global component. On the other hand, when the end of a prefix sequence does not match the end of the complete sequence, the sequence alignment score is not penalized. In this sense, the alignment score has a local component. Therefore, the alignment scores in the rightmost column and the bottom row can be described as "glocal" alignment scores. The glocal alignment score between Q and S1 is the largest alignment score in the rightmost row and the bottom column, which is 2 and in cell 151 for Q prefix sequence GTCTTC and S1 (AACTTC).

The Levenshtein distance between Q prefix sequence GTCTTC and S1 (AACTTC) is also 2, because there is a mismatch between G and A, a mismatch between T and A, and four matches for CTTC. For these two sequences, the Levenshtein distance and the alignment score are the same.

Compared to a glocal alignment score, a pure global alignment score requires the complete sequence Q on the one hand and the complete sequence S1 on the other hand, which is the alignment score in the lower right-hand corner of table 150.

Table 152 in FIG. 1E shows the alignment scores for query sequence Q and reference sequence S2 (CGCTTCG). The highest alignment score in the rightmost column and the bottom row is in cell 153, having a value of 4. It is the glocal alignment score between Q and S2, or g(Q,S2). The Levenshtein distance between Q and S2 is identical to the Levenshtein distance between Q and S1, because there are two mismatches between the two sequences in both comparisons. However, g(Q,S2) is larger than g(Q,S1), because there are more matching nucleotides between Q and S2 than between Q and S1. Namely, the glocal alignment scores account for not only edits of nucleotides (as Levenshtein distance does), but also matches of nucleotides between sequences.

FIG. 1E illustrates that the glocal alignment score can provide better error correction than Levenshtein distance or edit distance, because Levenshtein distance accounts for only number of edits in the sequence, while the glocal alignment score accounts for both number of edits and number of matches between the sequences. FIG. 1F provides an example illustrating that the glocal alignment score can provide better error suppression than the global alignment score, because the glocal alignment score does not over-penalize mismatches due to insertion, deletion, or substitution at the end of the sequence.

The example in FIG. 1F uses a different set of vNRUMI sequences, γ={S1,S2}={TTGTGAC,GGCCAT}. In the sample processing process S1 is used to label a DNA molecule. This molecule's sequence is $m_0$=TTGTGACTNNNN (SEQ ID NO: 1). During sequencing, a single insertion error occurs and the sequence GCA is inserted into $m_0$, creating $m_1$=TTGGCATGACTNNNN (SEQ ID NO: 2). To correct for this error and recover the proper UMI for this sequence, a process takes the first 7 base pairs as the query sequence, Q=TTGGCAT. The process compares Q with each sequence in γ.

An alignment score table 160 for g(Q, S1) is obtained and shown in FIG. 1F. And similarly, an alignment score table 163 is obtained for g(Q, S2).

If a global alignment scheme instead of a glocal alignment score is used, the score at the bottom right corner in cells 161 and 164 would be used, which have a value of 2 in both cases. An optimal alignment of Q (TTGGCAT) and S1 (TTGTGAC) is by aligning TTG-GCAT with TTGTG-AC, where dashes represent insertions or gaps. This alignment involves 5 matches, 2 insertions, and 1 substitution, providing an alignment score 5-2-1=2. An optimal alignment of Q (TTGGCAT) and S2 (GGCCAT) is by aligning TTGGC-AT and -GGCCAT. This alignment involves 5 matches and 3 insertions, providing an alignment score 5-3=2. Using a global alignment score, one cannot conclusively determine which one of S1 and S2 is more likely to be the actual vNRUMI.

However, by using a glocal alignment scheme, which uses the maximum value across the last row and column, the process obtains an alignment score of 3 for Q's prefix sequence TTGGC and S1 (TTGTGAC), which becomes the glocal score of S1 and is higher than the glocal score for S2 (2). As such, the process can correctly associate Q with S1.

Returning to FIG. 1C, step 135 involves determining a sequence of DNA fragment in the sample using the reads associated with the same vNRUMI. In some implementations, determining the sequence of the DNA fragment involves collapsing reads associated with the same vNRUMI to obtain a consensus sequence, which can be achieved as further described hereinafter. In some implementations, the consensus sequence is based on quality scores of the reads, as well the sequence of the reads. Additionally or alternatively, other contextual information such as the position of the reads may be used to determine the consensus sequence.

In some implementations, determining the sequence of the DNA fragment also involves identifying reads having the same position or similar positions in a reference sequence. The method then determine the sequence of the DNA fragment using reads that are associated with the same vNRUMI and have the same position or similar positions in the reference sequence.

In some implementations, determining the sequence of the DNA fragment involves identifying, among the reads associated with the same vNRUMI, reads sharing a common virtual UMI or similar virtual UMIs, where the common virtual UMIs is found in the DNA fragment. The method also involves determining the sequence of DNA fragment using only reads that are both associated with the same vNRUMI and sharing the same virtual UMIs or cellular virtual UMIs.

In some implementations, the sequencing adapters having vNRUMIs can be prepared by a process depicted in FIG. 1D and further described hereinafter.

UMI Design

Physical UMIs

In some implementations of the adapters described above, the physical UMIs in the adapters include random UMIs. In some implementations, each random UMI is different from every other random UMI applied to DNA fragments. In other words, the random UMIs are randomly selected without replacement from a set of UMIs including all possible different UMIs given the sequence length(s). In other implementations, the random UMIs are randomly selected with replacement. In these implementations, two adapters may have the same UMI due to random chance.

In some implementations, the physical UMIs used in a process are a set of NRUMIs that are selected from a pool of candidate sequences using a greedy approach that maximizes the differences among the selected UMIs as further described hereinafter. In some implementations, the NRU- MIs have variable or heterogeneous molecular lengths, forming a set of vNRUMIs. In some implementations, the pool of candidate sequences are filtered to remove certain sequences before being provided to select a set of UMIs used in a reaction or process.

Random UMIs provide a larger number of unique UMIs than nonrandom UMIs of the same sequence length. In other words, random UMIs are more likely to be unique than nonrandom UMIs. However, in some implementations, nonrandom UMIs may be easier to manufacture or have higher conversion efficiency. When nonrandom UMIs are combined with other information such as sequence position and virtual UMI, they can provide an efficient mechanism to index the source molecules of DNA fragments.

Construction of vNRUMIs

Figure 1D:
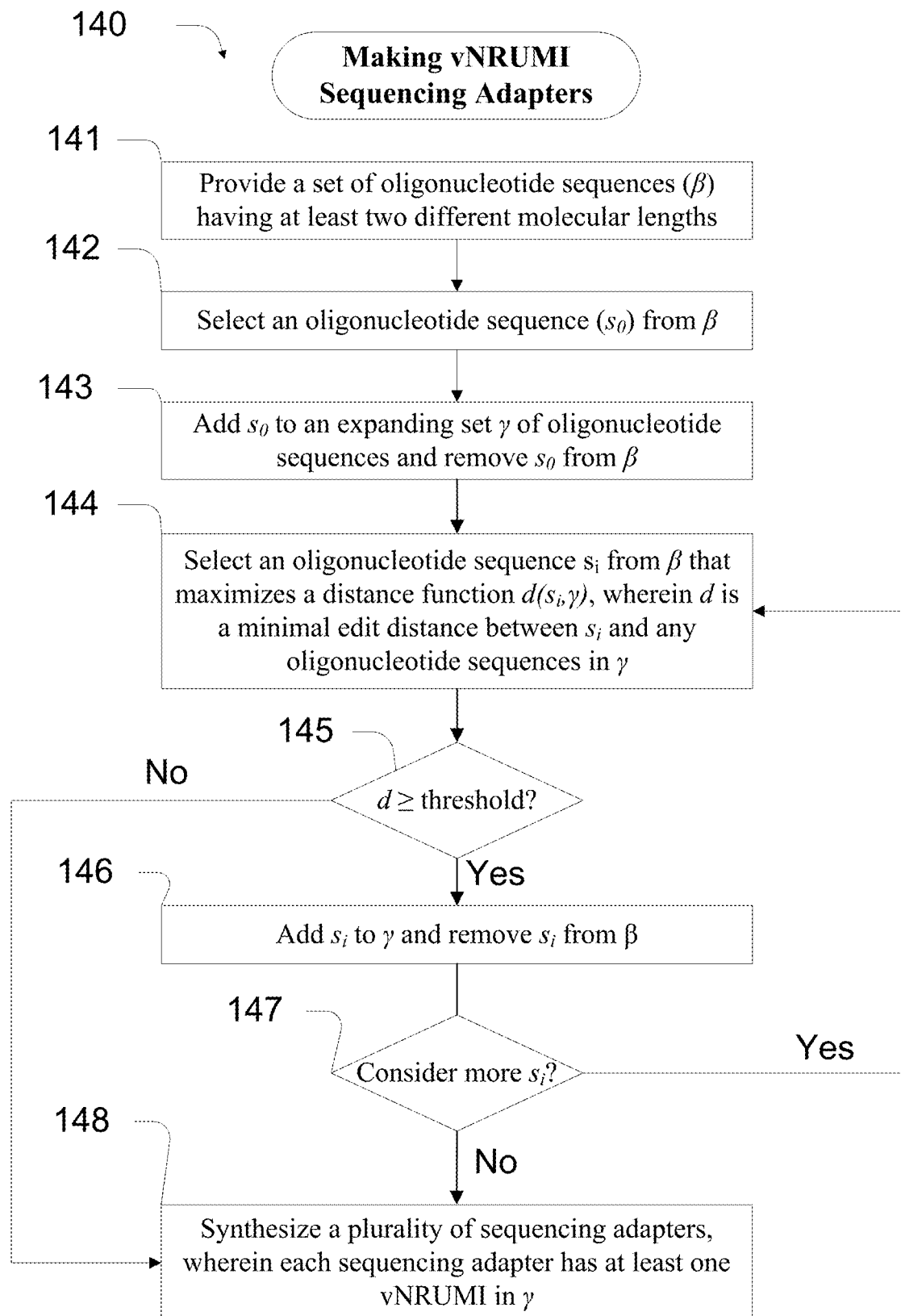
FIG. 1D illustrates a process 140 for making sequencing adapters having vNRUMIs.

In some implementations, the sequencing adapters having vNRUMIs can be prepared by a greedy approach depicted in FIG. 1D. The process involves (a) providing a set of oligonucleotide sequences having two different molecular lengths; and (b) selecting a subset of oligonucleotide sequences from the set of oligonucleotide sequences, all edit distances between oligonucleotide sequences in the subset meeting a threshold value. The subset of oligonucleotide sequences forms a set of vNRUMIs. The method also involves (c) synthesizing a plurality of sequencing adapters, the sequencing adapter having a double-stranded hybridized region, a single-stranded 5' end, a single-stranded 3' end as depicted in FIG. 2A, and at least one vNRUMI in the set of vNRUMIs.

FIG. 1D illustrates a process 140 for making sequencing adapters having vNRUMIs. Process 140 starts by providing a set of oligonucleotide sequences ($\beta$) having at least two different molecular lengths. See block 141.

In various implementations, nonrandom UMIs are prepared considering various factors, including but not limited to, means for detecting errors within the UMI sequences, conversion efficiency, assay compatibility, GC content, homopolymers, and manufacturing considerations.

In some implementations, before operation 141, some of the oligonucleotide sequences are removed from the complete set of all possible permutations of nucleotides given the specific molecular lengths of the set of vNRUMIs. For example, if the vNRUMIs have molecular lengths of six and seven nucleotides, all possible permutations of sequences include a complete pool of $4^6+4^7=20480$ sequences. Certain oligonucleotide sequences are removed from the pool to provide the set of oligonucleotide sequences $\beta$.

In some implementations, oligonucleotide sequences having three or more consecutive identical bases are removed from the pool to provide the set $\beta$. In some implementations, oligonucleotide sequences having a combined number of guanine and cytosine (G and C) bases less than two are removed. In some implementations, oligonucleotide sequences having a combined number of guanine and cytosine bases more than four are removed. In some implementations, oligonucleotide sequences having the same base at the last two positions of the sequence are removed. The sequence starts from the end opposite from the end attached to the DNA fragments.

In some implementations, oligonucleotide sequences having a subsequence matching the 3' end of any sequencing primers are removed.

In some implementations, oligonucleotide sequences having a thymine (T) base at the last position of nucleotide sequences are removed. A vNRUMI attached to an A-tail end of a processed nucleic acid fragment will result in a subsequence of a read having the vNRUMI sequence and a T base annealed to the end of the vNRUMI sequence, the T being complementary of the A base on the A-tail. Filtering out candidate sequences having a T base at the last position avoids confusion between such candidate sequences and subsequence of reads derived from any vNRUMIs.

Process 140 proceeds by selecting an oligonucleotide sequence ($S_0$) from $\beta$. See block 142. In some implementations, $S_0$ may be randomly chosen from the set of oligonucleotide sequences.

Process 140 further involves adding $S_0$ to an expanding set $\gamma$ of oligonucleotide sequences and removing $S_0$ from the set $\beta$. See block 143.

Process 140 further involves selecting oligonucleotide sequence $S_i$ from $\beta$, $S_i$ maximizes the distance function $d(S_i, \gamma)$, which is a minimal edit distance between $S_i$ and any oligonucleotide sequence in set $\gamma$. See block 144. In some implementations, the edit distance is Levenshtein distance.

In some implementations, when the sequence is shorter than the maximum length of the vNRUMIs, one or more bases are appended to the end of the sequence when calculating the Levenshtein distance or edit distance. In some implementations, if the sequence is one base shorter than the maximum length of the vNRUMIs, a thymine (T) base is added to the end of the sequence. This T base is added to reflect a T-base overhang at the end of an adapter complementary to the A-base at the end of a DNA fragment that has undergone dA-tailing processing as described herein elsewhere. In some implementations, if the sequence is more than one base shorter than the maximum length of the vNRUMIs, a T-base is added to the end of the sequence, and then one or more random bases are added after the T-base to create a sequence having a molecular length equaling the maximum length of the vNRUMIs. In other words, one can append multiple different combinations of random bases after the T base to create sequences spanning all the possible observed sequences. For example, if the vNRUMIs have lengths 6 and 8, one may obtain four derivations of a 6mer by appending TA, TC, TG, and TT.

Process 140 proceeds to determine whether the distance function $d(S_i, \gamma)$ meet the threshold value. In some implementations, the threshold value may require that the distance function (e.g., a padded Levenshtein distance) is at least 3. If the distance function $d(S_i, \gamma)$ the meets the threshold, the process proceeds to add $S_i$ to the expanding set $\gamma$ and removes $S_i$ from the set $\beta$. See the "Yes" branch of decision 145 and block 146. If the distance function does not meet the threshold value, process 140 does not add $S_i$ to the expanding set $\gamma$, and the process proceeds to synthesize the plurality of sequencing adapters, where each sequencing adapter has at least one vNRUMI in the expanding set $\gamma$. See the no decision branch of 145 pointing to block 148.

After step 146, process 140 further involves a decision operation of whether more sequences from set $\beta$ need to be considered. If so, the process loop back to block 144 to select more oligonucleotide sequences from set $\beta$ that maximizes the distance function. Various factors may be considered to determine whether more sequences need to be further considered from the set $\beta$. For instance, in some implementations, when the desired number of sequences has been obtained, the process no longer needs to consider more sequences from the sequence set data.

When it is decided that no more sequences needs to be considered, process 140 proceeds to synthesize the plurality of sequencing adapters where each adapter has at least one vNRUMI in sequence set $\gamma$. See the no decision branch of operation 147 pointing to operation 148. In some implementations, each sequencing adapter has the vNRUMI on one strand of the sequencing adapters. In some implementations, sequencing adapters having any of the forms illustrated in FIG. 2A are synthesized in operation 148. In some implementations, each sequencing adapter has only one vNRUMI. In some implementations, each adapter has a vNRUMI on each strand of the sequencing adapters. In some implementations, each sequencing adapter has a vNRUMI on each strand of the sequencing adapter in the double stranded, hybridized region.

In some implementations, the process can be implemented by the pseudocode below.

```
algorithm vNRUMI_dist:
    input: Set S of vNRUMI sequences, query sequence Q
    output: Integer d representing the distance from Q to S
    let distances be a list of all encountered distances
    for each sequence s in S:
            if length(s) < maximum length of any sequence in S:
                add a "T" to s
            if length(Q) < maximum length of any sequence in S:
                add a "T" to Q
            add Levenshtein(s, Q) to distances
            return minimum value in distances
algorithm generate_vNRUMI_set:
    input: set X containing potential/candidate vNRUMI sequences
            integer N indicating number of desired vNRUMIs in
            set
    output: set Y containing a set of at most N vNRUMIs
    pick a random element from X, add it to Y, remove it from X
    while number of sequences in Y < N:
            store vNRUMI_dist for every candidate in X against Y
            Z = maximum vNRUMI_dist encountered
            if Z >= 3:
                    S = set of all sequences that have a vNRUMI_dist of
                    Z
                    S_chosen = pick a random item from S, prefer shorter
                    sequences
                    add S_chosen Y, remove it from X
            else:
                    return Y
    return Y
```

Next a toy example is presented to illustrate how vNRUMIs can be obtained according to the process and algorithm described above. The toy example shows how vNRUMIs can be produced from a pool of five candidate sequences, which are then used to map observed sequence reads. Note that since this is a toy example over a significantly smaller sequence space than we would use/encounter in practice, not every aspect of the characteristics of the vNRUMIs can be addressed.

In this toy example, the process aims to construct a set of 3 vNRUMI sequences starting from a set 6mers and 7mers (but resulted in only 2 vNRUMI sequences). For simplicity, assume that the entire space of possible 6mers and 7mers consists of the following 5 sequences:

AACTTC

AACTTCA

AGCTTCG

CGCTTCG

CGCTTC

Note that it is assumed all of these 5 sequences have passed any biochemical filters that are implemented. At a very high level, this algorithm subsets the input sequence pool while maximizing an edit distance (a Levenshtein distance) between sequences chosen. It does this using a greedy approach—at each iteration it picks a sequence that maximizes the distance function. The distance function, in this case, is the minimum edit distance between the sequence to be added and any sequence already in the set. This can be mathematically expressed as follows:

$$d(s,\gamma)=\min(\text{levenshtein}(s,x) \forall x \in \gamma)$$

In the below example, the vNRUMI set (n=3) being constructed will be denoted as $\gamma$, the set of input candidate sequences will be denoted as $\beta$.

$\gamma = \{ \ \}, \ \beta = \{AACTTC, AACTTCA, AGCTTCG, CGCTTCG, CGCTTC\}$

Since there are no sequences in $\gamma$, the distance function d is undefined for each of the 5 sequences. In the event of a tie for best choice, we always pick one of the tied candidates randomly, preferring shorter sequences. Here, the example picks the timer sequence AACTTC. It adds the sequence to $\gamma$ and removes it from the pool of candidate sequences.

$\gamma = \{AACTTC\}, \ \beta = \{AACTTCA, AGCTTCG, CGCTTCG, CGCTTC\}$

The distance metric $d(s,\gamma) \forall s \in \beta$ is calculated.

$d(AACTTCA,\gamma)=1$, as it only takes one edit (addition of an A) to get from the single element in $\gamma$ to AACTTCA, and therefore the distance function is 1.

$d(AGCTTCG,\gamma)=2$, as it takes two edits to go from this sequence to the sequence already in $\gamma$.

$d(CGCTTCG,\gamma)=3$, as it takes three edits to go from this sequence to the sequence already in $\gamma$.

$d(CGCTTC,\gamma)=2$, as the sequence in comparison is a sixmer, in some implementations, a "T" base is added to the end of it to simulate the annealing process, in which a T base complementary to the "A" tail is annealed to the adapter sequence. The rationale is that when practitioners try to identify the NRUMI later, they will be considering both the first sixmer and the first sevenmer. By adding this T base, it is ensured that when looking at the sevenmer, it still isn't too close to any other NRUMI. Comparing CGCTTCT to AACTTC, there are two edits required.

Since the maximum distance function is 3, produced by the sequence CGCTTCG, and this distance passes our minimum threshold (of 3), the process adds CGCTTCG to $\gamma$ and removes it from $\beta$.

$\gamma = \{AACTTC, CGCTTCG\}, \ \beta = \{AACTTCA, AGCTTCG, CGCTTC\}$

Next the process proceeds to calculate the distance metric $d(s,\gamma) \forall s \in \beta$ since there are less than the desired number (3) of sequences in the vNRUMI set.

$d(AACTTCA,\gamma)=1$. As calculated in the previous step, the edit distance between this sequence and the first vNRUMI sequence, $s_1$=AACTTC, is 1. The edit distance between this sequence and the second vNRUMI sequence, $s_2$=CGCTTCG, is 3. The distance function takes the minimum of all the edit distances between the query sequence and any existing sequence, and min(3,1)=1 so the distance function is 1.

$d(AGCTTCG,\gamma)=1$. As calculated in the previous step, the edit distance between this sequence and $s_1$ is 2. The edit distance between this sequence and $s_2$ is 1. Therefore, the distance function is the smaller of 2 and 1 (which is 1).

d(CGCTTC,γ)=1. As previous, the process appends a T to this sequence to make it CGCTTCT. The distance between the lengthened query and $s_1$ is 2, as previously determined. The distance between the lengthened query and $s_2$ is 1, so the distance function is 1.

Having calculated all the distance functions for all candidate sequences, none of them satisfy our invariant requirement of an edit distance of at least 3. This requirement makes it highly unlikely for random mutations to mutate one vNRUMI sequence into something resembling another. Therefore, we return this set of 2 vNRUMI sequences, γ={AACTTC, CGCTTCG}. It is noted that the two vNRUMI sequences are the same as the S1 and S2 in FIG. 1E described above, and they could be associated with reads to determine the source segment of the reads as described with reference to FIG. 1E.

Virtual UMIs

Turning to virtual UMI, those Virtual UMIs that are defined at, or with respect to, the end positions of source DNA molecules can uniquely or nearly uniquely define individual source DNA molecules when the locations of the end positions are generally random as with some fragmentation procedures and with naturally occurring cfDNA. When the sample contains relatively few source DNA molecules, the virtual UMIs can themselves uniquely identify individual source DNA molecules. Using a combination of two virtual UMIs, each associated with a different end of a source DNA molecule, increases the likelihood that virtual UMIs alone can uniquely identify source DNA molecules. Of course, even in situations where one or two virtual UMIs cannot alone uniquely identify source DNA molecules, the combination of such virtual UMIs with one or more physical UMIs may succeed.

If two reads are derived from the same DNA fragment, two subsequences having the same base pairs will also have the same relative location in the reads. On the contrary, if two reads are derived from two different DNA fragments, it is unlikely that two subsequences having the same base pairs have the exact same relative location in the reads. Therefore, if two or more subsequences from two or more reads have the same base pairs and the same relative location on the two or more reads, it can be inferred that the two or more reads are derived from the same fragment.

In some implementations, subsequences at or near the ends of a DNA fragment are used as virtual UMIs. This design choice has some practical advantages. First, the relative locations of these subsequences on the reads are easily ascertained, as they are at or near the beginning of the reads and the system need not use an offset to find the virtual UMI. Furthermore, since the base pairs at the ends of the fragments are first sequenced, those base pairs are available even if the reads are relatively short. Moreover, base pairs determined earlier in a long read have lower sequencing error rate than those determined later. In other implementations, however, subsequences located away from the ends of the reads can be used as virtual UMIs, but their relative positions on the reads may need to be ascertained to infer that the reads are obtained from the same fragment.

One or more subsequences in a read may be used as virtual UMIs. In some implementations, two subsequences, each tracked from a different end of the source DNA molecule, are used as virtual UMIs. In various implementations, virtual UMIs are about 24 base pairs or shorter, about 20 base pairs or shorter, about 15 base pairs or shorter, about 10 base pairs or shorter, about 9 base pairs or shorter, about 8 base pairs or shorter, about 7 base pairs or shorter, or about 6 base pairs or shorter. In some implementations, virtual UMIs are about 6 to 10 base pairs. In other implementations, virtual UMIs are about 6 to 24 base pairs.

Adapters

In addition to the adapter design described in the example workflow 100 with reference to FIG. 1A above, other designs of adapters may be used in various implementations of the methods and systems disclosed herein. FIG. 2A schematically illustrates five different designs of adapter with UMI(s) that may be adopted in the various implementations.

FIG. 2A(i) shows a standard Illumina TruSeq® dual index adapter. The adapter is partially double-stranded and is formed by annealing two oligonucleotides corresponding to the two strands. The two strands have a number of complementary base pairs (e.g., 12-17 bp) that allow the two oligonucleotides to anneal at the end to be ligated with a dsDNA fragment. A dsDNA fragment to be ligated on both ends for pair-end reads is also referred to as an insert. Other base pairs are not complementary on the two strands, resulting in a fork-shaped adapter having two floppy overhangs. In the example of FIG. 2A(i), the complementary base pairs are part of read 2 primer sequence and read 1 primer sequence. Downstream to the read 2 primer sequence is a single nucleotide 3'-T overhang, which provides an overhang complementary to the single nucleotide 3'-A overhang of a dsDNA fragment to be sequenced, which can facilitate hybridization of the two overhangs. The read 1 primer sequence is at the 5' end of the complementary strand, to which a phosphate group is attached. The phosphate group is necessary for ligating the 5' end of the read 1 primer sequence to the 3'-A overhang of the DNA fragment. On the strand having the 5' floppy overhang (the top strand), from 5' to 3' direction, the adapter has a P5 sequence, i5 index sequence, and the read 2 primer sequence. On the strand having the 3' floppy overhang, from 3' to 5' direction, the adapter has a P7' sequence, an i7 index sequence, and the read 1 primer sequence. The P5 and P7' oligonucleotides are complementary to the amplification primers bound to the surface of flow cells of an Illumina sequencing platform. In some implementations, the index sequences provide means to keep track of the source of a sample, thereby allowing multiplexing of multiple samples on the sequencing platform.

FIG. 2A(ii) shows an adapter having a single physical UMI replacing the i7 index region of the standard dual index adapter shown in FIG. 2A(i). This design of the adapter mirrors that shown in the example workflow described above in association with FIG. 1B. In certain embodiments, the physical UMIs α and β are designed to be on only the 5' arm of the double-stranded adapters, resulting in ligation products that have only one physical UMI on each strand. In comparison, physical UMIs incorporated into both strands of the adapters result in ligation products that have two physical UMIs on each strand, doubling the time and cost to sequence the physical UMIs. However, this disclosure embodies methods employing physical UMIs on both strands of the adapters as depicted in FIGS. 2A(iii)-2A(vi), which provide additional information that may be utilized for collapsing different reads to obtain consensus sequences.

In some implementations, the physical UMIs in the adapters include random UMIs. In some implementations, the physical UMIs in the adapters include nonrandom UMIs.

FIG. 2A(iii) shows an adapter having two physical UMIs added to the standard dual index adapter. The physical UMIs shown here may be random UMIs or nonrandom UMIs. The first physical UMI is upstream to the i7 index sequence, and the second physical UMI is upstream to the i5 index sequence. FIG. 2A(iv) shows an adapter also having two physical UMIs added to the standard dual index adapter. The first physical UMI is downstream to the i7 index sequence, and the second physical UMI is downstream to the i5 index sequence. Similarly, the two physical UMIs may be random UMIs or nonrandom UMIs.

An adapter having two physical UMIs on the two arms of the single stranded region, such as those shown in 2A(iii) and 2A(iv), may link two strands of a double stranded DNA fragment, if a priori or a posteriori information associating the two un-complementary physical UMIs is known. For instance, a researcher may know the sequences of UMI 1 and UMI 2 before integrating them to the same adapter in the designed shown in FIG. 2A(iv). This association information may be used to infer that reads having UMI 1 and UMI 2 derive from two strands of the DNA fragment to which the adapter was ligated. Therefore, one may collapse not only reads having the same physical UMI, but also reads having either of the two un-complementary physical UMIs. Interestingly, and as discussed below, a phenomenon referred to as "UMI jumping" may complicate the inference of association among physical UMIs on single-stranded regions of adapters.

The two physical UMIs on the two strands of the adapters in FIG. 2A(iii) and FIG. 2A(iv) are neither located at the same site nor complementary to each other. However, this disclosure embodies methods employing physical UMIs that are at the same site on two strands of the adapter and/or complementary to each other. FIG. 2A(v) shows a duplex adapter in which the two physical UMIs are complementary on a double stranded region at or near the end of the adapter. The two physical UMIs may be random UMIs or nonrandom UMIs. FIG. 2A(vi) shows an adapter similar to but shorter than that of FIG. 2A(v), but it does not include the index sequences or the P5 and P7' sequences complementary to flow cell surface amplification primers. Similarly, the two physical UMIs may be random UMIs or nonrandom UMIs.

Compared to adapters having one or more single-stranded physical UMIs on single-stranded arms, adapters having a double-stranded physical UMI on the double-stranded region can provide a direct link between two strands of a double stranded DNA fragment to which the adapter is ligated, as shown in FIG. 2A(v) and FIG. 2A(vi). Since the two strands of a double-stranded physical UMI are complementary to each other, the association between the two strands of the double-stranded UMI is inherently reflected by the complementary sequences, and can be established without requiring either a priori or a posteriori information. This information may be used to infer that reads having the two complementary sequences of a double-stranded physical UMI of an adapter are derived from the same DNA fragment to which the adapter was ligated, but the two complementary sequences of the physical UMI are ligated to the 3' end on one strand and the 5' end on the other strand of the DNA fragment. Therefore, one may collapse not only reads having the same order of two physical UMI sequences on two ends, but also reads having the reverse order of two complementary sequences on two ends.

In some embodiments, it can be advantageous to employ relatively short physical UMIs because short physical UMIs are easier to incorporate into adapters. Furthermore, shorter physical UMIs are faster and easier to sequence in the amplified fragments. However, as physical UMIs become very short, the total number of different physical UMIs can become less than the number of adapter molecules required for sample processing. In order to provide enough adapters, the same UMI would have to be repeated in two or more adapter molecules. In such a scenario, adapters having the same physical UMIs may be ligated to multiple source DNA molecules. However, these short physical UMIs may provide enough information, when combined with other information such as virtual UMIs and/or alignment locations of reads, to uniquely identify reads as being derived from a particular source polynucleotide or DNA fragment in a sample. This is so because even though the same physical UMI may be ligated to two different fragments, it is unlikely the two different fragments would also happen to have the same alignment locations, or matching subsequences serving as virtual UMIs. So if two reads have the same short physical UMI and the same alignment location (or the same virtual UMI), the two reads are likely derived from the same DNA fragment.

Furthermore, in some implementations, read collapsing is based on two physical UMIs on the two ends of an insert. In such implementations, two very short physical UMIs (e.g., 4 bp) are combined to determine the source of DNA fragments, the combined length of the two physical UMIs providing sufficient information for distinguishing among different fragments.

In various implementations, physical UMIs are about 12 base pairs or shorter, about 11 base pairs or shorter, about 10 base pairs or shorter, about 9 base pairs or shorter, about 8 base pairs or shorter, about 7 base pairs or shorter, about 6 base pairs or shorter, about 5 base pairs or shorter, about 4 base pairs or shorter, or about 3 base pairs or shorter. In some implementations where the physical UMIs are nonrandom UMIs, the UMIs are about 12 base pairs or shorter, about 11 base pairs or shorter, about 10 base pairs or shorter, about 9 base pairs or shorter, about 8 base pairs or shorter, about 7 base pairs or shorter, or about 6 base pairs.

UMI jumping may affect the inference of association among physical UMIs on one arm or both arms of adapters, such as in the adapters of FIGS. 2A(ii)-(iv). It has been observed that when applying these adapters to DNA fragments, amplification products may include a larger number of fragments having unique physical UMIs than the actual number of fragments in the sample.

Furthermore, when adapters having physical UMIs on both arms are applied, amplified fragments having a common physical UMI on one end are supposed to have another common physical UMI on another end. However, sometimes this is not the case. For instance, in the reaction product of one amplification reaction, some fragments may have a first physical UMI and a second physical UMI on their two ends; other fragments may have the second physical UMI and a third physical UMI; yet other fragments may have the first physical UMI and the third physical UMI; still further fragments may have the third physical UMI and a fourth physical UMI, and so on. In this example, the source fragment(s) for these amplified fragments may be difficult to ascertain. Apparently, during the amplification process, the physical UMI may have been "swapped out" by another physical UMI.

One possible approach to addressing this UMI jumping problem considers only fragments sharing both UMIs as deriving from the same source molecule, while fragments sharing only one UMI will be excluded from analysis. However, some of these fragments sharing only one physical UMI may indeed derive from the same molecule as those sharing both physical UMIs. By excluding the fragments sharing just one physical UMI from consideration, useful information may be lost. Another possible approach considers any fragments having one common physical UMI as deriving from the same source molecule. But this approach does not allow combining two physical UMIs on two ends of the fragments for downstream analysis. Furthermore, under either approach, for the example above, fragments sharing the first and second physical UMIs would not be considered to derive from the same source molecule as fragments sharing the third and fourth physical UMIs. This may or may not be true. A third approach may address the UMI jumping problem by using adapters with physical UMIs on both strands of the single-stranded region, such as the adapters in FIGS. 2A(v)-(vi). Further explained below is a description of a hypothetical mechanism underlying UMI jumping.

Figure 2B:
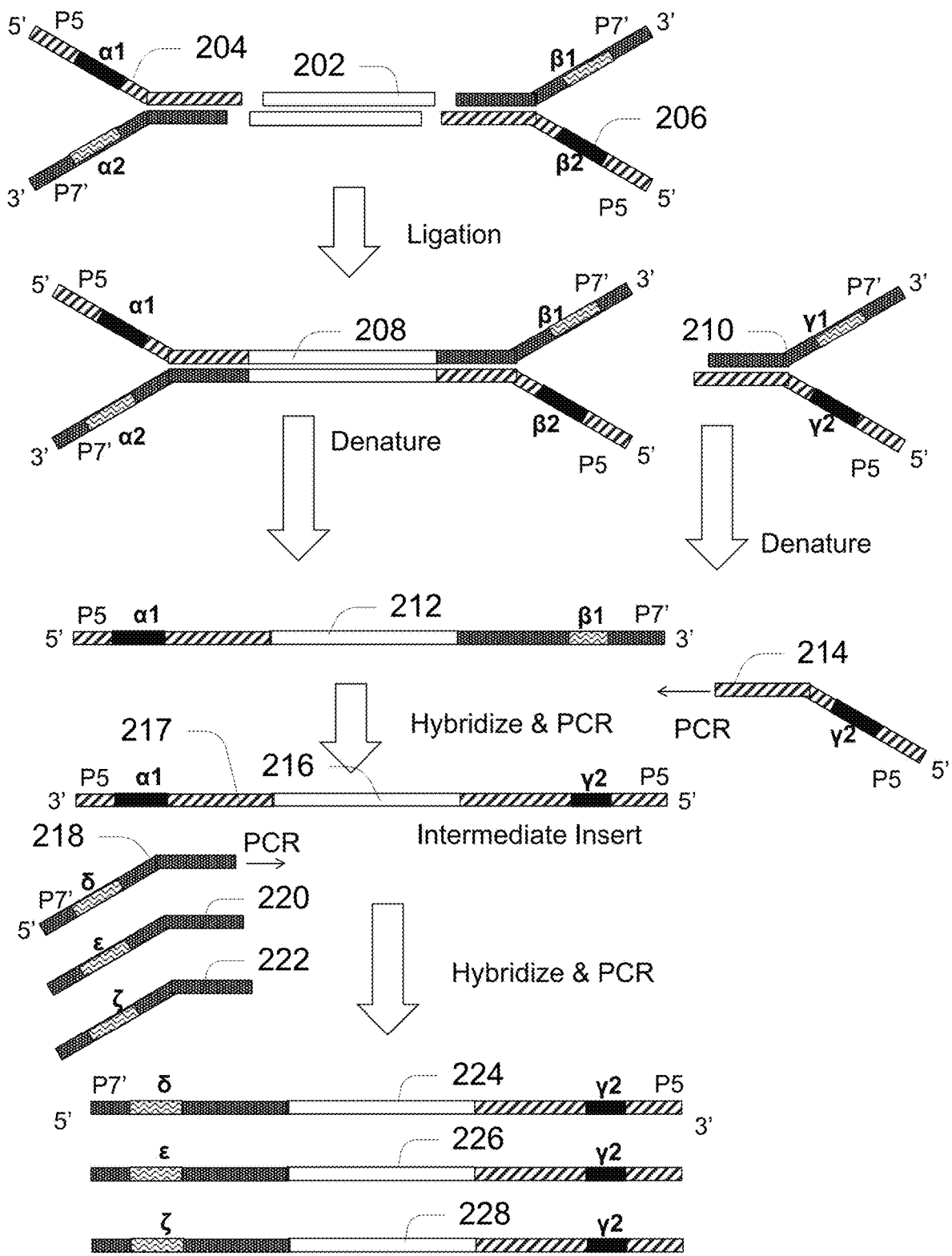
FIG. 2B illustrates a hypothetical process in which UMI jumping occurs in a PCR reaction involving adapters having two physical UMIs on two arms.
Figure 2C:
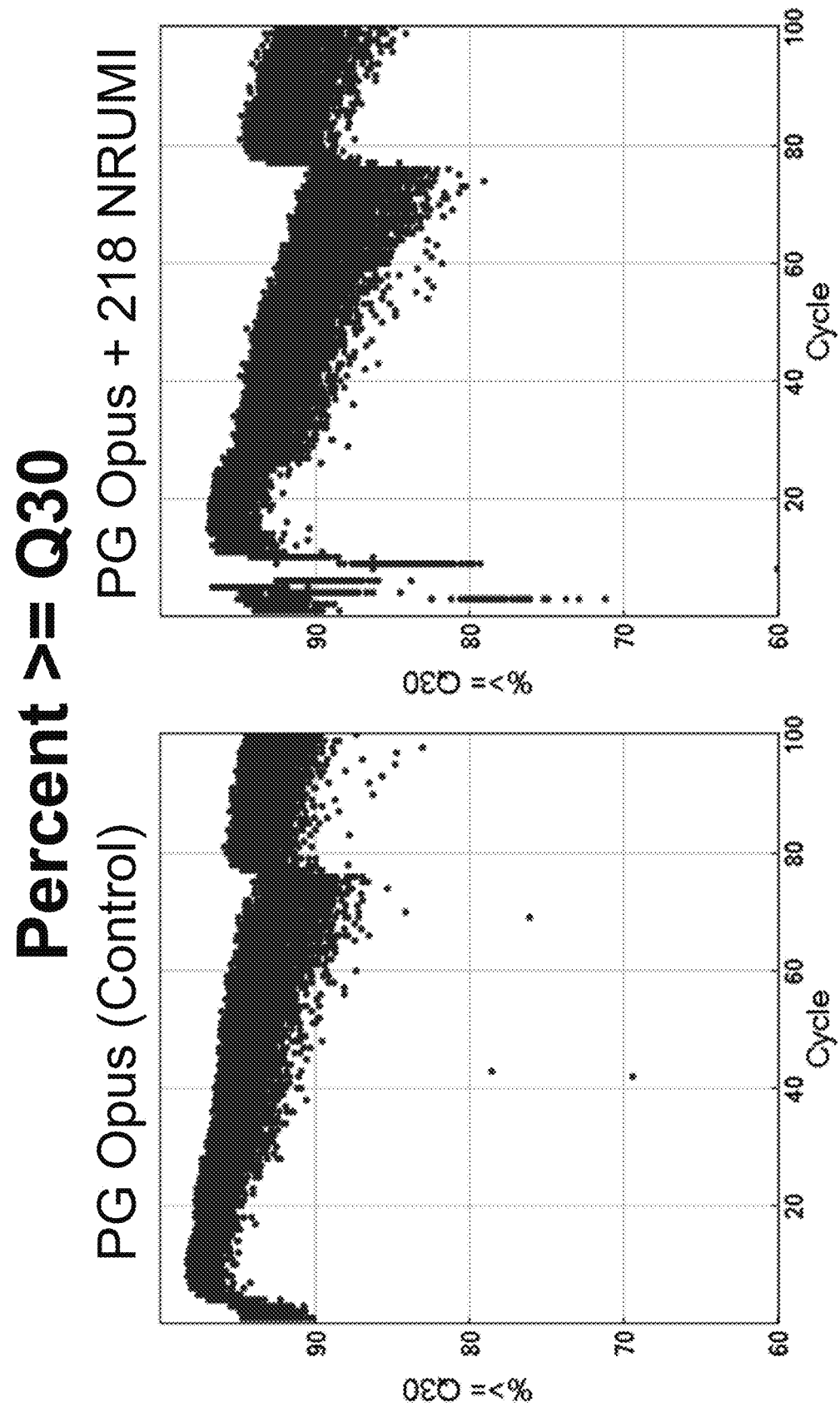
FIG. 2C shows data contrasting the read quality scores of sequence reads using NRUMI versus a control condition.

FIG. 2B illustrates a hypothetical process in which UMI jumping occurs in a PCR reaction involving adapters having physical UMI on both strands in the double-stranded region. The two physical UMIs may be random UMIs or nonrandom UMIs. The actual underlying mechanism of UMI jumping and the hypothetical process described here do not affect the utility of the adapters and methods disclosed herein. The PCR reaction starts by providing at least one double stranded source DNA fragment 202 and adapters 204 and 206. Adapters 204 and 206 are similar to the adapters illustrated in FIG. 2A(iii)-(iv). Adapter 204 has a P5 adapter sequence and an a1 physical UMI on its 5' arm. Adapter 204 also has a P7' adapter sequence and an α2 physical UMI on its 3' arm. Adapter 206 has a P5 adapter sequence and a β2 physical UMI on its 5' arm, and a P7' adapter sequence and a β1 physical UMI on its 3' arm. The process proceeds by ligating adapter 204 and adapter 206 to fragment 202, obtaining ligation product 208. The process proceeds by denaturing ligation product 208, resulting in a single stranded, denatured fragment 212. Meanwhile, a reaction mixture often includes residual adapters at this stage. Because even if the process has already involved removing overabundant adapters such as using Solid Phase Reversible Immobilization (SPRI) beads, some adapters are still left over in the reaction mixture. Such a leftover adapter is illustrated as adapter 210, which is similar to adapter 206, except that adapter 210 has physical UMIs γ1 and γ2 on its 3' and 7' arms, respectively. The denaturing condition producing the denatured fragment 212 also produces a denatured adapter oligonucleotide 214, which has physical UMI γ2 near its P5 adapter sequence.

The single-stranded adapter fragment 214 is then hybridized to the signal stranded DNA fragment 212, and a PCR process extends the single-stranded adapter fragment 214 to produce an intermediate insert 216 that is complementary to DNA fragment 212. During the various cycles of PCR amplification, intermediate adapter fragments 218, 220, and 222 can result from PCR extensions of P7' strands of adapters including different physical UMIs δ, ε, and ζ. The intermediate adapter fragments 218, 220, and 222 all have the P7' sequence on the 5' end, and respectively have physical UMIs δ, ε, and ζ. In ensuing PCR cycles, intermediate adapter fragments 218, 220, and 222 can hybridize to intermediate fragment 216 or its amplicons, because the 3' end of the intermediate adapter fragments 218, 220, and 222 are complementary to region 217 of the intermediate insert 216. PCR extension of the hybridized fragments produces single stranded DNA fragments 224, 226, and 228. DNA Fragments 224, 226, and 228 are labeled with three different physical UMIs (δ, ε, and ζ) on the 5' end, and a physical UMI γ2 on the 3' end, indicating "UMI jumping" where different UMIs are attached to nucleotide sequences derived from the same DNA fragment 202.

In some implementations of the disclosure, using adapters having physical UMIs on both strands of the double-stranded region of the adapters, such as the adapters in FIGS. 2A(v)-(vi), may prevent or reduce UMI jumping. This may be due to the fact that the physical UMIs on one adapter at the double-stranded region are different from physical UMIs on all other adapters. This helps to reduce the complementarity between intermediate adapter oligonucleotides and intermediate fragments, thereby avoiding hybridization such as that shown for intermediate oligonucleotide 222 and intermediate fragment 220, thereby reducing or preventing UMI jumping.

Collapsing Reads and Obtaining Consensus Sequences

In various implementations using UMIs, multiple sequence reads having the same UMI(s) are collapsed to obtain one or more consensus sequences, which are then used to determine the sequence of a source DNA molecule. Multiple distinct reads may be generated from distinct instances of the same source DNA molecule, and these reads may be compared to produce a consensus sequence as described herein. The instances may be generated by amplifying a source DNA molecule prior to sequencing, such that distinct sequencing operations are performed on distinct amplification products, each sharing the source DNA molecule's sequence. Of course, amplification may introduce errors such that the sequences of the distinct amplification products have differences. In the context some sequencing technologies such as Illumina's sequencing-by-synthesis, a source DNA molecule or an amplification product thereof forms a cluster of DNA molecules linked to a region of a flow cell. The molecules of the cluster collectively provide a read. Typically, at least two reads are required to provide a consensus sequence. Sequencing depths of 100, 1000, and 10,000 are examples of sequencing depths useful in the disclosed embodiments for creating consensus reads for low allele frequencies (e.g., about 1% or less).

In some implementations, nucleotides that are consistent across 100% of the reads sharing a UMI or combination of UMIs are included in the consensus sequence. In other implementations, consensus criterion can be lower than 100%. For instance, a 90% consensus criterion may be used, which means that base pairs that exist in 90% or more of the reads in the group are included in the consensus sequence. In various implementations, the consensus criterion may be set at about 30%, about 40%, about 50%, about 60%, about 70%, about 80%, about 90%, about 95%, or about 100%.

Collapsing by Physical UMIs and Virtual UMIs

Multiple techniques may be used to collapse reads that include multiple UMIs. In some implementations, reads sharing a common physical UMI may be collapsed to obtain a consensus sequence. In some implementations, if the common physical UMI is a random UMI, the random UMI may be unique enough to identify a particular source molecule of a DNA fragment in a sample. In other implementations, if the common physical UMI is a nonrandom UMI, the UMI may not be unique enough by itself to identify a particular source molecule. In either case, a physical UMI may be combined with a virtual UMI to provide an index of the source molecule.

Figure 3A:
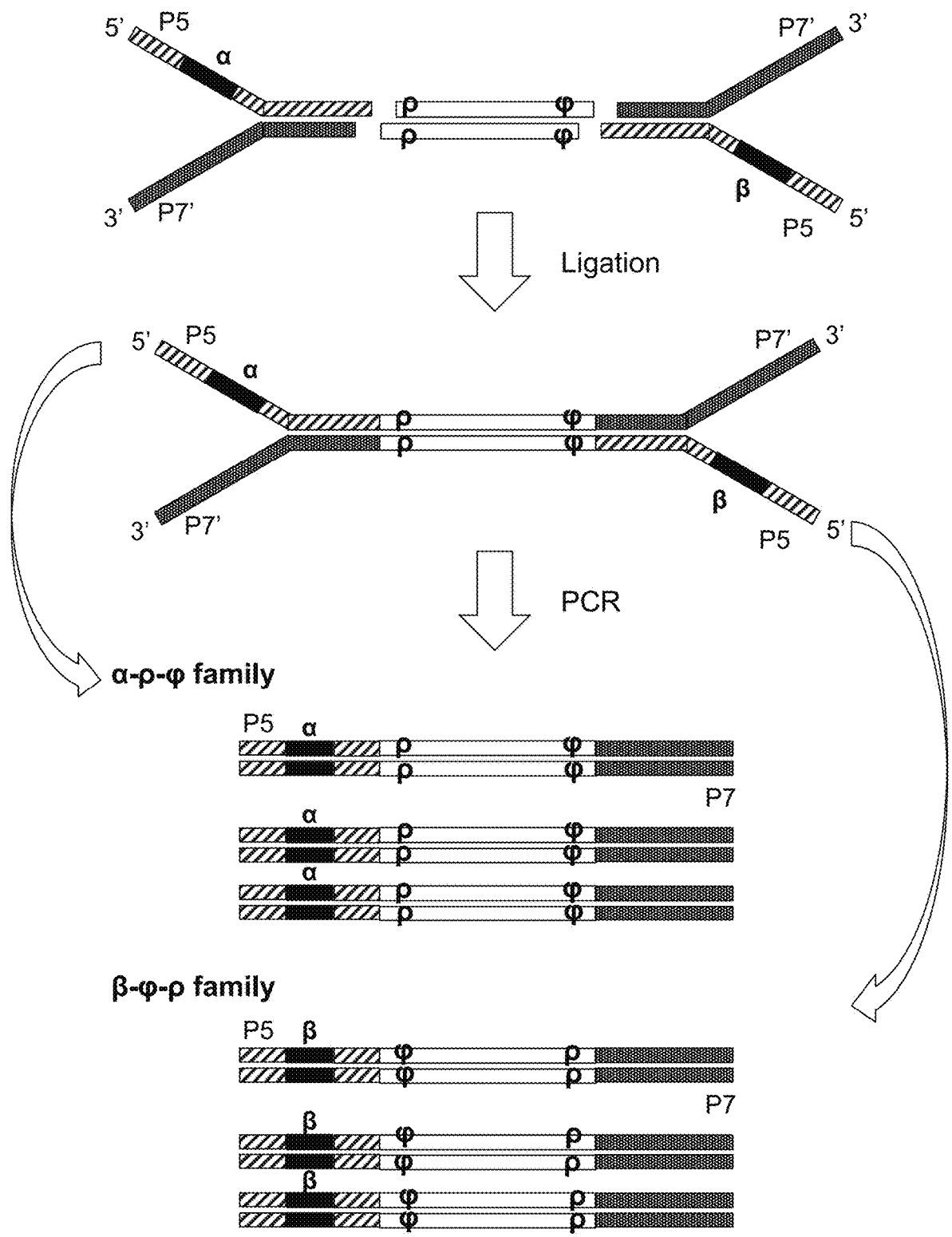
FIGS. 3A and 3B are diagrams showing the materials and reaction products of ligating adapters to double stranded fragments according to some methods disclosed herein.

In the example workflow described above and depicted in FIGS. 1B, 3A, and 4, some reads include α-ρ-φ UMIs, while others include β-φ-ρ UMIs. The physical UMI α produces reads having α. If all adapters used in a workflow have different physical UMIs (e.g., different random UMIs), all reads having α at the adapter region are likely derived from the same strand of the DNA fragment. Similarly the physical UMI β produces reads having β, all of which are derived from the same complementary strand of the DNA fragment. It is therefore useful to collapse all reads including α to obtain one consensus sequence, and to collapse all reads including β to obtain another consensus sequence. This is illustrated as the first level collapsing in FIGS. 4B-4C. Because all reads in a group are derived from the same source polynucleotide in a sample, base pairs included in the consensus sequence likely reflect the true sequence of the source polynucleotide, while a base pair excluded from the consensus sequence likely reflects a variation or error introduced in the workflow.

In addition, the virtual UMIs ρ and φ can provide information to determine that reads including one or both virtual UMIs are derived from the same source DNA fragment. Because virtual UMIs ρ and φ are internal to the source DNA fragments, the exploitation of the virtual UMIs do not add overhead to preparation or sequencing in practice. After obtaining the sequences of the physical UMIs from reads, one or more sub-sequences in the reads may be determined as virtual UMIs. If the virtual UMIs include sufficient base pairs and have the same relative location on reads, they may uniquely identify the reads as having been derived from the source DNA fragment. Therefore, reads having one or both virtual UMIs ρ and φ may be collapsed to obtain a consensus sequence. The combination of virtual UMIs and physical UMIs can provide information to guide a second-level collapsing when only one physical UMI is assigned to a first level consensus sequence of each strand, such as shown in FIG. 3A and FIGS. 4A-4C. However, in some implementations, this second level collapsing using virtual UMIs may be difficult if there are over-abundant input DNA molecules or fragmentation is not randomized.

Figure 3B:
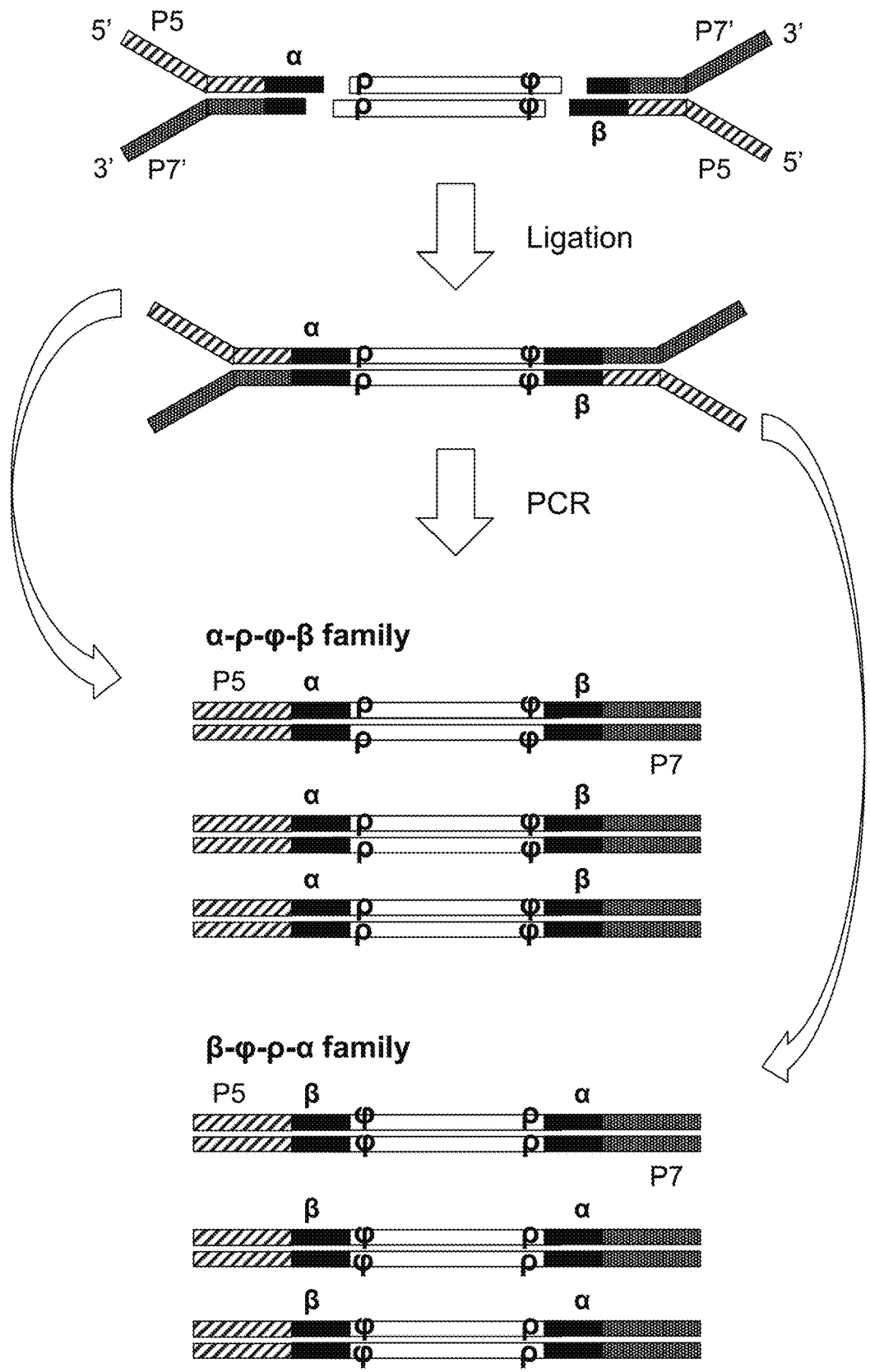
Figure 4A:
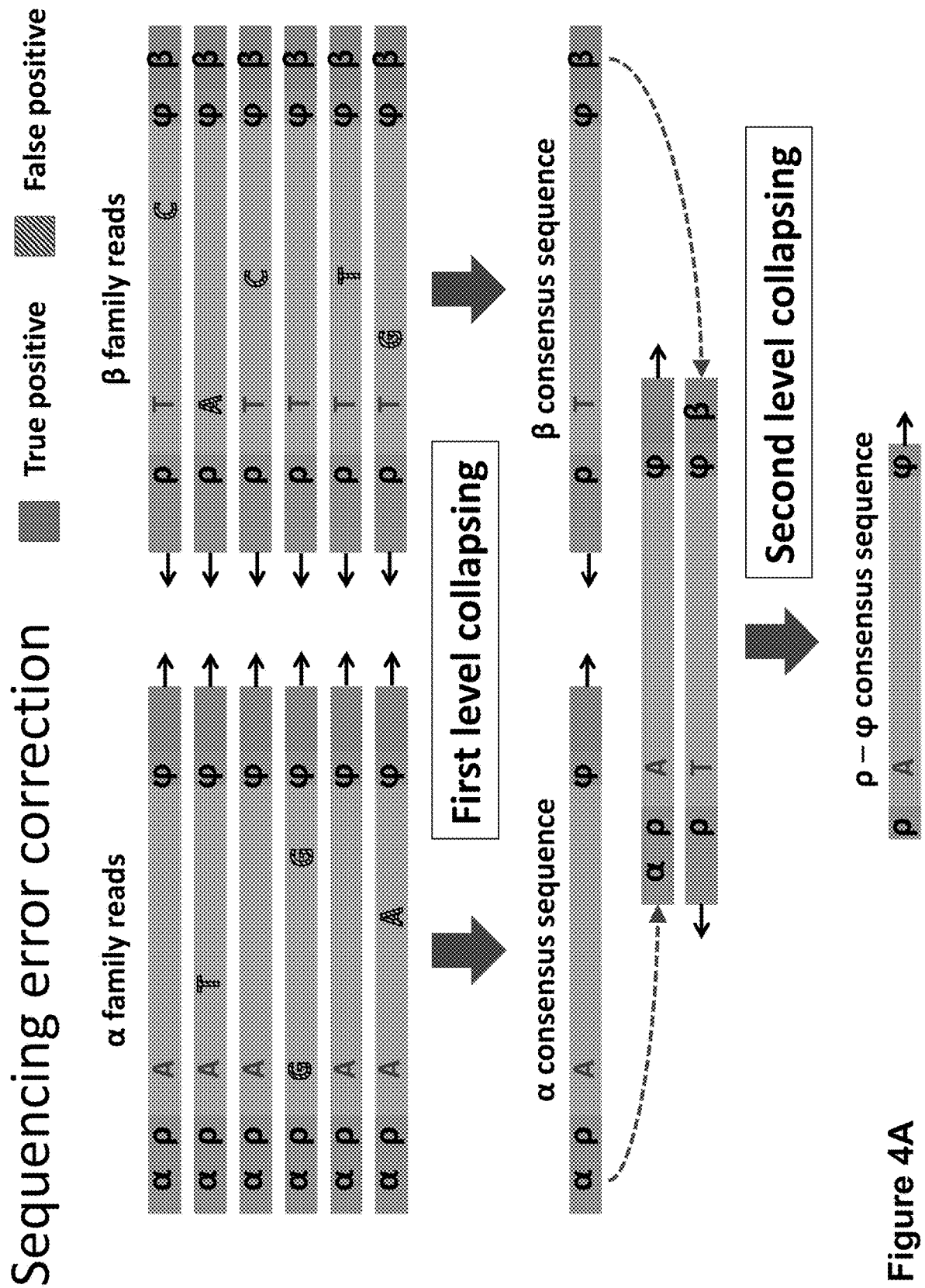
FIGS. 4A-4E illustrates how methods as disclosed herein can suppress different sources of error in determining the sequence of a double stranded DNA fragment.
Figure 4B:
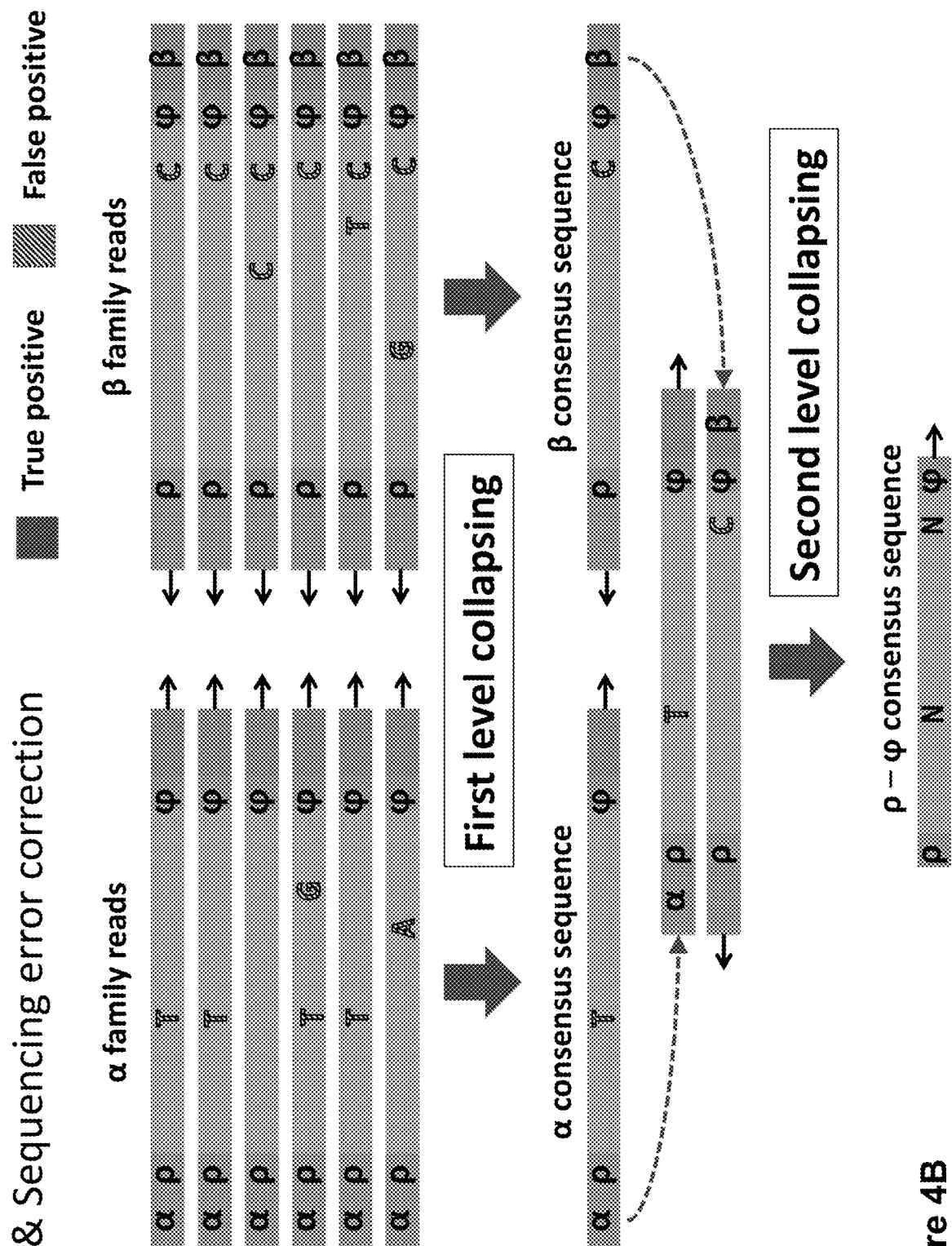
Figure 4C:
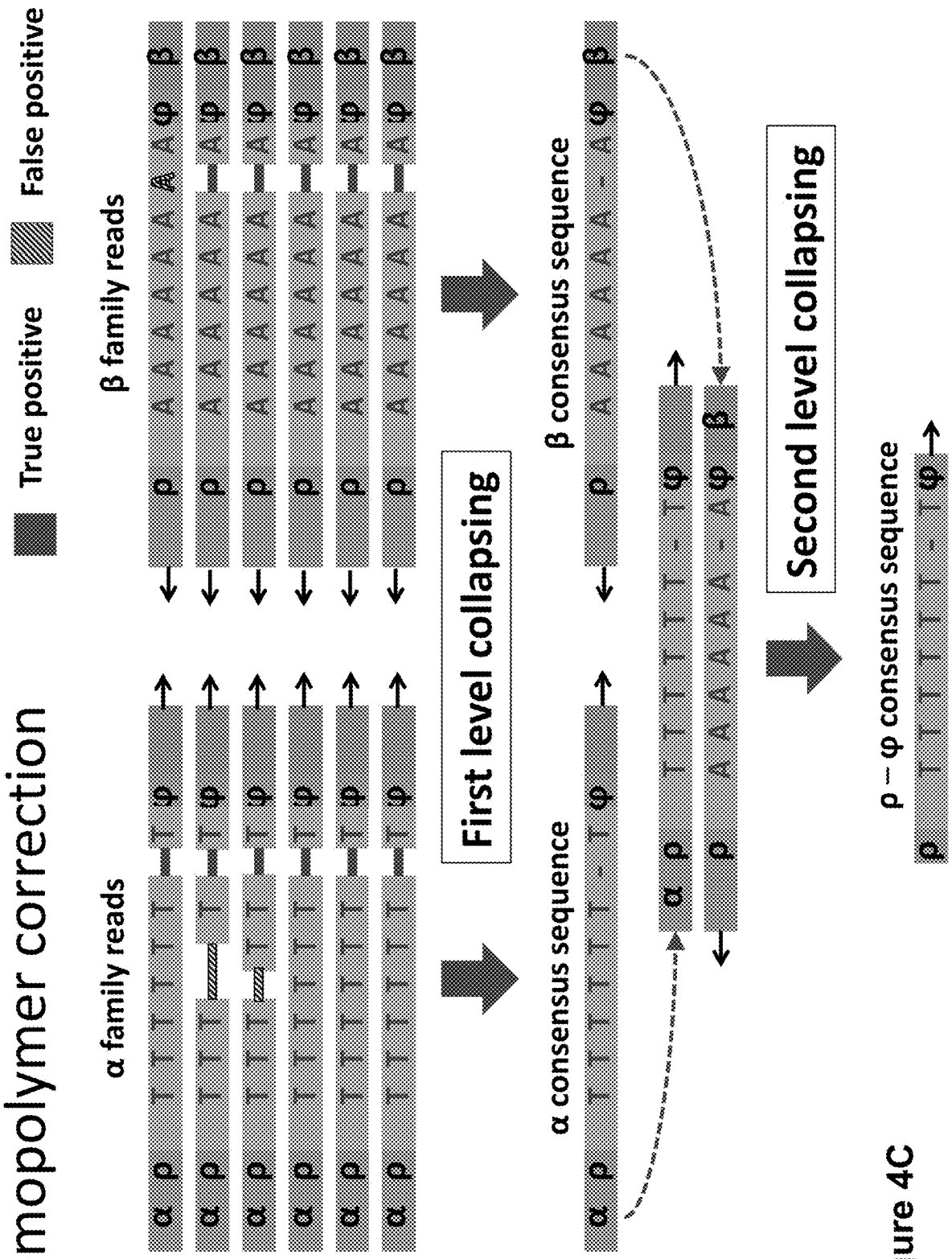
Figure 4D:
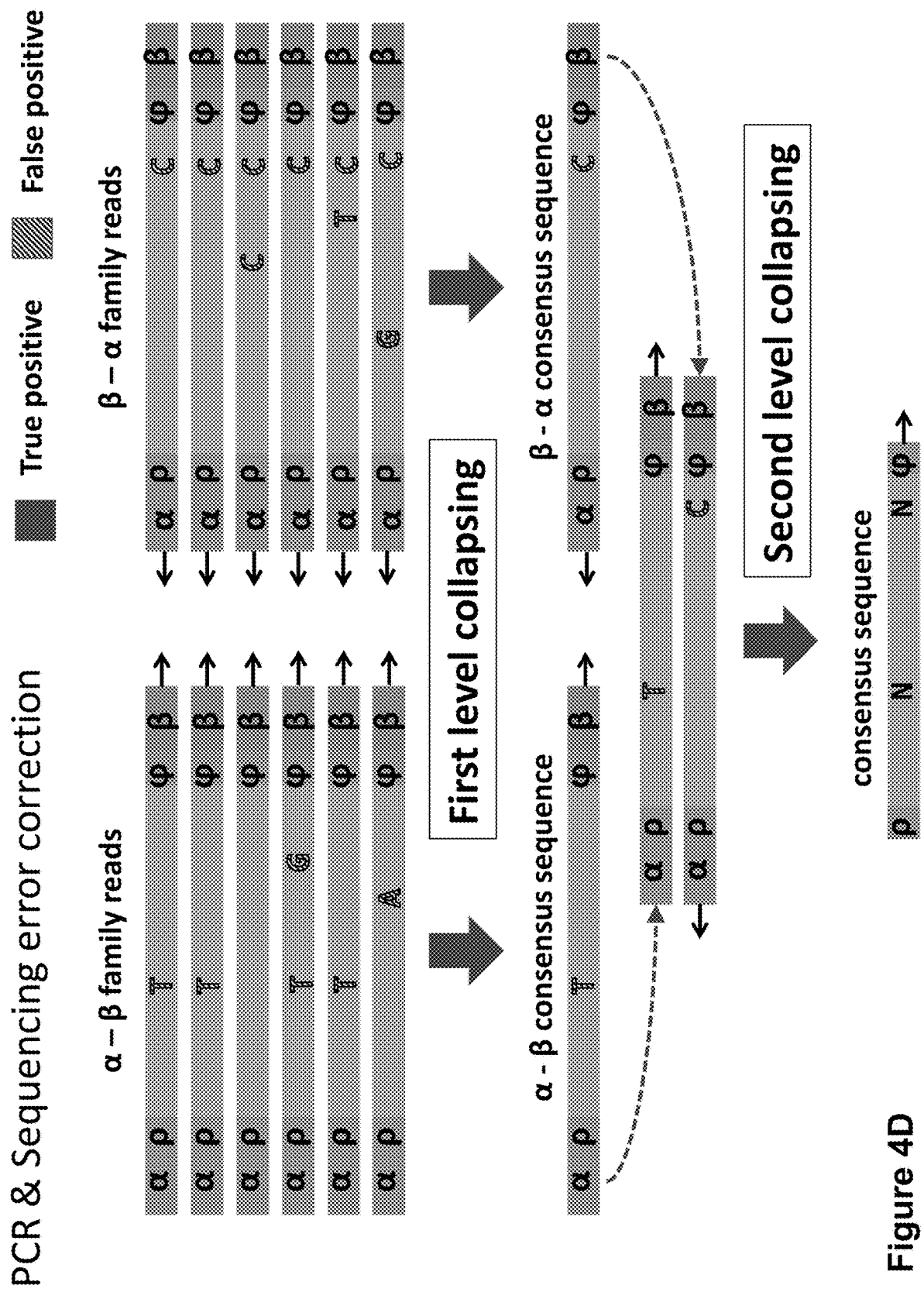
Figure 4E:
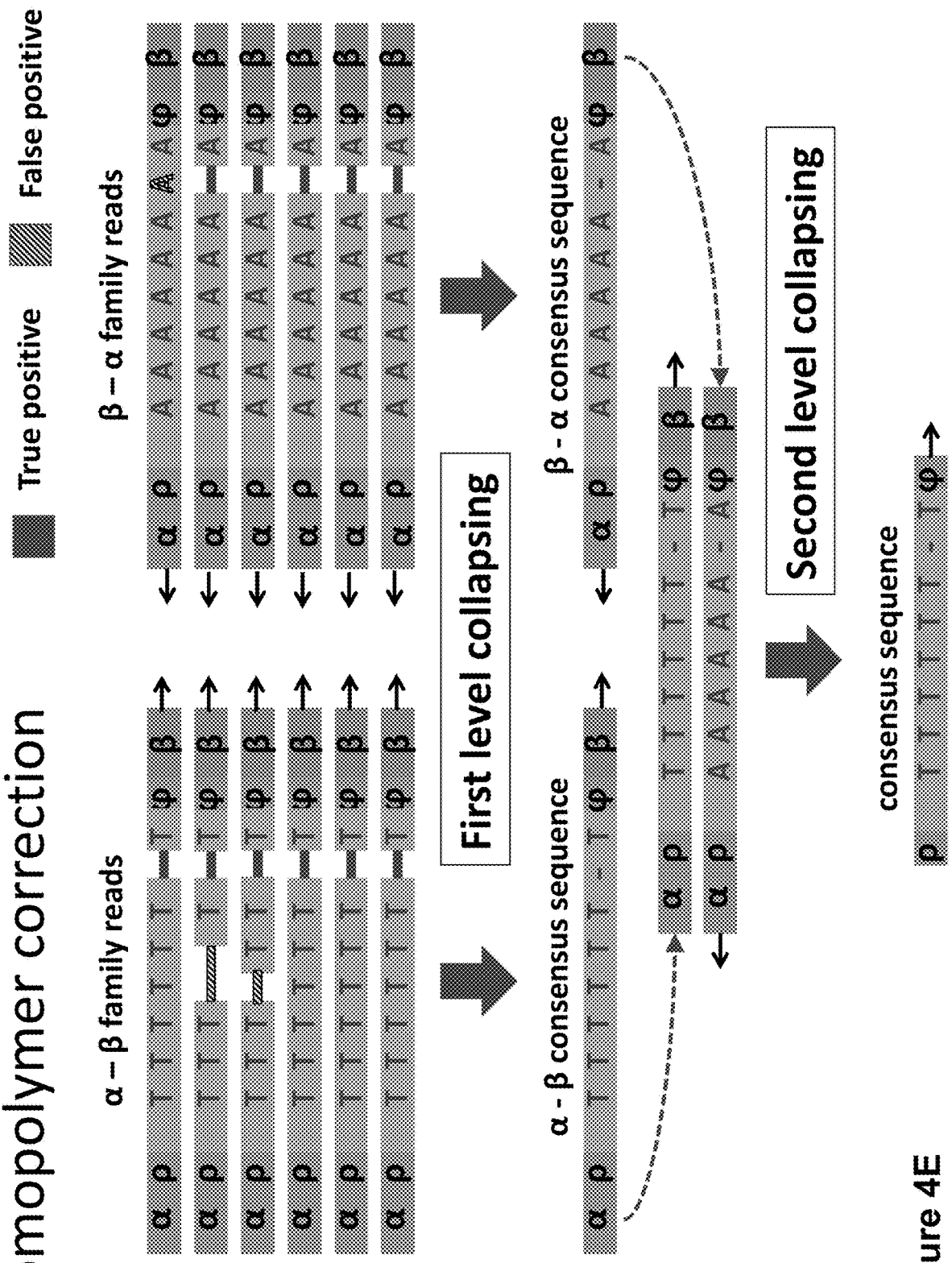

In alternative embodiments, reads having two physical UMIs on both ends, such as those shown in FIG. 3B and FIGS. 4D and 4E, may be collapsed in a second-level collapsing based on a combination of the physical UMIs and the virtual UMIs. This is especially helpful when the physical UMIs are too short to uniquely identify source DNA fragments without using the virtual UMIs. In these embodiments, second level collapsing can be implemented, with physical duplex UMIs as shown in FIG. 3B, by collapsing α-ρ-φ-β consensus reads and β-φ-ρ-α consensus reads from the same DNA molecule, thereby obtaining a consensus sequence including nucleotides consistent among all of the reads.

Using UMI and collapsing scheme described herein, various embodiments can suppress different sources of error affecting the determined sequence of a fragment even if the fragment includes alleles with very low allele frequencies. Reads sharing the same UMIs (physical and/or virtual) are grouped together. By collapsing the grouped reads, variants (SNV and small indels) due to PCR, library preparation, clustering, and sequencing errors can be eliminated. FIGS. 4A-4E illustrate how a method as disclosed in an example workflow can suppress different sources of error in determining the sequence of a double stranded DNA fragment. The illustrated reads include α-ρ-φ or β-φ-ρ UMIs in FIGS. 3A and 4A-4C, and α-ρ-φ-β or β-φ-ρ-α UMIs in FIGS. 3B, 4D and 4E. The α and β UMIs are singleplex physical UMIs in FIGS. 3A and 4A-4C. The α and β UMIs are duplex UMIs in FIGS. 3B, 4D and 4E. The virtual UMIs ρ and φ are located at the ends of a DNA fragment.

The method using singleplex physical UMIs as shown in FIGS. 4A-4C first involves collapsing reads having the same physical UMI α or β, illustrated as first level collapsing. The first level collapsing obtains an α consensus sequence for reads having the physical UMI α, which reads are derived from one strand of the double-stranded fragment. The first level collapsing also obtains a β consensus sequence for reads having the physical UMI β, which reads are derived from another strand of the double-stranded fragment. At a second level collapsing, the method obtains a third consensus sequence from the α consensus sequence and the β consensus sequence. The third consensus sequence reflects consensus base pairs from reads having the same duplex virtual UMIs ρ and φ, which reads are derived from two complementary strands of the source fragment. Finally, the sequence of the double stranded DNA fragment is determined as the third consensus sequence.

The method using duplex physical UMIs as shown in FIGS. 4D-4E first involves collapsing reads having the physical UMIs α and β with an α→β order in the 5'-3' direction, illustrated as first level collapsing. The first level collapsing obtains an α-β consensus sequence for reads having the physical UMIs α and β, which reads are derived from a first strand of the double-stranded fragment. The first level collapsing also obtains a β-α consensus sequence for reads having the physical UMIs β and α with a β→α order in the 5'-3' direction, which reads are derived from a second strand complementary to the first strand of the double-stranded fragment. At a second level collapsing, the method obtains a third consensus sequence from the α-β consensus sequence and the β-α consensus sequence. The third consensus sequence reflects consensus base pairs from reads having the same duplex virtual UMIs ρ and φ, which reads are derived from two strands of the fragment. Finally, the sequence of the double stranded DNA fragment is determined as the third consensus sequence.

FIG. 4A illustrates how a first-level collapsing may suppress sequencing errors. Sequencing errors occur on the sequencing platform after sample and library preparation (e.g., PCR amplification). Sequencing errors may introduce different erroneous bases into different reads. True positive bases are illustrated by solid letters, while false positive bases are illustrated by hatched letters. False positive nucleotides on different reads in the α-ρ-φ family have been excluded from the α consensus sequence. The true positive nucleotide "A" illustrated on the left ends of the α-ρ-φ family reads is retained for the α consensus sequence. Similarly, false positive nucleotides on different reads in the β-φ-ρ family have been excluded from the β consensus sequence, retaining the true positive nucleotide "A". As illustrated here, the first level collapsing can effectively remove sequencing errors. FIG. 4A also shows an optional second-level collapsing relying on the virtual UMIs ρ and φ. This second-level collapsing may further suppress errors as explained above, but such errors are not illustrated in FIG. 4A.

PCR errors occur before clustering amplification. Therefore, one erroneous base pair introduced into a single stranded DNA by the PCR process may be amplified during clustering amplification, thereby appearing in multiple clusters and reads. As illustrated in FIG. 4B and FIG. 4D, a false positive base pair introduced by PCR error may appear in many reads. The "T" base in the α-ρ-φ (FIG. 4B) or α-β (FIG. 4D) family reads and the "C" base in the β-φ-ρ (FIG. 4B) or β-α (FIG. 4D) family reads are such PCR errors. In contrast, the sequencing errors shown in FIG. 4A appear on one or a few reads in the same family. Because PCR sequencing errors appear in many reads of the family, a first-level collapsing of reads in a strand does not remove the PCR errors, even though the first-level collapsing removes sequencing errors (e.g., G and A removed from the α-ρ-φ family in FIG. 4B and the α-β family in FIG. 4D). However, since a PCR error is introduced into a single stranded DNA, the complementary strand of the source fragment and reads derived therefrom usually do not have the same PCR error. Therefore, the second-level collapsing based on reads from the two strands of the source fragment can effectively remove PCR errors as shown at the bottom of FIGS. 4B and 4D.

In some sequencing platforms, homopolymer errors occur to introduce small indel errors into homopolymers of repeating single nucleotides. FIGS. 4C and 4E illustrate homopolymer error correction using the methods described herein. In the α-ρ-φ (FIG. 4C) or α-ρ-φ-β (FIG. 4E) family reads, two "T" nucleotides have been deleted from the second read from the top, and one "T" nucleotide has been deleted from the third read from the top. In the β-φ-ρ (FIG. 4C) or β-φ-ρ-α (FIG. 4E) family reads, one "T" nucleotides has been inserted into the first read from the top. Similar to sequencing error illustrated in FIG. 4A, homopolymer errors occur after PCR amplification, therefore different reads have different homopolymer errors. As a result, the first level collapsing can effectively remove indel errors.

Consensus sequences may be obtained by collapsing reads having one or more common nonrandom UMI and one or more common virtual UMIs. Furthermore, position information may also be used to obtained consensus sequences as described below.

Collapsing by Position

In some implementations, reads are processed to align to a reference sequence to determine alignment locations of the reads on the reference sequence (localization). However, in some implementations not illustrated above, localization is achieved by k-mer similarity analysis and read-read alignment. This second implementation has two advantages: first, it can collapse (error correct) reads that do not match the reference, due to haplotype differences or translocations, and secondly, it does not depend on an aligner algorithm, thereby removing the possibility of aligner-induced artifacts (errors in the aligner). In some implementations, reads sharing the same localization information may be collapsed to obtain consensus sequences to determine the sequence of the source DNA fragments. In some contexts, the alignment process is also referred to as a mapping process. Sequence reads undergo an alignment process to be mapped to a reference sequence. Various alignment tools and algorithms may be used to align reads to the reference sequence as described elsewhere in the disclosure. As usual, in alignment algorithms, some reads are successfully aligned to the reference sequence, while others may not be successfully aligned or may be poorly aligned to the reference sequence. Reads that are successively aligned to the reference sequence are associated with sites on the reference sequence. Aligned reads and their associated sites are also referred to as sequence tags. Some sequence reads that contain a large number of repeats tend to be harder to align to the reference sequence. When a read is aligned to a reference sequence with a number of mismatched bases above a certain criterion, the read is considered poorly aligned. In various embodiments, reads are considered poorly aligned when they are aligned with at least about 1, 2, 3, 4, 5, 6, 7, 8, 9, or 10 mismatches. In other embodiments, reads are considered poorly aligned when they are aligned with at least about 5% of mismatches. In other embodiments, reads are considered poorly aligned when is they are aligned with at least about 10%, 15%, or 20% mismatched bases.

In some implementations, the disclosed methods combine position information with physical UMI information to index source molecules of DNA fragments. Sequence reads sharing a same read position and a same nonrandom or random physical UMI may be collapsed to obtain a consensus sequence for determining the sequence of a fragment or portion thereof. In some implementations, sequence reads sharing the same read position, the same nonrandom physical UMI, and a random physical UMI may be collapsed to obtain a consensus sequence. In such implementations, the adapter may include both a nonrandom physical UMI and a random physical UMI. In some implementations, sequence reads sharing the same read position and the same virtual UMI may be collapsed to obtain a consensus sequence.

Read position information may be obtained by different techniques. For example, in some implementations, genomic coordinates may be used to provide read position information. In some implementations, the position on a reference sequence to which a read is aligned can be used to provide read position information. For example, the start and stop positions of a read on a chromosome may be used to provide read position information. In some implementations, read positions are considered the same if they have identical position information. In some implementations, read positions are considered the same if the difference between the position information is smaller than a defined criterion. For instance, two reads having start genomic positions that differ by less than 2, 3, 4, or 5, base pairs can be considered as reads having the same read position. In other implementations, read positions are considered the same if their position information can be converted to and matched in a particular position space. A reference sequence may be provided prior to sequencing—for example, it may be a well-known and widely-used human genomic sequence—or it may be determined from the reads obtained during sequencing the sample.

Regardless of the specific sequencing platform and protocol, at least a portion of the nucleic acids contained in the sample are sequenced to generate tens of thousands, hundreds of thousands, or millions of sequence reads, e.g., 100 bp reads. In some embodiments, the sequence reads comprise about 20 bp, about 25 bp, about 30 bp, about 35 bp, about 36 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, about 800 bp, about 1000 bp, or about 2000 bp.

In some embodiments, reads are aligned to a reference genome, e.g., hg19. In other embodiments, reads are aligned to a portion of a reference genome, e.g., a chromosome or a chromosome segment. The reads that are uniquely mapped to the reference genome are known as sequence tags. In one embodiment, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags are obtained from reads that map uniquely to a reference genome.

Applications

In various applications, error correction strategies as disclosed herein may provide one or more of the following benefits: (i) detect very low allele frequency somatic mutations, (ii) decrease cycle time by mitigating phasing/pre-phasing errors, and/or (iii) increase read length by boosting quality of base calls at the later part of reads, etc. The applications and rationales regarding detection of low allele frequency somatic mutations are discussed above.

In certain embodiments, the techniques described herein may permit reliable calling of alleles having frequencies of about 2% or less, or about 1% or less, or about 0.5% or less. Such low frequencies are common in cfDNA originating from tumor cells in a cancer patient. In some embodiments, the techniques described here may permit the identification of rare strains in metagenomic samples, as well as the detection of rare variants in viral or other populations when, for example, a patient has been infected by multiple viral strains, and/or has undergone medical treatment.

In certain embodiments, the techniques described herein may allow shorter sequencing chemistry cycle time. The shortened cycle time increases sequencing errors, which can be corrected using method described above.

In some implementations involving UMIs, long reads may be obtained from paired end sequencing using asymmetric read lengths for a pair of paired-end (PE) reads from two ends of a segment. For instance, a pair of reads having 50 bp in one paired-end read and 500 bp in another paired-end read can be may be "stitched" together with another pair of reads to produce a long read of 1000 bp. These implementations may provide faster sequencing speed for to determine long fragments of low allele frequencies.

Figure 5:
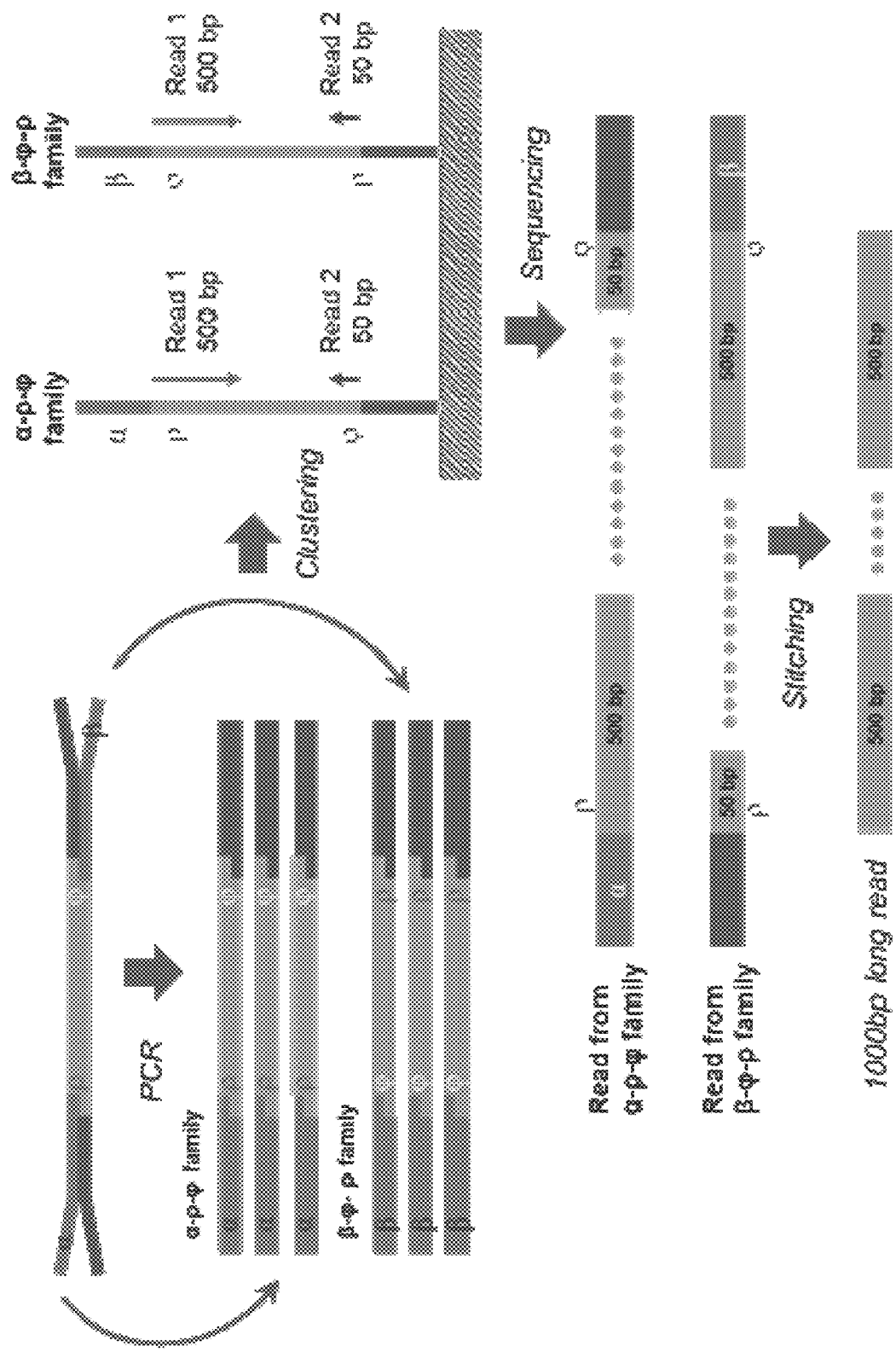
FIG. 5 schematically illustrates applying physical UMIs and virtual UMIs to efficiently obtain long pair end reads.

FIG. 5 schematically illustrates an example to efficiently obtain long paired end reads in this kind of applications by applying physical UMIs and virtual UMIs. Libraries from both strands of same DNA fragments are clustered on the flowcell. The insert size of library is longer than 1 Kb. Sequencing is performed with asymmetric read lengths (e.g., Read1=500 bp, Read2=50 bp), to ensure the quality of long 500 bp reads. Stitching two strands, 1000 bp long PE reads can be created with only 500+50 bp sequencing.

Samples

Samples that are used for determining DNA fragment sequence can include samples taken from any cell, fluid, tissue, or organ including nucleic acids in which sequences of interest are to be determined. In some embodiments involving diagnosis of cancers, circulating tumor DNA may be obtained from a subject's bodily fluid, e.g. blood or plasma. In some embodiments involving diagnosis of fetus, it is advantageous to obtain cell-free nucleic acids, e.g., cell-free DNA (cfDNA), from maternal body fluid. Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]).

In various embodiments the nucleic acids (e.g., DNA or RNA) present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample is un-enriched for DNA.

The sample including the nucleic acids to which the methods described herein are applied typically include a biological sample ("test sample") as described above. In some embodiments, the nucleic acids to be sequenced are purified or isolated by any of a number of well-known methods.

Accordingly, in certain embodiments the sample includes or consists essentially of a purified or isolated polynucleotide, or it can include samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, stool, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can include two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent, and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acids from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

Sequencing Library Preparation

In various embodiments, sequencing may be performed on various sequencing platforms that require preparation of a sequencing library. The preparation typically involves fragmenting the DNA (sonication, nebulization or shearing), followed by DNA repair and end polishing (blunt end or A overhang), and platform-specific adapter ligation. In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several billion reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as noncoding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Paired end reads may be used for the sequencing methods and systems disclosed herein. The fragment or insert length is longer than the read length, and sometimes longer than the sum of the lengths of the two reads.

In some illustrative embodiments, the sample nucleic acid(s) are obtained as genomic DNA, which is subjected to fragmentation into fragments of longer than approximately 50, 100, 200, 300, 400, 500, 600, 700, 800, 900, 1000, 2000, or 5000 base pairs, to which NGS methods can be readily applied. In some embodiments, the paired end reads are obtained from inserts of about 100-5000 bp. In some embodiments, the inserts are about 100-1000 bp long. These are sometimes implemented as regular short-insert paired end reads. In some embodiments, the inserts are about 1000-5000 bp long. These are sometimes implemented as long-insert mate paired reads as described above.

In some implementations, long inserts are designed for evaluating very long sequences. In some implementations, mate pair reads may be applied to obtain reads that are spaced apart by thousands of base pairs. In these implementations, inserts or fragments range from hundreds to thousands of base pairs, with two biotin junction adapters on the two ends of an insert. Then the biotin junction adapters join the two ends of the insert to form a circularized molecule, which is then further fragmented. A sub-fragment including the biotin junction adapters and the two ends of the original insert is selected for sequencing on a platform that is designed to sequence shorter fragments.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adapters, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described in the example workflow above with reference to FIGS. 1A and 1B, instruct users to end-repair sample DNA, to purify the end-repaired products prior to adenylating or dA-tailing the 3' ends, and to purify the dA-tailing products prior to the adapter-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

The methods and apparatus described herein may employ next generation sequencing technology (NGS), which allows massively parallel sequencing. In certain embodiments, clonally amplified DNA templates or single DNA molecules are sequenced in a massively parallel fashion within a flow cell (e.g., as described in Volkerding et al. Clin Chem 55:641-658 [2009]; Metzker M Nature Rev 11:31-46 [2010]). The sequencing technologies of NGS include but are not limited to pyrosequencing, sequencing-by-synthesis with reversible dye terminators, sequencing by oligonucleotide probe ligation, and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are further described here.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORREN™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In some embodiments, the disclosed methods involve obtaining sequence information for the nucleic acids in the test sample by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA or circulating tumor DNA (ctDNA) is used as the template, and fragmentation is not required as cfDNA or ctDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos. Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free genomic library preparation is used, and the randomly fragmented genomic DNA is enriched using the cluster amplification alone (Kozarewa et al., Nature Methods 6:291-295 [2009]). In some applications, the templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adapters attached to the two ends of the fragment, the adapters allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced from both ends is also referred to as an insert.

In some implementation, a flow cell for clustering in the Illumina platform is a glass slide with lanes. Each lane is a glass channel coated with a lawn of two types of oligos (e.g., P5 and P7' oligos). Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification and other sequencing methods involving clustering, a strand folds over, and a second adapter region on a second end of the strand hybridizes with the second type of oligos on the flow cell surface. A polymerase generates a complementary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves 2 reads from the two ends of a fragment. Paired end reads are used to resolve ambiguous alignments. Paired-end sequencing allows users to choose the length of the insert (or the fragment to be sequenced) and sequence either end of the insert, generating high-quality, alignable sequence data. Because the distance between each paired read is known, alignment algorithms can use this information to map reads over repetitive regions more precisely. This results in better alignment of the reads, especially across difficult-to-sequence, repetitive regions of the genome. Paired-end sequencing can detect rearrangements, including insertions and deletions (indels) and inversions.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is specifically referred to as mate pair reads. In some embodiments involving mate pair reads, two biotin junction adapters first are attached to two ends of a relatively long insert (e.g., several kb). The biotin junction adapters then link the two ends of the insert to form a circularized molecule. A sub-fragment encompassing the biotin junction adapters can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following address, which is incorporated by reference by its entirety: res.illumina.com/documents/products/technotes/technote_nextera_matepair_data_processing.pdf After sequencing of DNA fragments, sequence reads of predetermined length, e.g., 100 bp, are localized by mapping (alignment) to a known reference genome. The mapped reads and their corresponding locations on the reference sequence are also referred to as tags. In another embodiment of the procedure, localization is realized by k-mer sharing and read-read alignment. The analyses of many embodiments disclosed herein make use of reads that are either poorly aligned or cannot be aligned, as well as aligned reads (tags). In one embodiment, the reference genome sequence is the NCBI36/hg18 sequence, which is available on the World Wide Web at genome.ucsc.edu/cgi-bin/hgGateway?org=Human&db=hg18&hgsid=166260105). Alternatively, the reference genome sequence is the GRCh37/hg19 or GRCh38, which is available on the World Wide Web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

Other sequencing methods may also be used to obtain sequence reads and alignments thereof. Additional suitable methods are described in U.S. patent application Ser. No. 15/130,668 filed no Apr. 15, 2016, which is incorporated by reference in its entirety.

In some embodiments of the methods described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In some embodiments, paired end reads are used to determine sequences of interest, which comprise sequence reads that are about 20 bp to 1000 bp, about 50 bp to 500 bp, or 80 bp to 150 bp. In various embodiments, the paired end reads are used to evaluate a sequence of interest. The sequence of interest is longer than the reads. In some embodiments, the sequence of interest is longer than about 100 bp, 500 bp, 1000 bp, or 4000 bp. Mapping of the sequence reads is achieved by comparing the sequence of the reads with the sequence of the reference to determine the chromosomal origin of the sequenced nucleic acid molecule, and specific genetic sequence information is not needed. A small degree of mismatch (0-2 mismatches per read) may be allowed to account for minor polymorphisms that may exist between the reference genome and the genomes in the mixed sample. In some embodiments, reads that are aligned to the reference sequence are used as anchor reads, and reads paired to anchor reads but cannot align or poorly align to the reference are used as anchored reads. In some embodiments, poorly aligned reads may have a relatively large number of percentage of mismatches per read, e.g., at least about 5%, at least about 10%, at least about 15%, or at least about 20% mismatches per read.

A plurality of sequence tags (i.e., reads aligned to a reference sequence) are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags of, e.g., 100 bp, are obtained from mapping the reads to the reference genome per sample. In some embodiments, all the sequence reads are mapped to all regions of the reference genome, providing genome-wide reads. In other embodiments, reads mapped to a sequence of interest.

Apparatus and Systems for Sequencing Using UMIs

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. In particular, various general-purpose machines may be used with programs written in accordance with the teachings herein, or it may be more convenient to construct a more specialized apparatus to perform the required method steps. A particular structure for a variety of these machines is shown and described below.

Certain embodiments also provide functionality (e.g., code and processes) for storing any of the results (e.g., query results) or data structures generated as described herein. Such results or data structures are typically stored, at least temporarily, on a computer readable medium. The results or data structures may also be output in any of various manners such as displaying, printing, and the like.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

One implementation provides a system for use in determining a sequence with low allele frequency in a test sample including nucleic acids, the system including a sequencer for receiving a nucleic acid sample and providing nucleic acid sequence information from the sample; a processor; and a machine readable storage medium having stored thereon instructions for execution on said processor to determine a sequence of interest in the test sample by: (a) applying adapters to DNA fragments in the sample to obtain DNA-adapter products, wherein each adapter comprises a nonrandom unique molecular index, and wherein nonrandom unique molecular indices of the adapters have at least two different molecular lengths and form a set of variable-length, nonrandom unique molecular indices (vNRUMIs); (b) amplifying the DNA-adapter products to obtain a plurality of amplified polynucleotides; (c) sequencing, using the sequencer, the plurality of amplified polynucleotides, thereby obtaining a plurality of reads associated with the set of vNRUMIs; (d) identifying, by the processor and among the plurality of reads, reads associated with a same variable-length, nonrandom unique molecular index (vNRUMI); and (e) determining a sequence of a DNA fragment in the sample using the reads associated with the same vNRUMI.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

Another implementation provides a system including nucleic acid synthesizer, a processor, and a machine readable storage medium having stored thereon instructions for execution on said processor to prepare sequencing adapters. The instructions includes: (a) providing, by the processor a set of oligonucleotide sequences having at least two different molecular lengths; (b) selecting by the processor a subset of oligonucleotide sequences from the set of oligonucleotide sequences, all edit distances between oligonucleotide sequences of the subset of oligonucleotide sequences meeting a threshold value, the subset of oligonucleotide sequences forming a set of variable-length, nonrandom unique molecular indexes (vNRUMIs); and (c) synthesizing, using the nucleic acid synthesizer, a plurality of sequencing adapters, wherein each sequencing adapter comprises a double-stranded hybridized region, a single-stranded 5' arm, a single-stranded 3' arm, and at least one vNRUMI of the set of vNRUMIs.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, reference sequences (including reference sequences providing solely or primarily polymorphisms), calls such as cancer diagnosis calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the sequence of a DNA fragment of interest in a test sample. The computer product may contain instructions for performing any one or more of the above-described methods for determining a sequence of interest. As explained, the computer product may include a non-transitory and/or tangible computer readable medium having a computer executable or compilable logic (e.g., instructions) recorded thereon for enabling a processor to determine a sequence of interest. In one example, the computer product comprises a computer readable medium having a computer executable or compilable logic (e.g., instructions) recorded thereon for enabling a processor to diagnose a condition or determine a nucleic acid sequence of interest.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable calls of low allele frequency mutations generally require mapping thousands (e.g., at least about 10,000) or even millions of reads to one or more chromosomes.

The methods disclosed herein can be performed using a system for determining a sequence of interest in a test sample. The system may include: (a) a sequencer for receiving nucleic acids from the test sample providing nucleic acid sequence information from the sample; (b) a processor; and (c) one or more computer-readable storage media having stored thereon instructions for execution on said processor to determining a sequence of interest in the test sample. In some embodiments, the methods are instructed by a computer-readable medium having stored thereon computer-readable instructions for carrying out a method for determining the sequence of interest. Thus one embodiment provides a computer program product including a non-transitory machine readable medium storing program code that, when executed by one or more processors of a computer system, causes the computer system to implement a method for determining the sequences of nucleic acid fragments in a test sample. The program code may include: (a) code for obtaining a plurality of reads of a plurality of amplified polynucleotides, each polynucleotide of the plurality of amplified polynucleotides comprising an adapter attached to a DNA fragment, wherein the adapter comprises a nonrandom unique molecular index, and wherein nonrandom unique molecular indexes of the adapters have at least two different molecular lengths, forming a set of variable-length, nonrandom unique molecular indexes (vNRUMIs); (b) code for identifying, among the plurality of reads, reads associated with a same vNRUMIs; and (c) code for determining, using the reads associated with the same vNRUMI, a sequence of a DNA fragment in the sample.

In some embodiments, the program codes or the instructions may further include automatically recording information pertinent to the method. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the test sample was taken. This may involve performing one or more additional tests or analyses on additional samples taken from the subject.

Disclosed methods can also be performed using a computer processing system which is adapted or configured to perform a method for determining a sequence of interest. One embodiment provides a computer processing system which is adapted or configured to perform a method as described herein. In one embodiment, the apparatus includes a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Thresholds for calling a test sample as either affected, non-affected, or no call The actual calls of medical conditions related to the sequence of interest Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to determine a sequence of interest. At this remote location, as an example, the reads are aligned to a reference sequence to produce anchor and anchored reads. Among the processing operations that may be employed at distinct locations are the following:

Sample collection

Sample processing preliminary to sequencing

Sequencing

Analyzing sequence data and deriving medical calls

Diagnosis

Reporting a diagnosis and/or a call to patient or health care provider

Developing a plan for further treatment, testing, and/or monitoring

Executing the plan

Counseling

Any one or more of these operations may be automated as described elsewhere herein. Typically, the sequencing and the analyzing of sequence data and deriving medical calls will be performed computationally. The other operations may be performed manually or automatically.

Figure 6:
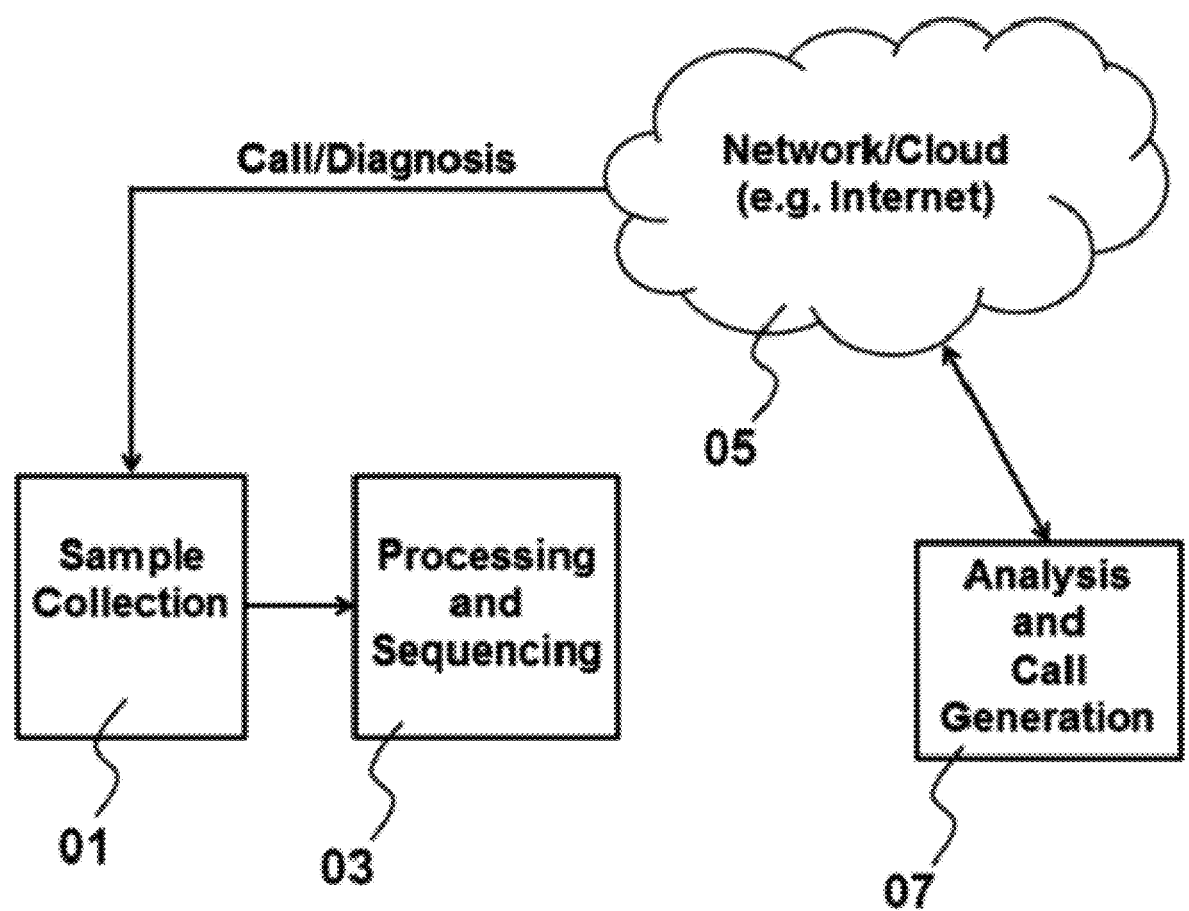
FIG. 6 is a block diagram of a dispersed system for processing a test sample.

FIG. 6 shows one implementation of a dispersed system for producing a call or diagnosis from a test sample. A sample collection location 01 is used for obtaining a test sample from a patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 6.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 6. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 7:
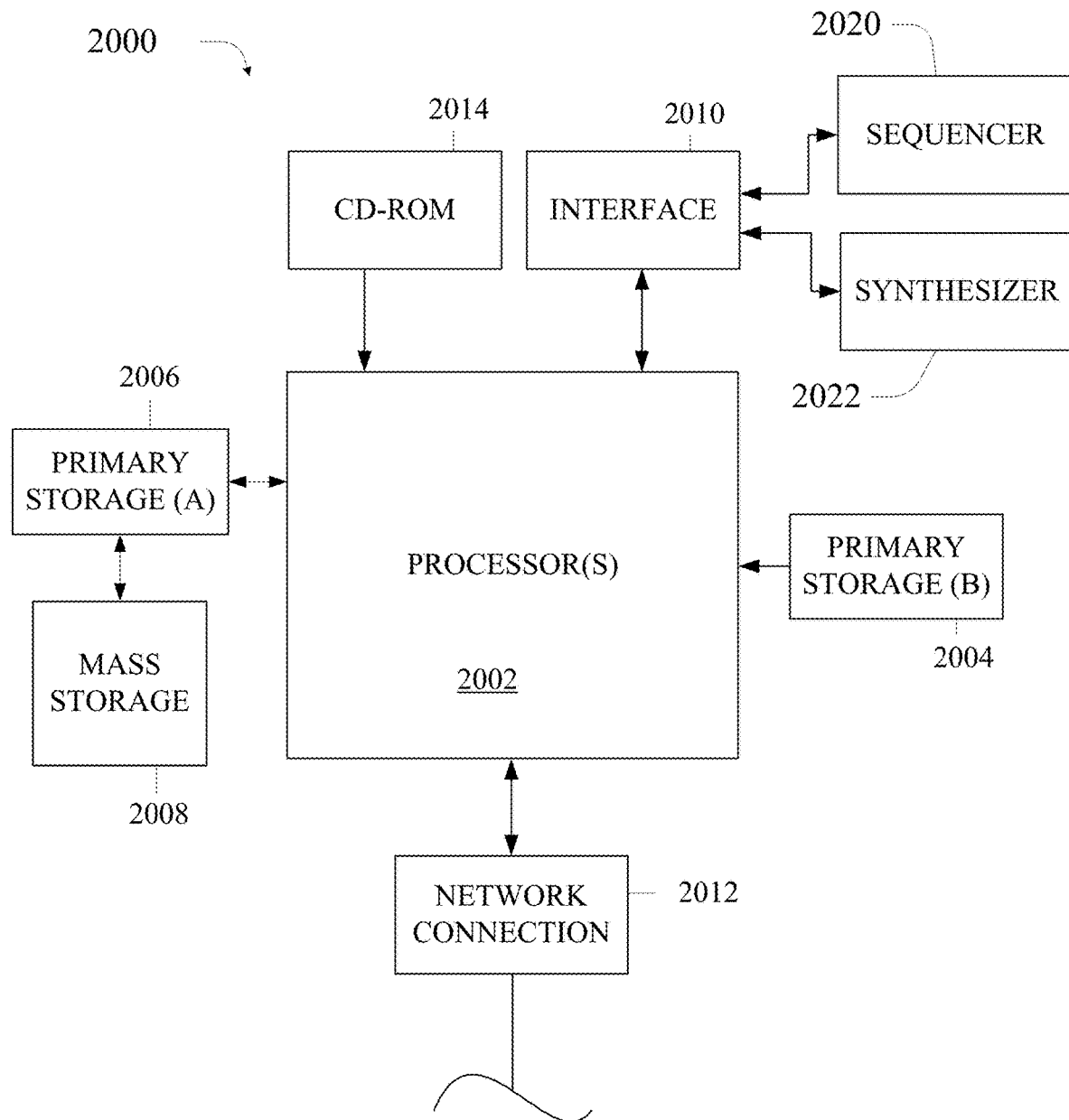
FIG. 7 illustrates a computer system that can serve as a computational apparatus according to certain embodiments.

FIG. 7 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions uni-directionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data uni-directionally to the CPU or primary storage.

CPU 2002 is also coupled to an interface 2010 that connects to one or more input/output devices such as such as a nucleic acid sequencer (2020), a nucleic acid synthesizer (2022), video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein. In some implementations, a nucleic acid sequencer or a nucleic acid synthesizer, may be communicatively linked to the CPU 2002 via the network connection 2012 instead of or in addition to via the interface 2010.

In one embodiment, a system such as computer system 2000 is used as a data import, data correlation, and querying system capable of performing some or all of the tasks described herein. Information and programs, including data files can be provided via a network connection 2012 for access or downloading by a researcher. Alternatively, such information, programs and files can be provided to the researcher on a storage device.

In a specific embodiment, the computer system 2000 is directly coupled to a data acquisition system such as a microarray, high-throughput screening system, or a nucleic acid sequencer (2020) that captures data from samples. Data from such systems are provided via interface 2010 for analysis by system 2000. Alternatively, the data processed by system 2000 are provided from a data storage source such as a database or other repository of relevant data. Once in apparatus 2000, a memory device such as primary storage 2006 or mass storage 2008 buffers or stores, at least temporarily, relevant data. The memory may also store various routines and/or programs for importing, analyzing and presenting the data, including sequence reads, UMIs, codes for determining sequence reads, collapsing sequence reads and correcting errors in reads, etc.

In certain embodiments, the computers used herein may include a user terminal, which may be any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms.

In certain embodiments, the computers used herein may also include a server system in communication with a user terminal, which server system may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

EXPERIMENTAL

Example 1

Comparison of vNRUMI Method and Other Barcode Methods

Table 1 shows the base pair heterogeneity of NRUMIs, compared to the base pair heterogeneity of vNRUMIs according to some implementations. This set of 120 vNRUMIs is comprised of 50 six-mers and 70 seven-mers. The NRUMI set is comprised entirely of 218 six-mers, where the minimal edit distance between any two NRUMIs exceeds a threshold value. Table 1 assumes each of the 218 or 128 barcodes was present in equal amounts, e.g., there are 1000 of each UMI. For the 7th base, the new vNRUMI set has much better heterogeneity than the original NRUMI set, and far exceeds the recommended minimum of 5% composition per base. Thus, it is clear that the vNRUMI design addresses the aforementioned challenge of lack of base pair diversity at certain cycles. Other sets of barcodes comprised exclusively of sixmers have a similar per-base heterogeneity as the original NRUMI set depicted below.

TABLE 1

Base pair Heterogeneity Within UMI Positions

| | NRUMIs (n = 218) | | | | vNRUMIs (n = 120) | | | |
|---|---|---|---|---|---|---|---|---|
| Base | A | C | G | T | A | C | G | T |
| 1 | 0.2431 | 0.2523 | 0.1972 | 0.3073 | 0.2667 | 0.2333 | 0.2417 | 0.2583 |
| 2 | 0.2844 | 0.2844 | 0.1468 | 0.2844 | 0.2500 | 0.2583 | 0.2250 | 0.2667 |
| 3 | 0.2431 | 0.2385 | 0.2523 | 0.2661 | 0.3083 | 0.2000 | 0.2500 | 0.2417 |
| 4 | 0.2110 | 0.2936 | 0.1514 | 0.3440 | 0.2583 | 0.2500 | 0.2750 | 0.2167 |
| 5 | 0.2018 | 0.2248 | 0.4083 | 0.1651 | 0.3000 | 0.1833 | 0.2167 | 0.3000 |
| 6 | 0.2018 | 0.3302 | 0.1009 | 0.3670 | 0.2750 | 0.2750 | 0.2667 | 0.1833 |
| 7 | 0 | 0 | 0 | 1 | 0.1917 | 0.1750 | 0.2167 | 0.4167 |

Using the NRUMIs and vNRUMIs above, in silico simulation studies were performed to simulate 10,000 barcodes, mutated every single barcode by mutating each base independently, and attempted to recover the original UMI sequence. The simulation used a mutation rate of 2% at each base (1% chance for SNV, 1% chance for indel of size 1). Note that this mutation rate is appreciably higher than typical Illumina sequencing error rates. Each of the 10,000 simulations contained at least one mutation.

To provide further comparison to other methods using UMIs, a set of 114 NRUMI sequences of length 6 nt generated according to an existing approach nxCode are also used in this simulation study. See http://hannonlab.cshl.edu/nxCode/nxCode/main.html. These sequences were subject to the same mutation process as described above. The nxCode approach uses a probabilistic model to determine mutations, and uses a semi-greedy approach to obtain a set of NRUMI having equal molecular length. Comparison results between the vNRUMI, NRUMI, and nxCode sets can be found in Table 2.

TABLE 2

Benchmark results comparing error correction rates for different UMI Designs

| Metric | vNRUMI | NRUMI | nxCode |
|---|---|---|---|
| Simulated Mutated UMIs | 10,000 | 10,000 | 10,000 |
| Uniquely Correctable | 7,703 | 2,447 | 3,829 |
| Within closest matches | 9,242 | 9,779 | 9,629 |
| Average size of closest set | 1.2138 | 3.0261 | 2.0978 |
| Within closest or second closest matches | 9,927 | 9,865 | 9,897 |
| Average size of second closest set | 3.9391 | 7.781 | 6.0504 |

The vNRUMIs set has 120 UMIs, of which 50 UMIs have length of 6 nt and 70 UMIs have length of 7 nt. The NRUMIs set has 218 sequences of length 6. A conventional approach nxCode uses a NRUMI set of 114 sequences of length 6 nt. Average size of a set is the average number of unique sequences included in a set.

In Table 2, a unique correction is defined as a case where the set of nearest neighbors has only one sequence in it; in other words, the UMI matching and correction algorithm described above gave an unambiguous suggestion for the most likely true vNRUMI. Note that the number of such uniquely correctable sequences is much larger for the vNRUMI methodology than NRUMI and nxCode. Also, the average size of the closest/second closest set is much smaller in vNRUMI approach than in other solutions, while the rate at which the original non-mutated barcode is contained within those sets is approximately equal. This is important because during read collapsing, contextual information is used to select a correct UMI from these closest/second closest sets. Providing this read collapsing step with fewer incorrect sequences can decrease the chance of it making an incorrect choice, ultimately improving the ability to suppress noise and detect variants.

It is worth noting that the NRUMI and nxCode approaches, like other previous barcoding strategies, assume that the barcode sequences are all of uniform length. In producing this simulation, to provide direct comparisons among the three approaches, the original methods for correcting errors described by the NRUMI and nxCode approaches were not used, which might have limited the performance of the NRUMI and nxCode approaches. However, the data in Table 2 provide an insight into vNRUMI approach's potential ability to improve error correction, which is further illustrated in the next example.

Example 2

Recovering DNA Fragments Using vNRUMIs and NRUMIs

In another set of in silo studies, the abilities of vNRUMI and NRUMIs to recover reads are tested. The studies pick a random COSMIC mutation and generate a single DNA fragment containing that mutation. The fragment size have an average of 166, and a standard deviation of 40. The simulation adds a random UMI to both ends of this fragment. It used ART (see, e.g., https://www.niehs.nih.gov/research/resources/software/biostatistics/art/) to simulate 10 paired-end reads of this UMI-fragment-UMI molecule, and align those reads using burrows wheeler aligner (BWA). See, e.g., http://bio-bwa.sourceforge.net/.

Then the process pass alignment into a proprietary read collapser, ReCo, to determine if it can recover the original fragment sequence and repeat the process for additional reads.

Table 3 shows the numbers and percentages of fragments that could recovered.

TABLE 3

Error correction rates for NRUMI and vNRUMI Designs

| Metric | Old 218 NRUMI | New 120 vNRUMI |
|---|---|---|
| Original fragment perfectly recovered | 16,837 (95.58%) | 16,915 (96.03%) |
| Original fragment not perfectly recovered | 778 (4.42%) | 700 (3.97%) |
| Sum | 17,615 (100%) | 17,615 (100%) |

The vNRUMI method recovered more fragments than the fixed-length NRUMI method. A Chi-square test shows that the differences are significant. $\chi^2=4.297$, two-tailed P value=0.0382. Using $\alpha=0.05$, the vNRUMI method achieved statistically better error correction performance compared to the NRUMI method, while addressing shortcoming of the NRUMI method.

The NRUMI strategy handles NRUMI sets of heterogeneous length. This addresses the base pair diversity issue that caused a drop in alignment quality.

Novel processes are provided for generating sets of variable length UMIs that satisfy biochemical restraints, and for mapping misread UMIs to correct UMIs. The novel approach addresses issue of decreased sequencing quality caused by uniform length barcodes. The use of matching scheme that is aware of number of matches and mismatches, as opposed to just tracking mismatches, allows improve ability of error correction. The implementations are comparable to or exceed existing solutions, while providing additional functionality.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for sequencing nucleic acid molecules from a sample, comprising
   (a) applying adapters to DNA fragments in the sample to obtain DNA-adapter products,
      wherein each adapter comprises a nonrandom unique molecular index,
      wherein nonrandom unique molecular indices of the adapters have at least two different molecular lengths and form a set of variable-length, nonrandom unique molecular indices (vNRUMIs), and
      wherein the adapters are obtained by:
         (i) providing a set of oligonucleotide sequences having at least two different molecular lengths,
         (ii) selecting a subset of oligonucleotide sequences from the set of oligonucleotide sequences, all edit distances between oligonucleotide sequences of the subset of oligonucleotide sequences meeting a threshold value, the subset of oligonucleotide sequences forming the set of vNRUMIs, and
         (iii) synthesizing the adapters each comprising a double-stranded hybridized region, a single-stranded 5' arm, a single-stranded 3' arm, and at least one vNRUMI of the set of vNRUMIs;
   (b) amplifying the DNA-adapter products to obtain a plurality of amplified polynucleotides;
   (c) sequencing the plurality of amplified polynucleotides, thereby obtaining a plurality of reads associated with the set of vNRUMIs;
   (d) identifying, among the plurality of reads, reads associated with a same variable-length, nonrandom unique molecular index (vNRUMI); and
   (e) determining a sequence of a DNA fragment in the sample using the reads associated with the same vNRUMI.

2. The method of claim 1, wherein the threshold value is 3.

3. The method of claim 1, wherein the set of vNRUMIs comprise vNRUMIs of 6 nucleotides and vNRUMIs of 7 nucleotides.

4. The method of claim 1, wherein (e) comprises collapsing reads associated with the same vNRUMI into a group to obtain a consensus nucleotide sequence for the sequence of the DNA fragment in the sample.

5. The method of claim 4, the consensus nucleotide sequence is obtained based partly on quality scores of the reads.

6. The method of claim 1, wherein (e) comprises:
identifying, among the reads associated with the same vNRUMI, reads having a same read position or similar read positions in a reference sequence, and
determining the sequence of the DNA fragment using reads that (i) are associated with the same vNRUMI and (ii) have the same read position or similar read positions in the reference sequence.

7. The method of claim 1, wherein the set of vNRUMIs includes no more than about 10,000 different vNRUMIs.

8. The method of claim 7, wherein the set of vNRUMIs includes no more than about 1,000 different vNRUMIs.

9. The method of claim 8, wherein the set of vNRUMIs includes no more than about 200 different vNRUMIs.

10. The method of claim 1, applying adapters to the DNA fragments in the sample comprises applying adapters to both ends of the DNA fragments in the sample.

\* \* \* \* \*